(12) United States Patent
Takahashi et al.

(10) Patent No.: US 7,856,318 B2
(45) Date of Patent: Dec. 21, 2010

(54) METHOD OF CLASSIFYING GENE EXPRESSION STRENGTH IN LUNG CANCER TISSUES

(75) Inventors: Takashi Takahashi, Nagoya (JP); Shuta Tomita, Nagoya (JP); Tetsuya Mitsudomi, Nagoya (JP); Yasushi Yatabe, Nagoya (JP); Nobuhiko Ogura, Ashigarakami-gun (JP); Masato Some, Ashigarakami-gun (JP)

(73) Assignees: Aichi Prefecture, Aichi Prefecture (JP); FUJIFILM Corporation, Tokyo (JP)

( * ) Notice: Subject to any disclaimer, the term of this patent is extended or adjusted under 35 U.S.C. 154(b) by 475 days.

(21) Appl. No.: 11/008,265

(22) Filed: Dec. 10, 2004

(65) Prior Publication Data
US 2005/0170386 A1 Aug. 4, 2005

(30) Foreign Application Priority Data
Dec. 12, 2003 (JP) .............................. 2003-415119

(51) Int. Cl.
*G01N 7/00* (2006.01)
(52) U.S. Cl. .............................. 702/19; 703/11; 435/6; 436/501
(58) Field of Classification Search ........................ None
See application file for complete search history.

(56) References Cited

U.S. PATENT DOCUMENTS

| 6,812,339 | B1 * | 11/2004 | Venter et al. | .............. 536/24.31 |
| 2003/0219760 | A1 * | 11/2003 | Gordon et al. | .................. 435/6 |
| 2009/0104617 | A1 * | 4/2009 | Gordon et al. | .................. 435/6 |

FOREIGN PATENT DOCUMENTS

| WO | WO 02/44331 A2 | 6/2002 |
| WO | WO 2004/005891 A2 | 1/2004 |
| WO | WO2006053442 | * 1/2006 |

OTHER PUBLICATIONS

Yoshida et al, "The clinical significance of Cyclin B1 and Wee1 expression in non-small-cell lung cancer"; Annals of Oncology; Official Journal of the European Society for Medical Oncology; Feb. 2004; pp. 252-256.
Wigle et al. "Molecular profiling of non-small cell lung cancer and correlation with disease-free survival"; Cancer Research, American Association for Cancer Research; Jun. 1, 2002; vol. 62, No. 11.
Han et al., "Prognostic value of immunohistochemical expression of p53, HER-2/neu, and bcl-2 in stage 1 non-small-cell lung cancer", Human Pathology, Jan. 2002; vol. 33, No. 1 pp. 105-110.
Horio et al. "Prognositc significance in p53 mutations and 3p deletion in primary resected non-small cell lung cancer"; Cancer Research; Jan. 1, 1993; pp. 1-4.
Ginsberg et al. "Non-small cell lung cancer" Cancer of the Lung; Chapter 30.2; pp. 858-911.
Moldvay J et al: "P53 expression in stage I squamous cell lung cancer." Pathology Oncology Research; 1998, vol. 4, No. 1, 1998, pp. 8-13, XP002431203.
Volm M et al: "Prognostic value of vascular endothelial growth factor and its receptor Flt-1 in squamous cell lung cancer," International Journal of Cancer. Journal International DU Cancer Feb. 20, 1997, vol. 74, No. 1, Feb. 20, 1997, pp. 64-68, XP 002431300.
European Search Report dated May 14, 2007.
Dennis A. Wigle, et al., "Molecular Profiling of Non-Small Cell Lung Cancer and Correlation with Disease-free Survival", Cancer Research, vol. 62, pp. 3005-3008, Jun. 1, 2002.
Ganbunshi Hyouteki Chiryou, vol. 1, No. 1, pp. 72-77, Jan. 30, 2003.
T.R. Golub, et al., "Molecular Classification of Cancer: Class Discovery and Class Prediction by Gene Expression Monitoring", Science, vol. 286, pp. 531-537, Oct. 15, 1999.
Japanese Office Action dated May 19, 2009 in JP 2003-415,119.

* cited by examiner

*Primary Examiner*—Mary K Zeman
(74) *Attorney, Agent, or Firm*—Sughrue Mion, PLLC

(57) ABSTRACT

The present invention provides a method of confirming the gene expression, useful in the decision of a five year survival rate of a patient with lung cancer and the use of a DNA probe kit in the method.

A method useful in the decision of a survival rate of a patient with non-small cell lung cancer comprising confirming the expression strength of at least one gene selected from the group consisting of
in lung cancer tissues isolated from the patient.

1 Claim, 6 Drawing Sheets

METHOD OF CLASSIFYING GENE EXPRESSION STRENGTH IN LUNG CANCER TISSUES

TECHNICAL FIELD

The present invention relates to a method of confirming the expression of a specific gene in lung cancer tissues, used in a technique of predicting a five year survival rate of a patient with lung cancer with high accuracy.

BACKGROUND OF THE INVENTION

When various therapies are applied to patients with cancer (carcinoma), a five year survival rate is often used as a measure of cure. That is, a five year survival rate is a probability that a patient who underwent a cancer diagnosis or therapy will be survival over five years thereafter. By this probability, a progressive level (stage) of cancer, a therapeutic effect and the like are represented.

Until now, the TNM classification comprising the combination of the size of tumor (tumor meter, represented by T), the range where metastasis to lymphonodi are observed (represented by N) and the presence or absence of distant metastasis (represented by M), each of which is determined by clinical method, has been mainly used ("Cancer of the lung", written by Robert Ginsberg et al., 5th edition, pp. 858 to 910, Lippincott-Raven (1997)). For example, patients judged to be in stage I under the TNM classification means those having a progressive level such that a little over 60% of the patients could be survival for five years if cancer is resected by surgery. Patients judged to be in stage III means those having a progressive level such that at most 20% the patients could be survival even under the same condition.

Recently, focusing on one or two genes specifically expressed in cancer patients or cancer tissues, a therapeutic effect is often predicted by determining the difference in the expression of said gene(s) between patients showing superior therapeutic effect and patients showing poor therapeutic effect (Horio et al, Cancer Research, Vol. 54, pp. 1 to 4, Jan. 1, 1993).

SUMMARY OF THE INVENTION

However, the TNM classification cannot be applied unless outcomes of many clinical tests are accumulated. Thus, this classification is not be said to be simple and its accuracy is not satisfactory at all. And, in a method of predicting a therapeutic effect by confirming the expression of a specific gene, the correlation between the gene expression in patients with lung cancer and a five year survival rate of the patients has not been reported.

An object of the present invention is to accurately decide a survival rate of patients especially with lung cancer. In the present invention, the expression of a specific gene in lung cancer tissues is confirmed.

Accordingly, the present invention relates to a method useful in the decision of a survival rate of a patient with non-small cell lung cancer comprising confirming the expression strength of at least one gene selected from the group consisting of WEE1 (AA039640), MYC (AA464600), TITF1 (T60168), FOSL1 (T82817), LYPLA1 (H00817), SSBP1 (R05693), SFTPC (AA487571), THBD (H59861), NICE-4 (AA054954), PTN (AA001449), SNRPB (AA599116), NAP1L1 (R93829), CTNND1 (AA024656), CCT3 (R60933), DSC2 (AA074677), SPRR1B (AA447835), COPB (AA598868), ARG1 (AA453673), ARCN1 (AA598401), MST1 (T47813), SERPINE1 (N75719), SERPINB1 (AA486275), EST fragment (N73201), ACTR3 (N34974), PTP4A3 (AA039851), ISLR (1462387), ANXA1 (1163077), GJA1 (AA487623), HSPE1 (AA448396) and PSMA5 (AA598815) in lung cancer tissues isolated from the patient.

And, the present invention provides a method useful in the decision of a survival rate of a patient with squamous cell lung cancer comprising confirming the expression strength of at least one gene selected from the group consisting of FLJ20619 (R74480), SPC12 (R19183), EST fragment (R96358), KRT5 (AA160507), PTP4A3 (AA039851), SPRR1B (AA447835), LOC339324 (W23522), MYST4 (AA057313), SPARCL1 (AA490694), IGJ (T70057), EIF4A2 (H05919), EST fragment (AA115121), ID2 (H82706), THBD (H59861), MGC15476 (W72525), ZFP (H53499), COPB (AA598868), ZYG (AA453289), CACNA1I (N52765), FLJ4623 (N71473), CSTB (H22919), EPB41L1 (R71689), MGC4549 (AA455267), EST fragment (T64878), DSC2 (AA074677), EST fragment (H79007), EST fragment (W84776), IFI30 (AA630800), EST fragment (T81155) and IL1RN (T72877) in lung cancer tissues isolated from the patient.

Further, the present invention provides a method useful in the decision of the survival rate of a patient with non-squamous cell lung cancer comprising confirming the expression strength of at least one gene selected from the group consisting of NICE-4 (AA054954), WEE1 (AA039640), SSBP1 (R05693), WFDC2 (AA451904), ACTA2 (AA634006), G22P1 (AA486311), MST1 (T47813), PHB (R60946), DRPLA (H08642), SNRBP (AA599116), GJA1 (AA487623), SFTPC (AA487571), ACTR1A (R40850), MYC (AA464600), RAD23B (AA489678), CCT3 (R60933), SERPINE1 (N75719), LAMP1 (H29077), IRAK1 (AA683550), BIRC2 (R19628), LMAN1 (H73420), HSPE1 (AA448396), TMSB4X (AA634103), EEF1G (R43973), EST fragment (H05820), LYPLA1 (H00817), SOD1 (R52548), ARG1 (AA453673), KRT25A (W73634) and FOSL1 (T82817) in lung cancer tissues isolated from the patient.

Another aspect of the present invention relates to the use in the above method of a DNA probe comprising a nucleic acid sequence specifically hybridizing to at least one gene targeted in this method.

All genes which expression is to be confirmed in the present invention are known genes. The nucleotide sequence of each gene is registered in "UniGene", one of the public databases provided by NCBI, with its abbreviated name and its accession number represented by the combination of alphabet (such as AA) and numeral. In the present specification including claims, all of the genes to be confirmed in the method of the present invention are represented with the abbreviated names and the accession numbers registered in "UniGene" on Nov. 19, 2003. Since a gene can be specified with the abbreviated name and the accession number registered in "UniGene", those skilled in the art easily confirm a gene in question and its detailed nucleotide sequence by referring to "UniGene" and conduct the present invention. Similarly, as to a nucleic acid sequence of a DMA prove specific for each gene used in the method of the present invention, those skilled in the art can easily determine some candidate sequences for each gene based on the nucleic acid sequence registered in the above database using a homology searching program or the like. Especially, the nucleic acid sequence of the probe of the present invention is not limited unless it is selected such that the probe can be specifically hybridized to a gene corresponding therefor. It is not necessarily to restrict or limit to one nucleic acid sequence. Such a procedure can be made by those skilled in the art without having a need of any specific effort.

The present inventors studied to search for genes specifically expressed in lung cancer tissues of patients who were underwent non-small cell lung cancer diagnosis or therapy and who were dead within five years thereafter or survival over five or more years thereafter. As the result, they found that there is a specific tendency between a five year survival rate and a gene expression pattern.

Focusing on genes whose expression amounts were specifically increased or decreased in cancer tissues of the group of patients who were dead within five years after operation or diagnosis as compared with the group of patients who were survival over five years after operation or diagnosis, the present inventors selected predictive genes capable of distinguishing both groups efficiently using a signal-to-noise metrics (Golub et al., Science, Vol. 286, pp. 531 to 537 (1999)). Briefly, if a prognosis favorable patient and a prognosis fatal patient are defined to belong to class 0 and class 1 respectively, a signal-to-noise statistic (Sx) for gene x is calculated as follows:

$$Sx = (\mu class\ 0 - \mu class\ 1/\delta class\ 0 + \delta class\ 1)$$

As to each gene, $\mu$class 0 means an average of data on total expression strength of patients belonging to class 0 (a group of prognosis favorable patients) and $\delta$class 0 means a standard deviation of data on total expression strength of patients belonging to class 0 (a group of prognosis favorable patients) Using the thus-calculated absolute value of Sx, genes ranked higher, i.e. genes showing a significant difference in expression strength between the group of prognosis favorable patients and the group of prognosis fatal patients, were selected.

In order to assay a statistical significance of a marker gene specific for a different type of cancer, a sample level (prognosis favorable or fatal) of each patient used in the analysis in association with a set of data on gene expression strength were randomly labeled and then the signal-to-noise value (Sx value) was recalculated in accordance with the labels after randomizing. This procedure was repeated 10,000 times. P values were assigned to every genes based on the extent so that Sx value obtained by randomizing the labels was better than Sx value obtained actually.

When genes to be judged that they are significantly related to a survival rate of patients with a different type of lung cancer, i.e. predictive genes, were searched for among genes expressed in cancer tissues of the patients, the following correlation became clear.

Thus, an expression pattern such that in many lung cancer tissues of patients who were underwent non-small cell lung cancer diagnosis or therapy and dead within five years thereafter, the expression of each of WEE1 (AA039640), MYC (AA464600), FOSL1 (T82817), LYPLA1 (H00817), SSBP1 (R05693), THBD (H59861), NICE-4 (AR054954), PTN (AA001449), SNRPB (AA599116), NAP1L1 (R93829), CTNND1 (AA024656), CCT3 (RG0933), DSC2 (RA074677), SPRR1B (AA447835), COPB (AA598868), ARG (AA453673), ARCN1 (AA598401), MST1 (T47813), SERPINE1 (N75719), SERPINB1 (AA486275), ACTR3 (N34974), PTP4A3 (AA039851), ISLR (H623B7), ANXA1 (163077), GJA1 (AA487623), BSPE1 (AA448396) and PSEA5 (AA598815) was significantly increased and the expression of each of TITF1 (T60168), SFTPC (AA487571) and EST fragment (N73201) was significantly lowered was observed. Hereinafter, the group comprising the above genes is referred to be a gene group 1.

Accordingly, by extracting total RNAs from cancer tissues of a patient who was underwent a non-small cell lung cancer diagnosis and confirming the expression strength of at least one gene belonging to the gene group 1, it is possible to predict a five year survival rate of the patient whether the patient would be dead within five years or survival over five or more years.

For example, when PTP4A3 (AA039851, fatal) is selected as a gene and a five year survival rate is predicted based on the outcome obtained by confirming the expression strength of this gene, an accuracy of 64% can be expected. When WEE1 (AA039640, fatal) or ACTR3 (N34974, fatal) is selected as a gene in addition to PTP4A3 (AA039851, fatal) and a five year survival rate is predicted based on the outcomes obtained by confirming the expression strength of these genes, an accuracy will be 66% or 74%. And, based on the outcomes obtained by confirming the expression strength of all genes constituting the gene group 1, an accuracy will reach 82%. The above outcomes have reliability higher than that of the prior method.

Although non-small cell lung cancer is further classified squamous cell cancer (SQ) and non-squamous cell cancer (non-SQ), the gene group 1 is useful as a gene group selected when a five year survival rate is decided without subdividing the type of lung cancer cells.

On the other hand, the present inventors confirmed the gene expression strength for squamous cell cancer (SQ) and non-squamous cell cancer (non-SQ) and as the result, they found that a five year survival rate can be decided more accurately by using a gene group different from the gene group 1 as targets.

Thus, an expression pattern such that in many lung cancer tissues of patients who were underwent squamous cell cancer diagnosis of therapy and dead within five years thereafter, the expression of each of KRT5 (AA160507), PTP4A3 (AA039851), SPRR1B (AA447835), MYST4 (AA057313), SPARCL1 (AA490694), IGJ (T70057), EST fragment (AA115121), ID2 (H82706), THBD (H59861), MGC15476 (W72525), COPB (AA598868), ZYG (AA453289), CACNA1I (N52765), CSTB (H22919), EPB41L1 (R71689), MGC4549 (AA455267), DSC2 (AA074677), IFI30 (AA630800), EST fragment (T81155) and IL1RN (T72877) was significantly increased and the expression of each of FLJ20619 (R74480), SPC12 (R19183), EST fragment (R96358), LOC339324 (W23522), EIF4A2 (H05919), ZFP (H53499), FLJ4623 (N71473), EST fragment (T64878), EST fragment (H79007) and EST fragment (W84776) was significantly lowered was observed. Hereinafter, the group comprising the above genes is referred to be a gene group 2.

Accordingly, by extracting total RNAs from cancer tissues of a patient who was underwent a squamous cell cancer diagnosis and confirming the expression strength of at least one gene belonging to the gene group 2, it is possible to predict a five year survival rate of the patient whether the patient would be dead within five years or survival over five or more years.

For example, when CACNAII (N52765, fatal) is selected as a gene and a five year survival rate is predicted based on the outcome obtained by confirming the expression strength of this gene, an accuracy of 81% can be expected. When FLJ20619 (R74480, favorable) is selected as a gene in addition to CACNAII (N52765, fatal) and a five year survival rate is predicted based on the outcomes obtained by confirming the expression strength of these genes, an accuracy will be 75% or 81%. And, based on the outcomes obtained by confirming the expression strength of all genes constituting the gene group 2, an accuracy will reach 100%.

And, an expression pattern such that in many lung cancer tissues of patients who were underwent non-squamous cell cancer diagnosis or therapy and dead within five years thereafter, the expression of each of NICE-4 (AA054954), WEE1 (AA039640), SSBP1 (R05693), G22P1 (AA486311), MST1 (T47813), PHB (R60946), DRPLA (H08642), SNRPB (AA599116), GJA1 (AA487623), ACTR1A (R40850), MYC (AA464600), RAD23B (AA489678), CCT3 (R60933), SERPINE1 (N75719), BIRC2 (R19628), LMAN1 (H73420), HSPE1 (AA448396), EEF1G (R43973), EST fragment (H05820), LYPLA1 (H00817), SOD1 (R52548), ARG1 (AA453673), KRT25A (W73634) and FOSL1 (T82817) was significantly increased and the expression of each of WFDC2 (AA451904), ACTA2 (AA634006), SFTPC (AA487571), LAMP1 (H29077), IRAK1 (AA683550) and TMSB4X (AA634103) was significantly lowered was observed. Hereinafter, the group comprising the above genes is referred to be a gene group 3.

Accordingly, by extracting total RNAs from cancer tissues of a patient who was underwent a non-squamous cell cancer and confirming the expression strength of at least one gene belonging to the gene group 3, it is possible to predict a five year survival rate of the patient whether the patient would be dead within five years or survival over five or more years.

For example, when SFTPC (AA487571, favorable) is selected as a gene and a five year survival rate is predicted based on the outcome obtained by confirming the expression strength of this gene, an accuracy of 56% can be expected. When NICE-4 (AA054954, fatal) or GJA1 (AA487623, fatal) is selected as a gene in addition to SFTPC (AA487571, favorable) and a five year survival rate is predicted based on the outcomes obtained by the expression strength of these genes, an accuracy will be 79% or 76%. And, based on the outcomes obtained by the expression strength of all genes constituting the gene group 3, an accuracy will reach 91%.

As mentioned above, it is preferable to select two or more genes, more preferably all genes belonging to each gene group as targets although only one gene may be freely selected from each gene group and used it.

Further, the present invention provides information about samples γ obtained from cancer tissues of new patients for deciding whether the patients will be survival or dead based on the above correlation.

In order to decide whether new patients with lung cancer (test samples γ) will be prognostic favorable or fatal after five years, Vx may be calculated for each gene contained in a set of predictive genes from the equation: $Vx=Sx(Gx^γ-bx)$ wherein Sx is the above-mentioned signal-to-noise statistic; $Gx^γ$ represents the expression strength of each gene x contained in the set of predictive genes; and bx is calculated from the equation: $bx=(μclass\ 0+μclass\ 1)/2$. When the sum of Vx (ΣVx) for the genes contained in the set of predictive genes is calculated to be plus (+), the patient in question is decided to be "prognosis favorable". When ΣVx is calculated to be minus (−), the patient in question is decided to be "prognosis fatal".

EFFECT OF THE INVENTION

Figure 1:
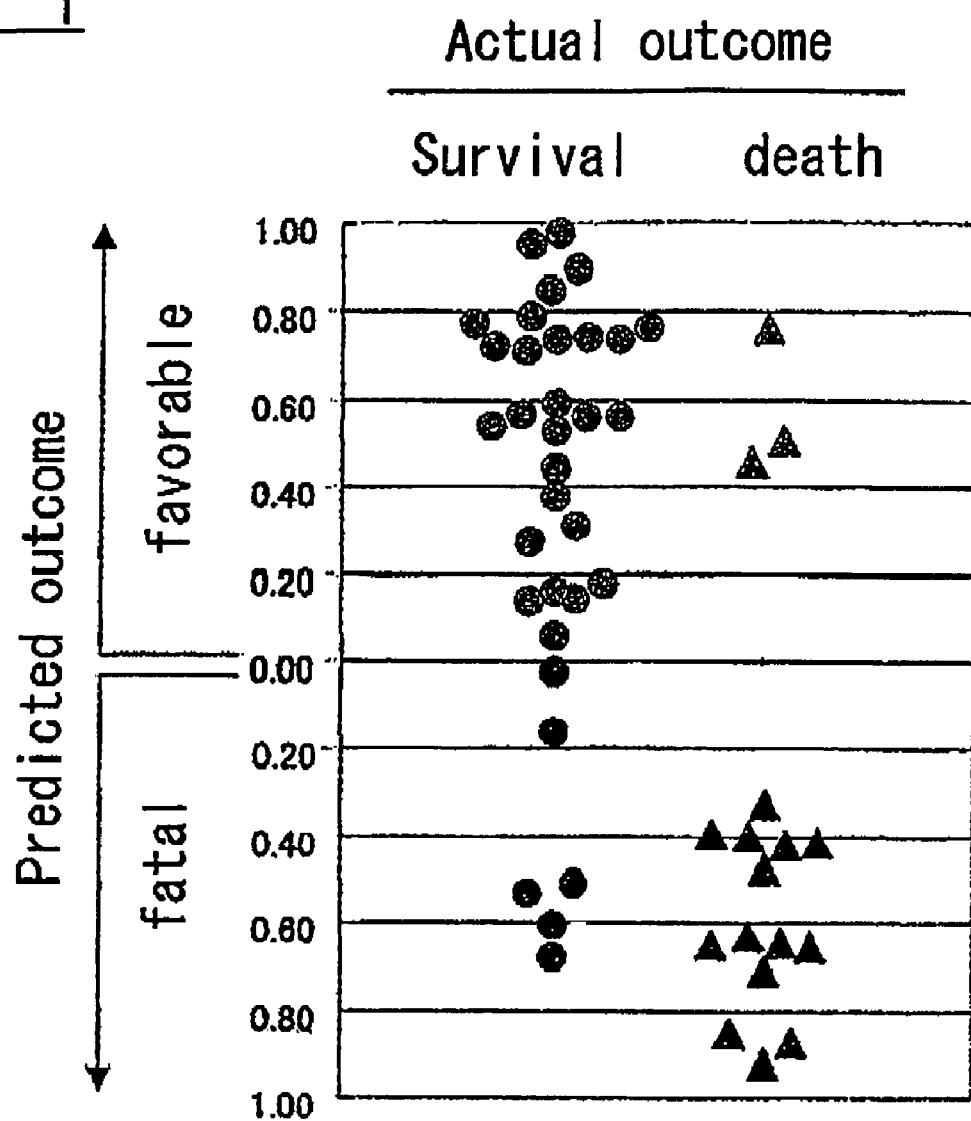
FIG. 1 represents the outcomes obtained by predicting patients with non-squamous cell lung cancer using 25 predictive genes in a weighted-voting model.

By using the method of the present invention, a five year survival rate of patients with lung cancer can be predicted with high accuracy. Therefore, it is possible according to the present invention to predict whether or not a patient with a different type of lung cancer could be survival over five or more years with high accuracy by confirming that a specified gene group is expressed in cancer tissues of the patient.

DISCLOSURE OF THE INVENTION

Expression strength of each gene belonging to the gene group specified in the present invention can be confirmed by providing a specific probe every nucleotide sequence and conducting PCR or hybridization. The nucleotide sequence of each gene can be easily confirmed from the database "UniGene". And, conditions such as the design of a probe specifically hybridizing to each gene, its synthesis, hybridization and the like can be suitably determined by those skilled in the art without having a need of any specific effort.

The probe can be synthesized as a set of probes capable of subjecting to PCR reaction for each gene, i.e. PCR primers. The expression strength may be confirmed by conducting PCR reaction using these primers.

Upon practice of the present method, the expression of a gene is preferably confirmed in the so-called microarray. As an microarray, a glass substrate on which probe DNAs are spotted; a membrane on which probe DNAs are spotted; beads on which probe DNAs are spotted; a glass substrate on which probes are directly synthesized; and the like have been developed. Examples of the microarray include a membrane microarray available from Invitrogen (GeneFilters™, Mammalian Microarrays; Catalog # GF200 or GF201). This membrane microarray contains 11168 spots in total of probe DNA corresponding to 8644 independent genes. It is confirmed by Blast search that the sequence of each probe does not occur the so-called cross hybridization even when gene(s) closely related to each sequence is(are) present, otherwise the expression of such gene(s) is detected erroneously.

Examples of the microarray available in the present invention include cDNA or oligo-arrays available from Affimetrix, Agilent and other companies, in addition to the membrane microarray available from Invitrogen.

It is desirable in the present invention to immediately frozen cancer tissues isolated from a patient with lung cancer during thoractomy or by biopsy with an endoscope or the like to prepare a slice, prepare a tissue section by hollowing out minutely regions rich in cancer cells in the slice, extract RNAs from the tissue section according to any standard method and transform all mRNAs expressed in the tissue into a cDNA by acting a reverse transcriptase thereto. In this case, the targeted gene group can be labeled by adding to the cDNA a suitable radioisotope such as $^{33}P$ and the like or a fluorochrome such as Cy3, Cy5 and the like during the preparation of the cDNA via the reaction with a reverse transcriptase.

According to the present invention, based on the information about the nucleotide sequence of the gene contained in each gene group, the expression strength of the gene to be detected can be confirmed by hybridization or real time PCR using an oligo DNA specific for each gene to be detected. Preferably the expression of each gene group to be detected is confirmed more easily by combining cDNAs prepared with a reverse transcriptase and a suitable label with a microarray.

The expression strength of a gene group targeted in the present invention can be confirmed easily by hybridizing a labeled cDNA and a microarray under suitable conditions and then confirming the expression of the genes and their amounts as an index of the label. The expression strength is confirmed by quantifying the strength of a signal produced from the label by a suitable method.

For example, when a radioactive label is used, a signal strength can be quantified by exposing a hybridized array to an imaging plate (Fuji Photo Film), scanning and imaging using a bioimaging analyzer BAS 5000 (Fuji Photo Film), processing images of the hybridized array using L Process (Fuji Photo Film) and then analyzing using an analytical soft Array Gauge (Fuji Photo Film). Alternatively, the strength of a radioactive label can be quantified using a phospho-imager (Amersham). And, the strength of a fluorescent label can be quantified using a microarray reader (Agilent) or the like.

The thus-obtained data on label strength are converted to data on hybridization strength, respectively by using, for example, the method of Tseng et al. (Nucleic Acids Res., Vol., 29, pp. 2549 to 2557). Thereafter, a reproducibility in expression is evaluated after normalization, preparation of scatter plots for each gene and the like. Thus, a significant increase or decrease in expression amount of a targeted gene may be evaluated.

EXAMPLES

The present invention will be described in more detail by referring to the following examples which are not to be construed as limiting the scope of the invention.

Example 1

In the following example, all procedures using commercially available kits were conducted under conditions as recommended by the manufactures unless otherwise stated.

1) Extraction of Total RNAs from Lung Cancer Tissue

From each of 50 patients (15 females and 35 males; between the ages of 43 and 76, average age of 63) with non-small cell lung cancer, specifically 30 patients with glandular lung cancer, 16 patients with squamous cell lung cancer and 4 patients with large cell lung cancer (23 patients with stage I, 11 patients with stage II and 16 patients with stage III), lung cancer tissues (0.5 g in average) were isolated. The tissues were embedded in OCT compound and frozen at −80° C., thereby a frozen sample of 7 μm in thickness was prepared. Then, a region rich in cancer cells was carefully excised from the sample to obtain a section having cancer cells accounted for 75.4% in average of cells contained therein. From this section, total RNAs (12 μg in average) were extracted using RNAeasy (Quiagen) and a purity thereof was confirmed using RNA 600 nanoassay kit and 2100 Bioanalyzer (Agilent).

2) Hybridization to Microarray 5 micrograms of the total RNAs as prepared in the above 1) was transformed into cDNA using oligo-dT primer (Invitrogen) and Superscript II reverse transcriptase (Invitrogen) by adding 10 μCi of [$^{32}$P]dCTP. GeneFilters (Invitrogen) was prehybridized in 10 ml of AlkPhos DIRECT hybridization buffer (Amersham) containing 0.5 μg/ml of poly-dA (Invitrogen) and 0.5 μg/ml of Cot-1 DNA (Invitrogen) at 51° C. for 2 hours and then hybridized with a modified radiolabeled probe cDNA for 17 hours.

After hybridizing, the microarray was washed with a solution containing 2M urea, 0.1% SDS, 50 mM sodium phosphate buffer solution (pH7.0), 150 mM NaCl, 1 mM MgCl$_2$ and 0.2% AlkPhos DIRECT blocking reagent (Amersham) twice, a solution containing 2 mM MgCl$_2$, 50 mM Tris and 100 mM NaCl twice and a solution containing 2 mM MgCl$_2$, 50 mM Tris and 15 mM NaCl twice successively. The microarray was exposed to an imaging plate (Fuji Photo Film) for 2 hours and then the imaging plate was scanned and imaged using a bioimaging analyzer BAS 5000 (Fuji Photo Film) with resolution of 25 μm. The image of the hybridized array was processed with L Process (Fuji Photo Film) and then a signal strength was quantified using an analytical soft Array Gauge (Fuji Photo Film).

3) Data Processing

The data on signal strength obtained in the above 2) was converted to data on hybridization strength, respectively. First, the method of Tseng et al. (Nucleic Acids Res., Vol. 29, pp. 2549 to 2557) was employed for selecting genes used in the fitting of a non-linear normalization curve. After normalization, scatter plots of 50 sets of replication data on each gene were prepared and a reproducibility of expression between replication pairs was evaluated. Genes showing a Pearson correlation coefficient of 0.85 or higher were selected. An average of the first hybridization and the second hybridization was used for further analysis. In addition, genes not showing a double or half change at at least an expression level were excluded. Genes having a median intensity of less than 0.3 were excluded from the following analysis.

4) Isolation of Gene for Five Year Survival

Predictive genes distinguishing patients who would be dead within five years after operation or diagnosis (prognosis fatal patients) and patients who would be survival over five years after operation or diagnosis (prognosis favorable patients) most efficiently were selected using a signal-to noise metrics (Golub et al., Science, Vol. 286, pp. 531 to 537 (1999)). Briefly, if a prognosis favorable patient and a prognosis fatal patient are defined to belong to class 0 and class 1 respectively, a signal-to-noise statistic (Sx) is calculated as follows:

$$Sx=(\mu\text{class }0-\mu\text{class }1/\delta\text{class }0+\delta\text{class }1)$$

As to each gene, μclass 0 means an average of data on total expression strength of patients belonging to class 0 (the group of prognosis favorable patients) and δclass 0 means a standard deviation of data on total expression strength of patients belonging to class 0 (the group of prognosis favorable patients).

Genes ranked higher based on the absolute value of Sx were selected. In order to predict the outcomes using the thus-selected genes, a weighted-voting classification algorithm was employed. The thus-obtained outcome classifiers were tested using a leave-one-out cross validation. In this scheme, the algorithm can be employed to find decision boundaries between class average and bx=(μclass 0+μclass 1)/2 for each gene, in addition to the calculation of Sx.

5) Permutation Test

In order to assay a statistical significance of a marker gene specific for a different type of cancer, a sample level (survival or dead) of each patient used in the analysis together with a set of data on gene expression strength were labeled randomly and then the signal-to-noise value (Sx value) for each gene was recalculated in accordance with the labels after randomizing. This procedure was repeated 10,000 times. P values were assigned to every genes based on the extent so that Sx value obtained by randomizing the labels was better than Sx value obtained actually.

6) Construction of Model Predicting Survival Rate of Patients with Non-Small Cell Cancer In order to develop an outcome prediction classifier of each patient, a signal-to-noise metrics was employed for selecting a gene distinguishing prognosis favorable patients from prognosis fatal patients most clearly. As the outcomes of a non-supervised hierarchical clustering algorithm using spots ranked top 100 corresponding to unique 98 genes, two major branches representing prognosis favorable patients and prognosis fatal patients were obtained. Among 21 patients with non-small cell cancer, 19 patients (left frame), i.e. the favorable branch, were survival over five years after operation. On the other hand, among 29 patients with non-small cell cancer, 15 patients (right frame), i.e. the fatal branch, were dead within five years after operation. The Kaplan-Meier survival curve reveals statistically significant difference.

Since our final goal was to develop outcome classifiers at patient level, a supervised learning method was employed. Thus, weighted-voting outcome classifiers were constructed based on the predictive genes preselected using the signal-to-noise metrics. A learning error against each model while increasing the number of predictive genes used was calculated by a leave-one-out cross validation. Among 30 genes constituting the outcome classifiers for non-small cell cancer (Table 1), the weighted-voting model using 25 predictive genes ranked top 25 revealed the highest accuracy such that 41 patients (82%) of 50 patients revealed the outcomes as predicted individually (FIG. 1).

TABLE 1

Non-small cell cancer

| Rank | Gene | Description | accession No. | expression in lung cancer | P | bx | Sx | SEQ ID NO. |
|---|---|---|---|---|---|---|---|---|
| 1 | WEE1 | WEE1 homolog | AA039640 | Up | 0.0027 | 0.483 | 0.483 | SEQ ID NO: 1 |
| 2 | MYC | v-myc viral oncogene homolog | AA464600 | Up | 0.0057 | 0.479 | 0.441 | SEQ ID NO: 2 |
| 3 | TITF1 | thyroid transcription factor 1 | T60168 | Down | 0.0085 | 0.452 | 0.416 | SEQ ID NO: 3 |
| 4 | FOSL1 | FOS-like antigen 1 (Fra-1) | T82817 | Up | 0.0062 | 0.330 | 0.411 | SEQ ID NO: 4 |
| 5 | LYPLA1 | lysophospholipase I | H00817 | Up | 0.0081 | 0.460 | 0.408 | SEQ ID NO: 5 |
| 6 | SSBP1 | single-stranded DNA binding protein | R05693 | Up | 0.0199 | 0.495 | 0.406 | SEQ ID NO: 6 |
| 7 | SFTPC | surfactant, pulmonary-associated protein C | AA487571 | Down | 0.0113 | 0.322 | 0.405 | SEQ ID NO: 7 |
| 8 | THBD | thrombomodulin | H59861 | Up | 0.0099 | 0.466 | 0.403 | SEQ ID NO: 8 |
| 9 | NICE-4 | NICE-4 protein | AA054954 | Up | 0.0099 | 0.514 | 0.403 | SEQ ID NO: 9 |
| 10 | PTN | pleiotrophin (heparin binding growth factor 8) | AA001449 | Up | 0.0100 | 0.500 | 0.401 | SEQ ID NO: 10 |
| 11 | SNRPB | small nuclear ribonucleoprotein polypeptides B and B1 | AA599116 | Up | 0.0115 | 0.657 | 0.394 | SEQ ID NO: 11 |
| 13 | CTNND1 | catenin delta 1 | R93829 | Up | 0.0120 | 0.513 | 0.393 | SEQ ID NO: 12 |
| 12 | NAPIL1 | nucleosome assembly protein 1-like 1 | AA024656 | Up | 0.0131 | 0.483 | 0.384 | SEQ ID NO: 13 |
| 14 | CCT3 | chaperonin containing TCP1, subunit 3 | R60933 | Up | 0.0186 | 0.566 | 0.378 | SEQ ID NO: 14 |
| 15 | DSC2 | desmocollin 2 | AA074677 | Up | 0.0160 | 0.533 | 0.374 | SEQ ID NO: 15 |
| 16 | SPRR1B | small proline-rich protein 1B (cornifin) | AA447835 | Up | 0.0209 | 0.421 | 0.370 | SEQ ID NO: 16 |
| 17 | COPB | coatomer protein complex, subunit beta | AA598868 | Up | 0.0195 | 0.466 | 0.369 | SEQ ID NO: 17 |
| 18 | ARG1 | arginase type I (liver) | AA453673 | Up | 0.0193 | 0.581 | 0.369 | SEQ ID NO: 18 |
| 19 | ARCN1 | archain 1 (coatomer protein complex, subunit delta) | AA598401 | Up | 0.0169 | 0.412 | 0.367 | SEQ ID NO: 19 |
| 20 | MST1 | macrophage stimulating 1 | T47813 | Up | 0.0193 | 0.462 | 0.366 | SEQ ID NO: 20 |
| 21 | SERPINE1 | serine (or cysteine) proteinase inhibitor, clade E member 1 | N75719 | Up | 0.0194 | 0.495 | 0.366 | SEQ ID NO: 21 |
| 22 | SERPINB1 | serine (or cysteine) proteinase inhibitor, clade B member 1 | AA486275 | Up | 0.0205 | 0.556 | 0.362 | SEQ ID NO: 22 |
| 23 | ESTs | | N73201 | Down | 0.0205 | 0.494 | 0.360 | SEQ ID NO: 23 |
| 24 | ACTR3 | actin-related protein 3 homolog (ARP3) | N34974 | Up | 0.0229 | 0.496 | 0.358 | SEQ ID NO: 24 |
| 25 | PTP4A3 | protein tyrosine phosphatase type 4A, member 3 | AA039851 | Up | 0.0199 | 0.478 | 0.357 | SEQ ID NO: 25 |
| 26 | ISLR | immunoglobulin superfamily containing leucine-rich repeat | H62387 | Up | 0.0228 | 0.478 | 0.356 | SEQ ID NO: 26 |
| 27 | ANXA1 | annexin A1 | H63077 | Up | 0.0262 | 0.367 | 0.354 | SEQ ID NO: 27 |
| 28 | GJA1 | gap junction protein, alpha 1 | AA487623 | Up | 0.0230 | 0.406 | 0.354 | SEQ ID NO: 28 |
| 29 | HSPE1 | heat shock 10 kD protein 1 | AA448396 | Up | 0.0273 | 0.444 | 0.352 | SEQ ID NO: 29 |
| 30 | PSMA5 | proteasome (prosome, macropain) subunit, alpha type, 5 | AA598815 | Up | 0.0265 | 0.545 | 0.346 | SEQ ID NO: 30 |

Figure 2:
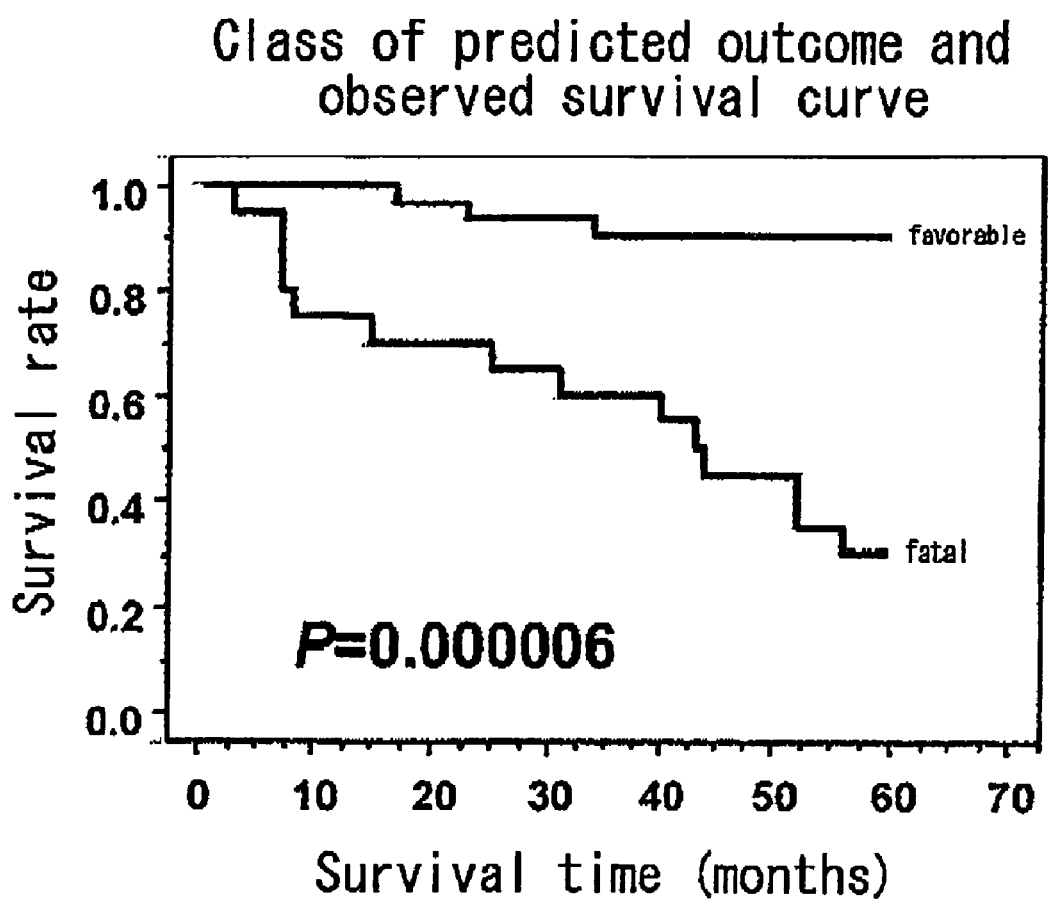
FIG. 2 is a survival curve showing the prognosis "favorable" or "fatal" of patients with non-small cell lung cancer.

As to these classifiers, 27 patients of 33 patients (82%) practically survival over five or more years after operation were decided to be "prognosis favorable" and 14 patients of 17 patients (82%) practically dead within five years after operation were decided to be "prognosis fatal". A survival curve of patients for the prediction of "prognosis favorable" or "prognosis fatal" is shown in FIG. 2. This figure reveals the difference between two groups ($P=6.0\times10^{-6}$).

With the increase in the number of the above genes, another supervised learning algorithm including Support vector machine and k-nearest neighbors was employed. The accuracy of the model is comparable with that of the weighted-voting outcome classifiers, but the latter showed the highest accuracy.

In order to decide whether new patients with lung cancer (test samples γ) could be prognosis favorable or fatal after five years, Vx may be calculated for each gene contained in the set of predictive genes from the equation: $Vx=Sx(Gx^\gamma-bx)$ wherein Sx is the above-mentioned signal-to-noise statistic; $Gx^\gamma$ represents an expression strength of each gene x contained in the set of predictive genes; and bx is calculated from bx=(μclass 0+μclass 1)/2. When the sum of Vx (ΣVx) for genes contained in the set of predictive genes is calculated to be plus (+), the patient in question is decided to be "prognosis favorable". When ΣVx is calculated to be minus (−), the patient in question is decided to be "prognosis fatal".

With the increase in the number of the above genes, another supervised learning algorithm including Support vector machine and k-nearest neighbors was employed. The accuracy of the model is comparable with that of the weighted-voting outcome classifiers, but the latter showed the highest accuracy.

7) Construction of Model Predicting Survival Rate Specific for Each of Squamous Cell Cancer and Non-Squamous Cell Cancer Squamous cell cancer and non-squamous cell cancer are recognized as diseases distinguishable clinicopathologically each other. Thus, using predictive genes for each subtype selected with the weighted-voting algorithm and the signal-to-noise metrics, outcome prediction classifiers for a different type of cancer were constructed.

Among 30 genes constituting the outcome classifiers for a different type of cancer (Tables 2 and 3), 12 genes (Table 2) for non-squamous cell cancer and 19 genes (Table 3) for squamous cell cancer revealed the highest accuracy by a leave-one-out cross validation including the increase in the number of predictive genes ranked higher.

TABLE 2

Non-squamous cell cancer

| Rank | Gene | Description | accession No. | expression in lung cancer | P | bx | Sx | SEQ ID NO. |
|---|---|---|---|---|---|---|---|---|
| 1 | NICE-4 | NICE-4 protein | AA054954 | Up | 0.0036 | 0.567 | 0.604 | SEQ ID NO: 9 |
| 2 | WEE1 | WEE1 homolog | AA039640 | Up | 0.0039 | 0.485 | 0.567 | SEQ ID NO: 1 |
| 3 | SSBP1 | single-stranded DNA binding protein | R05693 | Up | 0.0122 | 0.466 | 0.500 | SEQ ID NO: 6 |
| 4 | WFDC2 | WAP four-disulfide core domain 2 | AA451904 | Down | 0.0155 | 0.544 | 0.489 | SEQ ID NO: 56 |
| 5 | ACTA2 | actin, alpha 2, smooth muscle, aorta | AA634006 | Down | 0.0149 | 0.684 | 0.487 | SEQ ID NO: 57 |
| 6 | G22P1 | thyroid autoantigen 70 kDa (Ku70) | AA486311 | Up | 0.0176 | 0.519 | 0.482 | SEQ ID NO: 58 |
| 7 | MST1 | macrophage stimulating 1 | T47813 | Up | 0.0153 | 0.462 | 0.481 | SEQ ID NO: 20 |
| 8 | PHB | prohibitin | R60946 | Up | 0.0219 | 0.419 | 0.472 | SEQ ID NO: 59 |
| 9 | DRPLA | dentatorubral-pallidoluysian atrophy | H08642 | Up | 0.0238 | 0.478 | 0.455 | SEQ ID NO: 60 |
| 10 | SNRPB | small nuclear ribonucleoprotein polypeptides B and B1 | AA599116 | Up | 0.0192 | 0.615 | 0.455 | SEQ ID NO: 11 |
| 11 | GJA1 | gap junction protein, alpha 1 | AA487623 | Up | 0.0268 | 0.332 | 0.446 | SEQ ID NO: 61 |
| 12 | SFTPC | surfactant, pulmonary-associated protein C | AA487571 | Down | 0.0313 | 0.350 | 0.445 | SEQ ID NO: 7 |
| 13 | ACTR1A | actin-related protein 1 homolog A | R40850 | Up | 0.0256 | 0.626 | 0.444 | SEQ ID NO: 62 |
| 14 | MYC | v-myc viral oncogene homolog | AA464600 | Up | 0.0294 | 0.385 | 0.434 | SEQ ID NO: 2 |
| 15 | RAD23B | RAD23 homolog B | AA489678 | Up | 0.0276 | 0.495 | 0.434 | SEQ ID NO: 63 |
| 16 | CCT3 | chaperonin containing TCP1, subunit 3 | R60933 | Up | 0.0305 | 0.548 | 0.431 | SEQ ID NO: 14 |
| 17 | SERPINE1 | serine (or cysteine) proteinase inhibitor, clade E member 1 | N75719 | Up | 0.0338 | 0.473 | 0.424 | SEQ ID NO: 21 |
| 18 | LAMP1 | lysosomal-associated membrane protein 1 | H29077 | Down | 0.0374 | 0.382 | 0.418 | SEQ ID NO: 64 |
| 19 | IRAK1 | interleukin-1 receptor-associated kinase 1 | AA683550 | Down | 0.0355 | 0.199 | 0.414 | SEQ ID NO: 65 |
| 20 | BIRC2 | baculoviral IAP repeat-containing 2 | R19628 | UP | 0.0362 | 0.359 | 0.412 | SEQ ID NO: 66 |
| 21 | LMAN1 | lectin, mannose-binding, 1 | H73420 | Up | 0.0339 | 0.409 | 0.411 | SEQ ID NO: 67 |
| 22 | HSPE1 | heat shock 10 kD protein 1 | AA448396 | Up | 0.0411 | 0.406 | 0.410 | SEQ ID NO: 68 |
| 23 | TMSB4X | thymosin, beta 4, X chromosome | AA634103 | Down | 0.0440 | 0.585 | 0.404 | SEQ ID NO: 69 |
| 24 | EEFIG | eukaryotic translation elongation factor 1 gamma | R43973 | Up | 0.0450 | 0.638 | 0.404 | SEQ ID NO: 70 |
| 25 | ESTs | | H05820 | Up | 0.0492 | 0.570 | 0.403 | SEQ ID NO: 71 |
| 26 | LYPLA1 | lysophospholipase I | H00817 | Up | 0.0488 | 0.456 | 0.401 | SEQ ID NO: 5 |
| 27 | SOD1 | superoxide dismutase 1 | R52548 | Up | 0.0477 | 0.609 | 0.397 | SEQ ID NO: 72 |
| 28 | ARG1 | arginase type I (liver) | AA453673 | Up | 0.0454 | 0.541 | 0.396 | SEQ ID NO: 18 |
| 29 | KRT25A | type I inner root sheath specific keratin 25 irs1 | W73634 | Up | 0.0534 | 0.584 | 0.394 | SEQ ID NO: 73 |
| 30 | FOSL1 | FOS-like antigen 1 (Fra-1) | T82817 | Up | 0.0366 | 0.309 | 0.391 | SEQ ID NO: 4 |

TABLE 3

Squamous cell cancer

| Rank | Gene | Description | accession No. | expression in lung cancer | P | bx | Sx | SEQ ID NO. |
|---|---|---|---|---|---|---|---|---|
| 1 | FLJ20619 | hypothetical protein | R74480 | Down | 0.0068 | 0.507 | 0.882 | SEQ ID NO: 31 |
| 2 | SPC12 | signal peptidase 12 kDa | R19183 | Down | 0.0087 | 0.521 | 0.859 | SEQ ID NO: 32 |
| 3 | ESTs | | R96358 | Down | 0.0034 | 0.448 | 0.835 | SEQ ID NO: 33 |
| 4 | KRT5 | keratin 5 | AA160507 | Up | 0.0046 | 0.841 | 0.789 | SEQ ID NO: 34 |
| 5 | PTP4A3 | protein tyrosine phosphatase type 4A, member 3 | AA039851 | Up | 0.0104 | 0.438 | 0.753 | SEQ ID NO: 25 |
| 6 | SPRR1B | small proline-rich protein 1B | AA447835 | Up | 0.0147 | 0.695 | 0.730 | SEQ ID NO: 16 |
| 7 | LOC339324 | hypothetical protein LOC339324 | W23522 | Down | 0.0171 | 0.536 | 0.693 | SEQ ID NO: 35 |
| 8 | MYST4 | MYST histone acetyltransferase 4 | AA057313 | Up | 0.0188 | 0.573 | 0.691 | SEQ ID NO: 36 |
| 9 | SPARCL1 | SPARC-like 1 | AA490694 | Up | 0.0210 | 0.454 | 0.682 | SEQ ID NO: 37 |
| 10 | IGJ | immunoglobulin J polypeptide | T70057 | Up | 0.0143 | 0.385 | 0.681 | SEQ ID NO: 38 |
| 11 | EIF4A2 | eukaryotic translation initiation factor 4A, isoform 2 | H05919 | Down | 0.0233 | 0.750 | 0.679 | SEQ ID NO: 39 |
| 12 | ESTs | | AA115121 | Up | 0.0226 | 0.412 | 0.672 | SEQ ID NO: 40 |
| 13 | ID2 | inhibitor of DNA binding 2 | H82706 | Up | 0.0214 | 0.608 | 0.670 | SEQ ID NO: 41 |
| 14 | THBD | thrombomodulin | H59861 | Up | 0.0077 | 0.636 | 0.669 | SEQ ID NO: 8 |
| 15 | MGC15476 | Thymus expressed gene 3-like | W72525 | Up | 0.0231 | 0.412 | 0.665 | SEQ ID NO: 42 |
| 16 | ZFP | zinc finger protein | H53499 | Down | 0.0217 | 0.632 | 0.659 | SEQ ID NO: 43 |
| 17 | COPB | coatomer protein complex, subunit beta | AA598868 | Up | 0.0272 | 0.527 | 0.648 | SEQ ID NO: 17 |
| 18 | ZYG | ZYG homolog | AA453289 | Up | 0.0237 | 0.349 | 0.647 | SEQ ID NO: 44 |

TABLE 3-continued

Squamous cell cancer

| Rank | Gene | Description | accession No. | expression in lung cancer | P | bx | Sx | SEQ ID NO. |
|---|---|---|---|---|---|---|---|---|
| 19 | CACNA11 | calcium channel, voltage-dependent, alpha 11 subunit | N52765 | Up | 0.0312 | 0.495 | 0.636 | SEQ ID NO: 45 |
| 20 | FLJ4623 | hypothetical protein | N71473 | Down | 0.0309 | 0.457 | 0.632 | SEQ ID NO: 46 |
| 21 | CSTB | cystatin B | H22919 | Up | 0.0286 | 0.762 | 0.631 | SEQ ID NO: 47 |
| 22 | EPB41L1 | erythrocyte membrane protein band 4.1-like 1 | R71689 | Up | 0.0482 | 0.690 | 0.613 | SEQ ID NO: 48 |
| 23 | MGC4549 | hypothetical protein | AA455267 | Up | 0.0327 | 0.410 | 0.606 | SEQ ID NO: 49 |
| 24 | ESTs | | T64878 | Down | 0.0406 | 0.457 | 0.600 | SEQ ID NO: 50 |
| 25 | DSC2 | desmocollin 2 | AA074677 | Up | 0.0407 | 0.656 | 0.592 | SEQ ID NO: 15 |
| 26 | ESTs | | H79007 | Down | 0.0415 | 0.363 | 0.590 | SEQ ID NO: 51 |
| 27 | ESTs | | W84776 | Down | 0.0364 | 0.665 | 0.587 | SEQ ID NO: 52 |
| 28 | IFI30 | interferon, gamma-inducible protein 30 | AA630800 | Up | 0.0415 | 0.336 | 0.587 | SEQ ID NO: 53 |
| 29 | ESTs | | T81155 | Up | 0.0552 | 0.633 | 0.583 | SEQ ID NO: 54 |
| 30 | IL1RN | interleukin 1 receptor antagonist | T72877 | Up | 0.0431 | 0.573 | 0.578 | SEQ ID NO: 55 |

Figure 3:
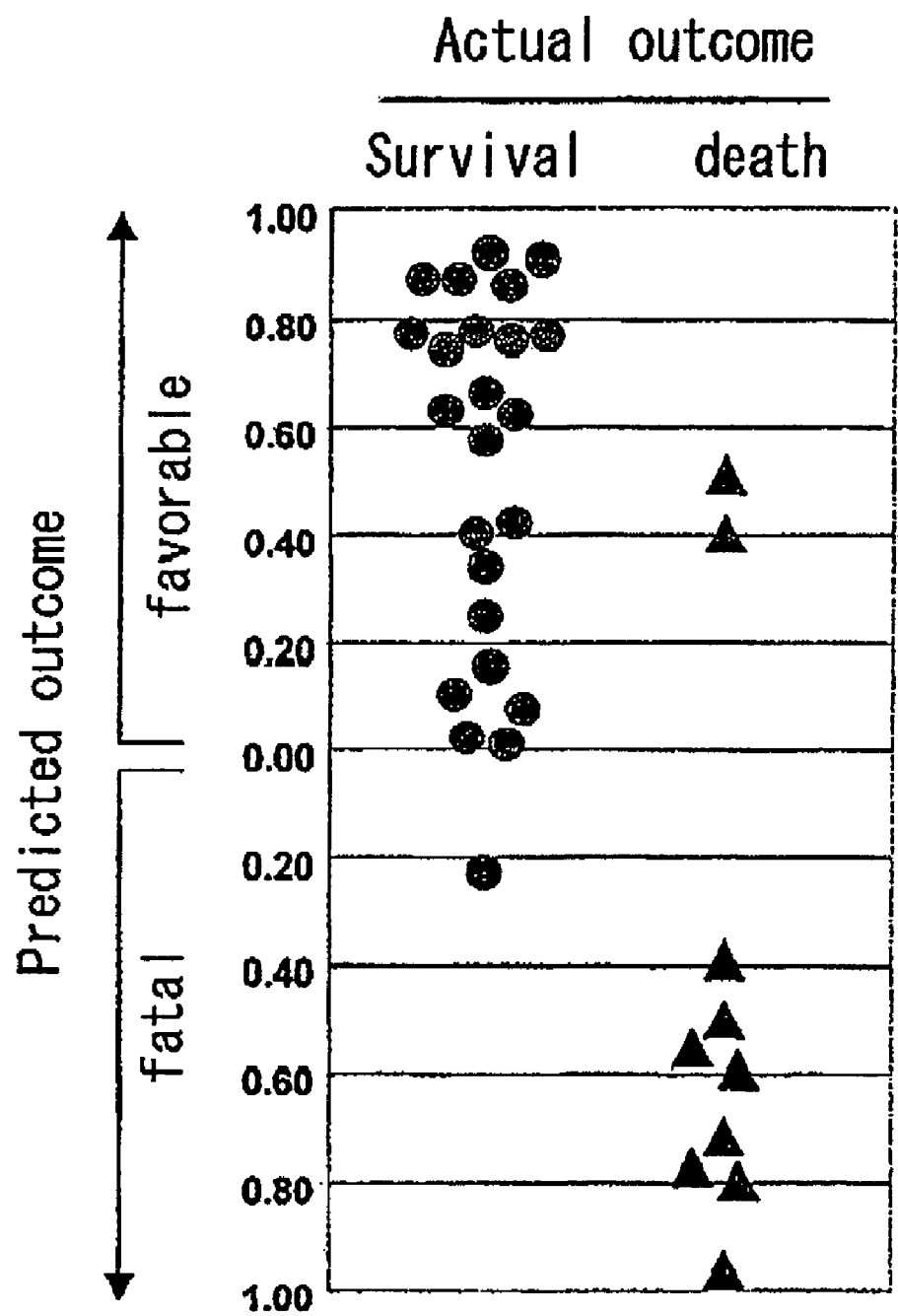
FIG. 3 represents the outcomes obtained by predicting patients with non-squamous cell lung cancer using 12 predictive genes in a weighted-voting model.
Figure 4:
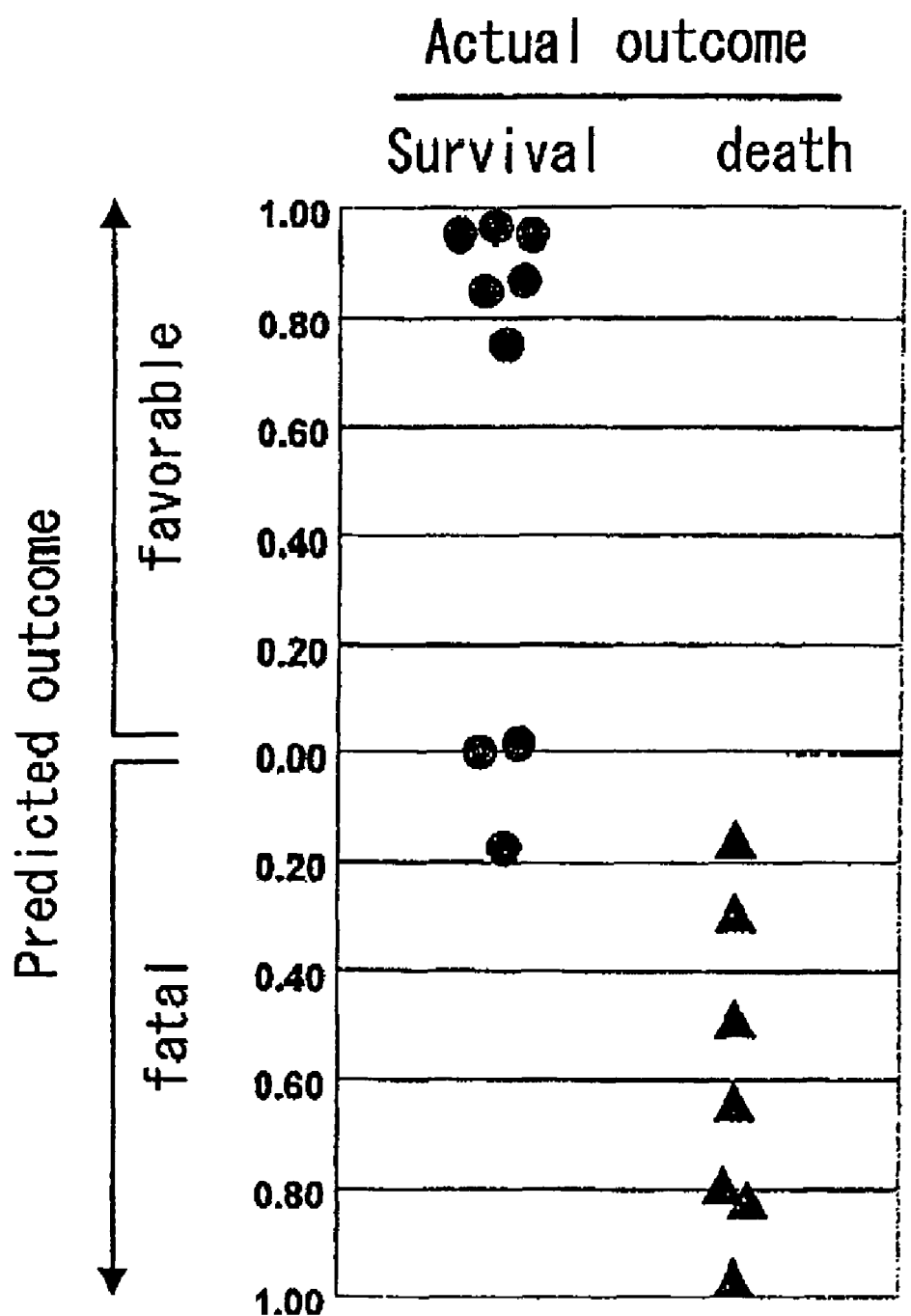
FIG. 4 represents the outcomes obtained by predicting patients with squamous cell lung cancer using 19 predictive genes in a weighted-voting model.
Figure 5:
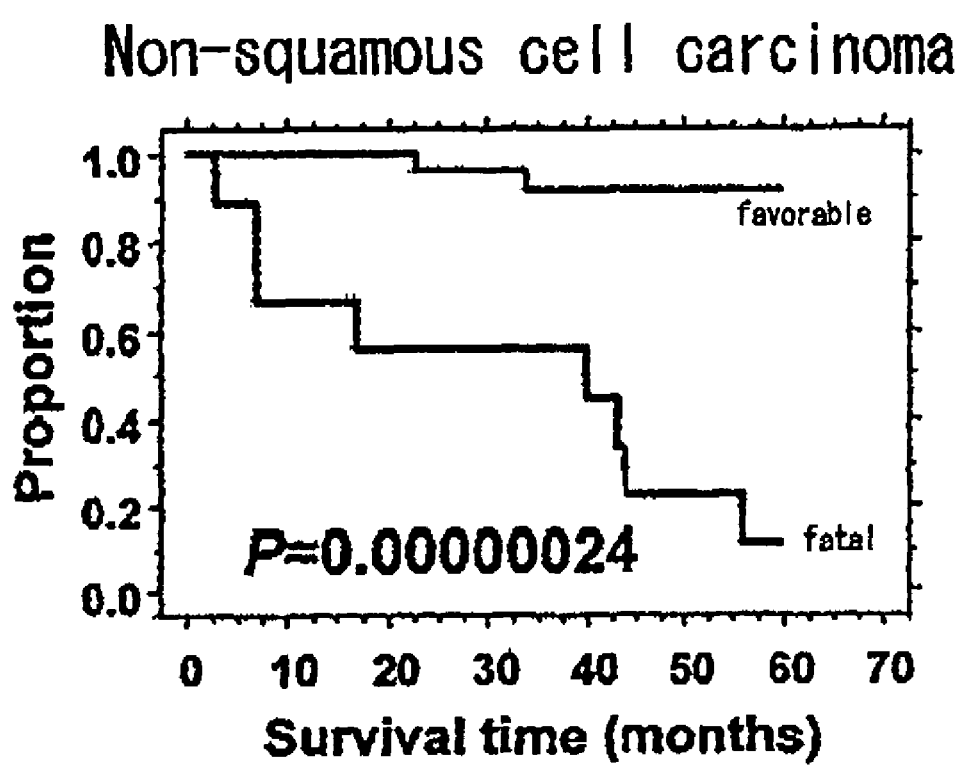
FIG. 5 is a survival curve showing the prognosis "favorable" or "fatal" of patients with non-squamous cell lung cancer.
Figure 6:
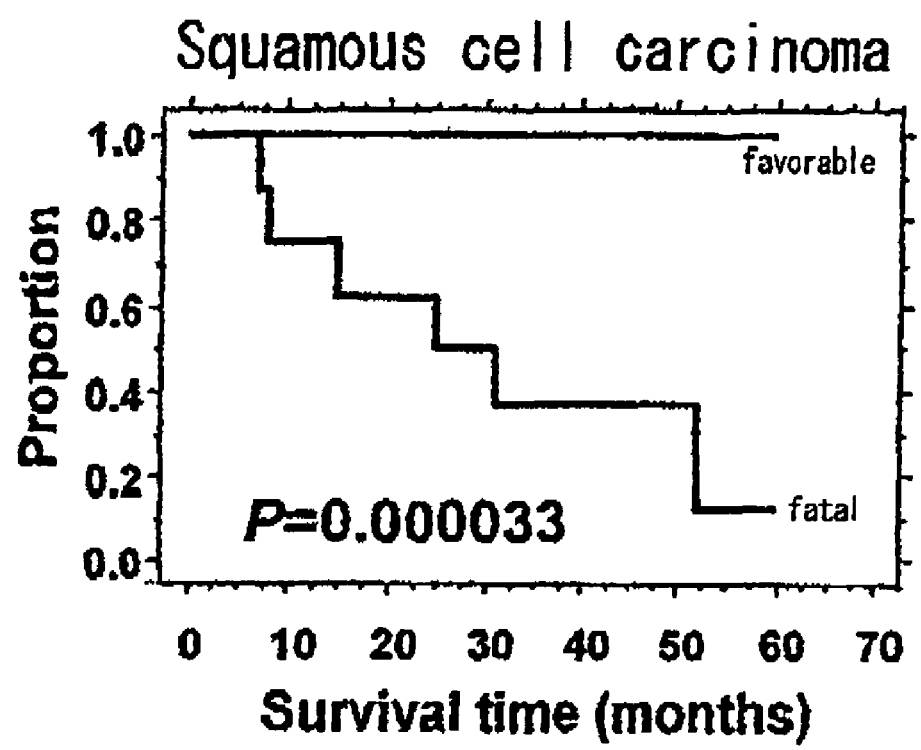
FIG. 6 is a survival curve showing the prognosis "favorable" or "fatal" of patients with squamous cell lung cancer.

These outcomes show that among 34 patients with non-squamous cell cancer, a five year survival rate after operation of 31 patients (91%) was accurately predicted (FIG. 3). Specifically, among 25 patients who were predicted to be "prognosis favorable", 23 patients (92%) were actually survival over five years after operation. Among 9 patients who were decided to be "prognosis fatal", only one patient was survival over five years. The difference between the survival curve of 25 patients who were decided to be "prognosis favorable" and that of 9 patients who were predicted to be "prognosis fatal" was very significant.

What is claimed is:

1. A method for predicting a survival rate of a patient with non-small cell lung cancer, said method comprising the steps of: (a) isolating a cancer tissue section or a plurality of tissue sections from said patient;
(b) extracting mRNAs from said tissue section or plurality of tissue sections;
(c) transforming said mRNAs from step (b) into cDNAs, wherein said cDNAs are labeled;
(d) determining the expression strengths of all sequences from Group A, consisting of SEQ ID NO: 1, SEQ ID NO: 2, SEQ ID NO: 4, SEQ ID NO: 5, SEQ ID NO: 6, SEQ ID NO: 8, SEQ ID NO: 9, SEQ ID NO: 10), SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 24, and SEQ ID NO: 25 and Group B consisting of SEQ ID NO: 3, SEQ ID NO: 7, and SEQ ID NO: 23 and;
(d) predicting a favorable prognosis when the expression of the sequences of Group A are collectively increased while the expression of the sequences of Group B are collectively decreased, or predicting a fatal prognosis when the expressions of the sequences of Group A are collectively decreased while the expressions of the sequences of Group B are collectively increased.

* * * * *

SEQUENCE LISTING

<160> NUMBER OF SEQ ID NOS: 73

<210> SEQ ID NO 1
<211> LENGTH: 4232
<212> TYPE: DNA
<213> ORGANISM: Homo sapiens

<400> SEQUENCE: 1

```
aaaattgcgt ttgagtttgc cgcgagccgg gccaatcggt tttgccaacg catgcccacg      60
tgctggcgaa caaatgtaaa cacggagatc gtgtgccggg cacttggttt cgtggtgggc     120
aactgtgctg ctgtttcttt tggccgcgga caaggtcggc agaggtggac ccctgcttgg     180
gagagctctt ctcgctgtgc tgacacccgc ccctaacagt caccaccccc ggggaaataa     240
tggggctcgg aggcctcctc ccagccagtg tccagcctaa gcacatcggc tcccgcagtt     300
cagaaaggtc ccgaggcccg agtcaccatt tccggctcag acctcgaccc ggaacgtggc     360
tgcccactgc cacgcccact acgcccagt ggctcgcccc aggggacgag gggcaagaag      420
cggcctccga gggcagcggc cgaaggccat tcggtccctg gctcttccca gctcgcagag     480
acccggaagc gctgcccggc cgcctgcccc tcttcagatc ccccagcacc ggaggagcag     540 cgaggggct cgctccaggc cggctttcgg gtcggcttag gcgaatccag ctctcttttg      600
cccctcccag aaggcccagc cccgtccggg cggtgttcgg gcggcgccgg gccgggcccc     660
ccgccgcccc aggctcgctc ataggccgg aacaccacag cccgcccaga cttggctggc     720
gccgagccgg gggtggagcc agcgggttcc cgccaaaatc gcgtagctgg tccttccccc     780
gcgggctacg tcgcgccctc cttttttttt caaacccgga gctgcactgg gattggtgga     840
ctgggcactc acgtggttaa cggtcgcggg aagccgcgga gcccgaacct gagactggac     900
ctgaggagac ctcagcctcg gtgctcgggc cgccccgcct ctgccggaaa gtccgcgccg     960
ccgctgccgc caccgtccgc agcccgagcg ccccggagcc gcaggccgcc gccgcgcaga    1020
gacgccgcgg ctgcgactag gcgcgcccag ccgcacgtgg cggacccgcc cccaggcccg    1080
```

| | |
|---|---|
| cagtgtcctg gaccccgcag gcctccgctc tcctgtcctc ggccccgtcc ccagggccgc | 1140 |
| gatgagcttc ctgagccgac agcagccgcc gccaccccgc cgcgccgggg cggcctgcac | 1200 |
| cttgcggcag aagctgatct tctcgccctg cagcgactgt gaggaggagg aagaagagga | 1260 |
| ggaggaggag ggcagcggcc acagcaccgg ggaggactcg gcctttcaag agcccgactc | 1320 |
| gccgctgccg cccgcgcgga gccccacgga gcccgggccc gagcgccgcc gctcgcccgg | 1380 |
| gccggccccc gggagccccg gcgagctgga ggaggacctg ttgctgcccg gcgcctgccc | 1440 |
| gggcgcggac gaggcgggcg gtggggcgga gggcgactcg tgggaggagg agggcttcgg | 1500 |
| ctcctcgtcg ccggtcaagt cgccggcggc ccctacttc ctgggtagct ctttctcgcc | 1560 |
| ggtgcgctgc ggcggcccag gagatgcgtc gccgcgggt tgcggggcgc gccgggcggg | 1620 |
| cgaaggccgc cgctcgccgc ggccggacca cccgggcacc ccgccacaca agaccttccg | 1680 |
| caagctgcga ctcttcgaca ccccgcacac gcccaagagt ttgctctcca agctcggggg | 1740 |
| aattgattcc agctctgtta aactccgggg tagttctctc ttcatggata cagaaaaatc | 1800 |
| aggaaaaagg gaattgatg tgcgacagac tcctcaagtg aatattaatc cttttactcc | 1860 |
| ggattctttg ttgcttcatt cctcaggaca gtgtcgtcgt agaaagagaa cgtattggaa | 1920 |
| tgattcctgt ggtgaagaca tggaagccag tgattatgag cttgaagatg aaacaagacc | 1980 |
| tgctaagaga attacaatta ctgaaagcaa tatgaagtcc cggtatacaa cagaatttca | 2040 |
| tgagctagag aaaatcggct ctggagaatt tggttctgta tttaagtgtg tgaagaggct | 2100 |
| ggatggatgc atttatgcca ttaagcgatc aaaaaagcca ttggcgggct ctgttgatga | 2160 |
| gcagaacgct ttgagagaag tatatgctca tgcagtgctt ggacagcatt ctcatgtagt | 2220 |
| tcgatatttc tctgcgtggg cagaagatga tcatatgctt atacagaatg aatattgtaa | 2280 |
| tggtggaagt ttagctgatg ctataagtga aaactacaga atcatgagtt actttaaaga | 2340 |
| agcagagttg aaggatctcc ttttgcaagt tggccgaggc ttgaggtata ttcattcaat | 2400 |
| gtctttggtt cacatggata taaaacctag taatattttc atatctcgaa cctcaatccc | 2460 |
| aaatgctgcc tctgaagaag gagacgaaga tgattgggca tccaacaaag ttatgtttaa | 2520 |
| aataggtgat cttgggcatg taacaaggat ctccagtcca caagttgaag agggcgatag | 2580 |
| tcgttttctt gcaaatgaag ttttacagga gaattatacc catctaccaa agcagatat | 2640 |
| ttttgcgctt gccctcacag tggtatgtgc tgctggtgct gaacctcttc cgagaaatgg | 2700 |
| agatcaatgg catgaaatca gacagggtag attacctcgg ataccacaag tgctttccca | 2760 |
| agaatttaca gagttgctaa aagttatgat tcatccagat ccagagagaa gaccttcagc | 2820 |
| aatggcactg gtaaagcatt cagtattgct gtccgcttct agaaagagtg cagaacaatt | 2880 |
| acgaatagaa ttgaatgccg aaaagttcaa aaattcactt ttacaaaaag aactcaagaa | 2940 |
| agcacagatg gcaaaagctg cagctgagga aagagcactc ttcactgacc ggatggccac | 3000 |
| taggtccacc acccagagta atagaacatc tcgacttatt ggaaagaaaa tgaaccgctc | 3060 |
| tgtcagcctt actatatact gagctactcc tttcccacct cccctgaac actgtgacaa | 3120 |
| gaggaagcta ggttgaaatc actgatagaa tccagtttgc aattactttc tcgattggtg | 3180 |
| tcagtagttt tactgattag acttttatt gtgaattaca gttgaaagct gtattttgat | 3240 |
| gattgctatg tcaggctttc atctaatctt accagtctgt cttctgtagg atgtgtcact | 3300 |
| gttggatgtt acaccagcct ttccagggtt aaccactgtg gtggtgtgct gcttatagtt | 3360 |
| tgctgttgca ttgtaataaa aggtgtcttt ccctgtagtg acctgtaaaa agtactcaag | 3420 |

-continued

| | | |
|---|---|---|
| ggctttatta cagacatacc ctcccttrga aaagggacat gctaaaagac tcattactac | 3480 | |
| tcagccttca atgtacctgt gtgtccatct tatatttctt ttttttttt aattgtgaat | 3540 | |
| tagacttgta tatcccactg ggagcacttt gtaggcattg catgaaccat gggatgatga | 3600 | |
| ttctgtggag gtattgcctt gtgaatttgc tgctatttta gttttgtctt tgctgtaaac | 3660 | |
| ttgtagcatt aaacaatcat tgttgttaat aggtcttctt tttgaaacaa ttatgtgaaa | 3720 | |
| tgtatagctg cttttgatga aaagcagcta tttgcctttt ttttttttcc tttgaactttt | 3780 | |
| gaagctagtg cattggaaaa atgcacccctt tccctccttt ggaatgctgt attaatgtag | 3840 | |
| tataataatt actggttttg taacttgttc tggtaatgtc cttcccggac tctttttaaa | 3900 | |
| tgtctccccc taagttttat acttgattgt attattagtc tgtttttaaa tgttttgccc | 3960 | |
| ggttttttctc ttcaatattt gtgtatataa accgatcttc gtgatactgt acatagctgt | 4020 | |
| ttgaaatgcc agaatgactt ctgacattcc aagtttttca caaatatat tttatctgtg | 4080 | |
| attagccatt tgactaataa tactggctaa cagatgttga aaaaaattgt ctgtttgttt | 4140 | |
| tctcattaat tttggtctaa aacatgtttg cacttgtctt tgacttgtgt tttattaaca | 4200 | |
| ttgattggca tattaaaagt cactctgagc tt | 4232 | |

<210> SEQ ID NO 2
<211> LENGTH: 2189
<212> TYPE: DNA
<213> ORGANISM: Homo sapiens

<400> SEQUENCE: 2

| | | |
|---|---|---|
| gcagagggag cgagcgggcg gccggctagg gtggaagagc cgggcgagca gagctgcgct | 60 | |
| gcgggcgtcc tggaagggga gatccggagc gaataggggg cttcgcctct ggcccagccc | 120 | |
| tcccgctgat cccccagcca gcggtccgca acccttgccg catccacgaa actttgccca | 180 | |
| tagcagcggg cgggcacttt gcactggaac ttacaacacc cgagcaagga cgcgactctc | 240 | |
| ccgacgcggg gaggctattc tgcccatttg gggacacttc cccgccgctg ccaggacccg | 300 | |
| cttctctgaa aggctctcct tgcagctgct tagacgctgg attttttttcg ggtagtggaa | 360 | |
| aaccagcagc ctcccgcgac gatgcccctc aacgttagct tcaccaacag gaactatgac | 420 | |
| ctcgactacg actcggtgca gccgtatttc tactgcgacg aggaggagaa cttctaccag | 480 | |
| cagcagcagc agagcgagct gcagccccccg gcgcccagcg aggatatctg gaagaaattc | 540 | |
| gagctgctgc ccaccccgcc cctgtcccct agccgccgct ccgggctctg ctcgccctcc | 600 | |
| tacgttgcgg tcacacccctt ctcccttcgg ggagacaacg acggcggtgg cgggagcttc | 660 | |
| tccacggccg accagctgga gatggtgacc gagctgctgg gaggagacat ggtgaaccag | 720 | |
| agtttcatct gcgacccgga cgacgagacc ttcatcaaaa acatcatcat ccaggactgt | 780 | |
| atgtggagcg gcttctcggc cgccgccaag ctcgtctcag agaagctggc ctcctaccag | 840 | |
| gctgcgcgca aagacagcgg cagcccgaac cccgcccgcg ccacagcgt ctgctccacc | 900 | |
| tccagcttgt acctgcagga tctgagcgcc gccgcctcag agtgcatcga cccctcggtg | 960 | |
| gtcttccccct accctctcaa cgacagcagc tcgcccaagt cctgcgcctc gcaagactcc | 1020 | |
| agcgccttct ctccgtcctc ggattctctg ctctcctcga cggagtcctc cccgcagggc | 1080 | |
| agccccgagc cctggtgct ccatgaggag acaccgccca ccaccagcag cgactctgag | 1140 | |
| gaggaacaag aagatgagga agaaatcgat gttgtttctg tggaaaagag gcaggctcct | 1200 | |
| ggcaaaaggt cagagtctgg atcaccttct gctggaggcc acagcaaacc tcctcacagc | 1260 | |
| ccactggtcc tcaagaggtg ccacgtctcc acacatcagc acaactacgc agcgcctccc | 1320 | |

```
tccactcgga aggactatcc tgctgccaag agggtcaagt tggacagtgt cagagtcctg    1380
agacagatca gcaacaaccg aaaatgcacc agccccaggt cctcggacac cgaggagaat    1440
gtcaagaggc aacacacaa cgtcttggag cgcagagga ggaacgagct aaaacggagc     1500
ttttttgccc tgcgtgacca gatcccggag ttggaaaaca atgaaaaggc ccccaaggta    1560
gttatcctta aaaagccac agcatacatc ctgtccgtcc aagcagagga gcaaaagctc    1620
atttctgaag aggacttgtt gcggaaacga cgagaacagt tgaaacacaa acttgaacag    1680
ctacggaact cttgtgcgta aggaaaagta aggaaaacga ttccttctaa cagaaatgtc    1740
ctgagcaatc acctatgaac ttgtttcaaa tgcatgatca aatgcaacct cacaaccttg    1800
gctgagtctt gagactgaaa gatttagcca taatgtaaac tgcctcaaat tggactttgg    1860
gcataaaaga acttttttat gcttaccatc tttttttttt ctttaacaga tttgtattta    1920
agaattgttt ttaaaaaatt ttaagattta cacaatgttt ctctgtaaat attgccatta    1980
aatgtaaata actttaataa aacgtttata gcagttacac agaatttcaa tcctagtata    2040
tagtacctag tattataggt actataaacc ctaattttt ttatttaagt acattttgct     2100
ttttaaagtt gattttttc tattgttttt agaaaaaata aaataactgg caaatatatc     2160
attgagccaa aaaaaaaaa aaaaaaaa                                        2189

<210> SEQ ID NO 3
<211> LENGTH: 2352
<212> TYPE: DNA
<213> ORGANISM: Homo sapiens

<400> SEQUENCE: 3
gaaacttaaa ggtgtttacc ttgtcatcag catgtaagct aattatctcg ggcaagatgt      60
aggcttctat tgtcttgttg ctttagcgct tacgccccgc ctctggtggc tgcctaaaac    120
ctggcgccgg gctaaaacaa acgcgaggca gcccccgagc ctccactcaa gccaattaag    180
gaggactcgg tccactccgt tacgtgtaca tccaacaaga tcggcgttaa ggtaacacca    240
gaatatttgg caaagggaga aaaaaaaagc agcgaggctt cgccttcccc ctctcccttt    300 ttttttcctcc tcttccttcc tcctccagcc gccgccgaat catgtcgatg agtccaaagc   360
acacgactcc gttctcagtg tctgacatct tgagtcccct ggaggaaagc tacaagaaag    420
tgggcatgga gggcggcggc ctcggggctc cgctggcggc gtacaggcag ggccaggcgg    480
caccgccaac agcggccatg cagcagcacg ccgtggggca ccacgcgcc gtcaccgccg    540 cctaccacat gacggcggcg ggggtgcccc agctctcgca ctccgccgtg gggggctact    600
gcaacggcaa cctgggcaac atgagcgagc tgccgccgta ccaggacacc atgaggaaca    660
gcgcctctgg ccccggatgg tacggcgcca acccagaccc gcgcttcccc gccatctccc    720
gcttcatggg cccggcgagc ggcatgaaca tgagcggcat gggcggcctg ggctcgctgg    780 ggacgtgag caagaacatg gccccgctgc caagcgcgcc gcgcaggaag cgccgggtgc     840
tcttctcgca ggcgcaggtg tacgagctgg agcgacgctt caagcaacag aagtacctgt    900
cggcgccgga gcgcgagcac ctggccagca tgatccacct gacgcccacg caggtcaaga    960
tctggttcca gaaccaccgc tacaaaatga gcgccaggc caaggacaag gcggcgcagc    1020
agcaactgca gcaggacagc gggcggcgcg ggggcggcg gggcaccggg tgcccgcagc    1080
agcaacaggc tcagcagcag tcgcgcgac gcgtggcggt gccggtcctg gtgaagacg     1140 gcaaaccgtg ccaggcgggt gccccgcgc cgggcgccgc cagcctacaa ggccacgcgc    1200
```

-continued

| | | | | |
|---|---|---|---|---|
| agcagcaggc | gcagcaccag | gcgcaggccg | cgcaggcggc | ggcagcggcc atctccgtgg | 1260 |
| gcagcggtgg | cgccggcctt | ggcgcacacc | cgggccacca | gccaggcagc gcaggccagt | 1320 |
| ctccggacct | ggcgcaccac | gccgccagcc | ccgcggcgct | gcagggccag gtatccagcc | 1380 |
| tgtcccacct | gaactcctcg | ggctcggact | acggcaccat | gtcctgctcc accttgctat | 1440 |
| acggtcggac | ctggtgagag | gacgccgggc | cggccctagc | ccagcgctct gcctcaccgc | 1500 |
| ttccctcctg | cccgccacac | agaccaccat | ccaccgctgc | tccacgcgct tcgacttttc | 1560 |
| ttaacaacct | ggccgcgttt | agaccaagga | acaaaaaaac | cacaaaggcc aaactgctgg | 1620 |
| acgtctttct | ttttttcccc | ccctaaaatt | tgtgggtttt | ttttttaaa aaagaaaat | 1680 |
| gaaaaacaac | caagcgcatc | caatctcaag | gaatctttaa | gcagagaagg gcataaaaca | 1740 |
| gctttggggt | gtcttttttt | ggtgattcaa | atgggttttc | cacgctaggg cggggcacag | 1800 |
| attggagagg | gctctgtgct | gacatggctc | tggactctaa | agaccaaact tcactctggg | 1860 |
| cacactctgc | cagcaaagag | gactcgcttg | taaataccag | gatttttttt ttttttgaa | 1920 |
| gggaggacgg | gagctgggga | gaggaaagag | tcttcaacat | aacccacttg tcactgacac | 1980 |
| aaaggaagtg | ccccctcccc | ggcaccctct | ggccgcctag | gctcagcggc gaccgccctc | 2040 |
| cgcgaaaata | gtttgtttaa | tgtgaacttg | tagctgtaaa | acgctgtcaa aagttggact | 2100 |
| aaatgcctag | tttttagtaa | tctgtacatt | ttgttgtaaa | aagaaaaacc actcccagtc | 2160 |
| cccagcccctt | cacatttttt | atgggcattg | acaaatctgt | gtatattatt tggcagtttg | 2220 |
| gtatttgcgg | cgtcagtctt | tttctgttgt | aacttatgta | gatatttggc ttaaatatag | 2280 |
| ttcctaagaa | gcttctaata | aattatacaa | attaaaaga | ttcttttct gattaaaaaa | 2340 |
| aaaaaaaaaa | aa | | | | 2352 |

<210> SEQ ID NO 4
<211> LENGTH: 431
<212> TYPE: DNA
<213> ORGANISM: Homo sapiens
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t

<400> SEQUENCE: 4

| | | | | |
|---|---|---|---|---|
| cagcagcgga | gacccatcct | ctgaccccct | tggctctcca | accctcctcg ctttgtgagg | 60 |
| cacccgagcc | ttactccctg | caggtgccac | cctaagcaac | gtctgctccc cttccccac | 120 |
| cagtccagct | ggcctggaca | gtatcccata | cccaactcca | gcagctgctt ctccatccct | 180 |
| ctaatgagac | taaccatatt | gtgcttcaca | gtagagccag | cttggggcca ccaaagctgc | 240 |
| ccattgtttc | tctaggagct | gggcctctct | aggcacaatt | tggcactaaa tcaggaggac | 300 |
| aaaatatttt | cccatttctg | gccggaggaa | ttccggggga | ggcccaggag ganttttgtta | 360 |
| ggattcctta | ggagggtcct | ctggggaggc | cctaaaccct | ttccagattc attggccaca | 420 |
| tttttccnt  | c          | | | | 431 |

<210> SEQ ID NO 5
<211> LENGTH: 292
<212> TYPE: DNA
<213> ORGANISM: Homo sapiens
<220> FEATURE:
<221> NAME/KEY: misc_feature
<222> LOCATION: (286)..(286)
<223> OTHER INFORMATION: n is a, c, g, or t

<400> SEQUENCE: 5

```
gttttgatg cagacataaa aatagcaatc attttaaatt gtcaaaattt ccagattact      60
ggtaaaaatt atttgaaaac aaacttatgg gtaataaagg ctagtcagaa ccctatacca    120
taaagtgtag ttaccataca gattaatatg tagcaaaaat gtatgcttga tatttctcaa    180
ctgtgttaat ttttctgctg tattccagct gaccaaaaca atattaagaa tgcatcttta    240
taaatggggt gctaattgat aatgggaaat aatttaggta atgggnctat ac            292
```

<210> SEQ ID NO 6
<211> LENGTH: 400
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (304)..(304)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (350)..(350)

```
<223> OTHER INFORMATION: n is a, c, g, or t
<220> FEATURE:
<221> NAME/KEY: misc_feature
<222> LOCATION: (382)..(382)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t

<400> SEQUENCE: 6
ngaagggata gccagcgcga aggaagtnct ggagtcgtgt gttttggctg cgcgtgatcc      60
tgcgtgggtc gggaggtgtt tctgtgtagg tntctggccc tttnatcagt cgtgcggagg     120
accgcgtgat ttccttccag ttctnctcgg ntttcangaa aagcctaaag attagactnt     180
aagaaaagan aatagaagcc atgtttcgaa gacctgtatt acaggtactt cgtcagtttc     240
taagacatga gtcccganac aactaccagt ttggttcttn gaaagatccc tggaatgcac     300 tttncttttng gccaggtng ggtcaggac cctgtctttt taggacaggn tcggaaggga     360
aaaaaatccc agttcacaat anttttntc ttaggcaact                           400

<210> SEQ ID NO 7
<211> LENGTH: 859
<212> TYPE: DNA
<213> ORGANISM: Homo sapiens

<400> SEQUENCE: 7
acaggagagc atagcacctg cagcaagatg gatgtgggca gcaaagaggt cctgatggag      60
agcccgccgg actactccgc agctccccgg ggccgatttg gcattccctg ctgcccagtg     120
cacctgaaac gccttcttat cgtggtggtg gtggtggtcc tcatcgtcgt ggtgattgtg     180
ggagccctgc tcatgggtct ccacatgagc cagaaacaca cggagatggt tctggagatg     240
agcattgggg cgccggaagc ccagcaacgc ctggccctga gtgagcacct ggttaccact     300
gccaccttct ccatcggctc cactggcctc gtggtgtatg actaccagca gctgctgatc     360
gcctacaagc cagcccctgg cacctgctgc tacatcatga gatagctccc agagagcatc     420
cccagtcttg aggctctcaa tagaaaagtc cacaacttcc agatggaatg ctctctgcag     480
gccaagcccg cagtgcctac gtctaagctg ggccaggcag aggggcgaga tgcaggctca     540
gcaccctccg gaggggaccc ggccttcttg ggcatggccg tgaacaccct gtgtggcgag     600
gtgccgctct actacatcta ggacgcctcc ggtgagcagg gtcagtgaa gccccaacgg     660 gaaaggaaac gccccgggca aagggtcttt tgcagctttt gcagacgggc aagaagctgc     720
ttctgcccac accgcaggga caaaccctgg agaaatggga gcttggggag aggatgggag     780
tgggcagagg tggcacccag gggcccggga actcctgcca caacagaata aagcagcctg     840
atttgaaaag caaaaaaaa                                                  859

<210> SEQ ID NO 8
<211> LENGTH: 4050
<212> TYPE: DNA
<213> ORGANISM: Homo sapiens

<400> SEQUENCE: 8
cttgcaatcc aggctttcct tggaagtggc tgtaacatgt atgaaaagaa agaaaggagg      60
accaagagat gaaagagggc tgcacgcgtg ggggcccgag tggtgggcgg ggacagtcgt     120
cttgttacag gggtgctggc cttcctggc ggctgccct gtcggccccg cccgagaacc      180
tccctgcgcc agggcagggt ttactcatcc cggcgaggtg atcccatgcg cgagggcggg     240
```

```
cgcaagggcg gccagagaac ccagcaatcc gagtatgcgg catcagccct tcccaccagg      300
cacttccttc cttttcccga acgtccaggg agggagggcc gggcacttat aaactcgagc      360
cctggccgat ccgcatgtca gaggctgcct gcaggggct gcgcgcacgg caagaagtgt      420
ctgggctggg acggacagga gaggctgtcg ccatcggcgt cctgtgcccc tctgctccgg      480
cacggccctg tcgcagtgcc cgcgctttcc ccggcgcctg cacgcggcgc gcctgggtaa      540
catgcttggg gtcctggtcc ttggcgcgct ggccctggcc ggcctggggt tccccgcacc      600
cgcagagccg cagccgggtg gcagccagtg cgtcgagcac gactgcttcg cgctctaccc      660
gggcccccgcg accttcctca atgccagtca gatctgcgac ggactgcggg gccacctaat      720
gacagtgcgc tcctcggtgg ctgccgatgt catttccttg ctactgaacg cgacggcgg      780
cgttggccgc cggcgcctct ggatcggcct gcagctgcca cccggctgcg cgacccaa       840
gcgcctcggg cccctgcgcg gcttccagtg ggttacggga acaacaaca ccagctatag      900
caggtgggca cggctcgacc tcaatggggc tcccctctgc ggcccgttgt gcgtcgctgt      960
ctccgctgct gaggccactg tgcccagcga gccgatctgg gaggagcagc agtgcgaagt     1020
gaaggccgat ggcttcctct gcgagttcca cttcccagcc acctgcaggc cactggctgt     1080
ggagcccggc gccgcggctg ccgccgtctc gatcacctac ggcaccccgt tcgcggcccg     1140
cggagcggac ttccaggcgc tgccggtggg cagctccgcc gcggtggctc ccctcggctt     1200
acagctaatg tgcaccgcgc cgccggagc ggtccagggg cactgggcca gggaggcgcc     1260
gggcgcttgg gactgcagcg tggagaacgg cggctgcgag cacgcgtgca atgcgatccc     1320
tggggctccc cgctgccagt gcccagccgg cgccgccctg caggcagacg ggcgctcctg     1380
caccgcatcc gcgacgcagt cctgcaacga cctctgcgag cacttctgcg ttcccaaccc     1440
cgaccagccg ggctcctact cgtgcatgtg cgagaccggc taccggctgg cggccgacca     1500
acaccggtgc gaggacgtgg atgactgcat actggagccc agtccgtgtc cgcagcgctg     1560
tgtcaacaca cagggtggct tcgagtgcca ctgctaccct aactacgacc tggtggacgg     1620
cgagtgtgtg gagcccgtgg acccgtgctt cagagccaac tgcgagtacc agtgccagcc     1680
cctgaaccaa actagctacc tctgcgtctg cgccgagggc ttcgcgccca ttccccacga     1740
gccgcacagg tgccagatgt tttgcaacca gactgcctgt ccagccgact gcgaccccaa     1800
cacccaggct agctgtgagt gccctgaagg ctacatcctg gacgacggtt tcatctgcac     1860
ggacatcgac gagtgcgaaa acggcggctt ctgctccggg gtgtgccaca acctccccgg     1920
taccttcgag tgcatctgcg ggcccgactc ggcccttgcc cgccacattg gcaccgactg     1980
tgactccgga aaggtggacg gtggcgacag cggctctggc gagcccccgc ccagcccgac     2040
gcccggctcc accttgactc ctccggccgt ggggctcgtg cattcgggct tgctcatagg     2100
catctccatc gcgagcctgt gcctggtggt ggcgcttttg gcgctcctct gccacctgcg     2160
caagaagcag ggcgccgcca gggccaagat ggagtacaag tgcgcggccc cttccaagga     2220
ggtagtgctg cagcacgtgc ggaccgagcg gacgccgcag agactctgag cggcctccgt     2280
ccaggagcct ggctccgtcc aggagctgtg cctcctcacc cccagctttg ctaccaaagc     2340
accttagctg gcattacagc tggagaagac cctccccgca cccccaagc tgttttcttc     2400
tattccatgg ctaactggcg aggggtgat tagagggagg agaatgagcc tcggcctctt     2460
ccgtgacgtc actggaccac tgggcaatga tggcaatttt gtaacgaaga cacagactgc     2520
gatttgtccc aggtcctcac taccgggcgc aggagggtga gcgttattgg tcggcagcct     2580
```

```
tctgggcaga ccttgacctc gtgggctagg gatgactaaa atatttattt tttttaagta    2640
tttaggtttt tgtttgtttc ctttgttctt acctgtatgt ctccagtatc cactttgcac    2700
agctctccgg tctctctctc tctacaaact cccacttgtc atgtgacagg taaactatct    2760
tggtgaattt ttttttccta gccctctcac atttatgaag caagccccac ttattcccca    2820
ttcttcctag ttttctcctc ccaggaactg ggccaactca cctgagtcac cctacctgtg    2880
cctgacccta cttcttttgc tcatctagct gtctgctcag acagaacccc tacatgaaac    2940
agaaacaaaa acactaaaaa taaaaatggc catttgcttt ttcaccagat ttgctaattt    3000
atcctgaaat ttcagattcc cagagcaaaa taattttaaa caaagggttg agatgtaaaa    3060
ggtattaaat tgatgttgct ggactgtcat agaaattaca cccaagagg tatttatctt     3120 tacttttaaa cagtgagcct gaattttgtt gctgttttga tttgtactga aaatggtaa     3180 ttgttgctaa tcttcttatg caatttcctt ttttgttatt attacttatt tttgacagtg    3240
ttgaaaatgt tcagaaggtt gctctagatt gagagaagag acaaacacct cccaggagac    3300
agttcaagaa agcttcaaac tgcatgattc atgccaatta gcaattgact gtcactgttc    3360
cttgtcactg gtagaccaaa ataaaaccag ctctactggt cttgtggaat tgggagcttg    3420
ggaatggatc ctggaggatg cccaattagg gcctagcctt aatcaggtcc tcagagaatt    3480
tctaccattt cagagaggcc ttttggaatg tggcccctga acaagaattg gaagctgccc    3540
tgcccatggg agctggttag aaatgcagaa tcctaggctc caccccatcc agttcatgag    3600
aatctatatt taacaagatc tgcagggggt gtgtctgctc agtaatttga ggacaaccat    3660
tccagactgc ttccaatttt ctggaataca tgaaatatag atcagttata agtagcaggc    3720
caagtcaggc ccttattttc aagaaactga ggaattttct ttgtgtagct ttgctctttg    3780
gtagaaaagg ctaggtacac agctctagac actgccacac agggtctgca aggtctttgg    3840
ttcagctaag ctaggaatga aatcctgctt cagtgtatgg aaataaatgt atcatagaaa    3900 tgtaacttt gtaagacaaa ggttttcctc ttctattttg taaactcaaa atatttgtac      3960
atagttattt atttattgga gataatctag aacacaggca aaatccttgc ttatgacatc    4020
acttgtacaa aataaacaaa taacaatgtg                                    4050

<210> SEQ ID NO 9
<211> LENGTH: 466
<212> TYPE: DNA
<213> ORGANISM: Homo sapiens
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t

<400> SEQUENCE: 9
tttttttttt tttttttttt taagtctcct tctttattat taggaaaaca acaacaacaa      60
caaacaaaaa aatggcgtca tgaatatgaa cagcattgtc agatgaatta gttgaagtgg     120
tttttttttt gtttttttt ttttttttgt actgngtcct caaatttaat ggattaatgt      180
gtcttgtata tataaaaaga aaacctctac cttcagcctc tgcctattct tgctccgtct     240
aggacatccn caatttcgtc gatgaccagc ttggtgaata agtattactg taccaactgg     300
```

| | |
|---|---|
| gcctcctcta gcaggcccct gaaggcagtg gaataaaatg aaatcttcgc cctttaagaa | 360 |
| ctcctgacct taatgtggta gtagtatctt gtccttgagg ggatttcctt cccctcaccc | 420 |
| ctaagacttt cacaacctgg tgactggaaa gaaccaccac naatcc | 466 |

```
<210> SEQ ID NO 10
<211> LENGTH: 470
<212> TYPE: DNA
<213> ORGANISM: Homo sapiens
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t

<400> SEQUENCE: 10
```

| | |
|---|---|
| aacaaatgct tctgccaaag tgaaagaatt ttatgtctta atgcttttct ttaaaaaaaa | 60 |
| aaaaagtcaa cattgaacta ggacatgctc tgcttcccca ccccattttt gctgactaca | 120 |
| ttttaaaaaa tctattggca gaaaacaaga tattttcttc aaatagagtg attatgtttt | 180 |
| attgctatttt tgtttagtat atattttnct caattgggaa aaaaatctag gtgaaaaaaa | 240 |
| ttacctaaca agagaagtag tttacatagt cataacattt aaatttgctg cccaaaaaat | 300 |
| gtaaaanaat ttnaatgtaa aatgtcacat antttcaaaa aacttacctc aattgtctat | 360 |
| catttatcat gtactataag tcaacttcct aaataagatt cagtcccttta ttataagccc | 420 |
| ctactggtac catngtatac attaaaaacg ctncctccaaa atttcctggc | 470 |

```
<210> SEQ ID NO 11
<211> LENGTH: 1007
<212> TYPE: DNA
<213> ORGANISM: Homo sapiens

<400> SEQUENCE: 11
```

| | |
|---|---|
| aactccaggg ctagtgagct ggaccggaag taggtttcta cccgaccgca ttttacgtgg | 60 |
| tgctgcattt ccggtagcgg cggcgggaaa tcggctgtgg gagagaggct aggcctctga | 120 |
| ggaggcgaat ccggcgggta tcagagccat cagaaccgcc accatgacgg tgggcaagag | 180 |
| cagcaagatg ctgcagcata ttgattacag gatgaggtgc atcctgcagg acggccggat | 240 |
| cttcattggc accttcaagg cttttgacaa gcacatgaat ttgatcctct gtgactgtga | 300 |
| tgagttcaga aagatcaagc caaagaactc caaacaagca gaaagggaag agaagcgagt | 360 |
| cctcggtctg gtgctgctgc gaggggagaa tctggtctca atgacagtag agggacctcc | 420 |
| tcccaaagat actggtattg ctcgagttcc acttgctgga gctgccgggg gcccagggat | 480 |

| | |
|---|---:|
| cggcagggct gctggcagag gaatcccagc tggggttccc atgccccagg ctcctgcagg | 540 |
| acttgctggg ccagtccgtg gggttggcgg gccatcccaa caggtgatga ccccacaagg | 600 |
| aagaggtact gttgcagccg ctgcagctgc tgccacagcc agtattgccg gggctccaac | 660 |
| ccagtaccca cctggccgtg ggggtcctcc cccacctatg ggccgaggag cacccoctcc | 720 |
| aggcatgatg ggcccacctc ctggtatgag acctcctatg ggtcccccaa tggggatccc | 780 |
| ccctggaaga gggactccaa tgggcatgcc ccctccggga tgcggcctc ctccccctgg | 840 |
| gatgcgaggg cccoctcccc cgggaatgcg cccaccaagg ccctagactc atcttggccc | 900 |
| tcctcagctc cctgcctgtt tcccgtaagg ctgtacatag tccttttatc tccttgtggc | 960 |
| ctatgaaact ggtttataat aaactcttaa gagaacatta taattgc | 1007 |

<210> SEQ ID NO 12
<211> LENGTH: 3582
<212> TYPE: DNA
<213> ORGANISM: Homo sapiens

<400> SEQUENCE: 12

| | |
|---|---:|
| ctgctcgcgg cgccgcctcc tgctcctccc gctgctgctg ccgctgccgc cctgagtcac | 60 |
| tgcctgcgca gctccggccg cctggctccc catactagtc gccgatattt ggagttctta | 120 |
| caacatggca gacattgaca acaaagaaca gtctgaactt gatcaagatt tggatgatgt | 180 |
| tgaagaagta gaagaagagg aaactggtga agaaacaaaa ctcaaagcac gtcagctaac | 240 |
| tgttcagatg atgcaaaatc ctcagattct tgcagccctt caagaaagac ttgatgtgtct | 300 |
| ggtagaaaca ccaacaggat acattgaaag cctgcctagg gtagttaaaa gacgagtgaa | 360 |
| tgctctcaaa aacctgcaag ttaaatgtgc acagatagaa gccaaattct atgaggaagt | 420 |
| tcacgatctt gaaaggaagt atgctgttct ctatcagcct ctatttgata gcgatttga | 480 |
| aattattaat gcaatttatg aacctacgga agaagaatgt gaatggaaac cagatgaaga | 540 |
| agatgagatt tcggaggaat tgaaagaaaa ggccaagatt gaagatgaga aaaaggatga | 600 |
| agaaaaagaa gaccccaaag gaattcctga atttttggtta actgttttta agaatgttga | 660 |
| cttgctcagt gatatggttc aggaacacga tgaacctatt ctgaagcact tgaaagatat | 720 |
| taaagtgaag ttctcagatg ctggccagcc tatgagtttt gtcttagaat ttcactttga | 780 |
| acccaatgaa tattttacaa atgaagtgct gacaaagaca tacaggatga ggtcagaacc | 840 |
| agatgattct gatccctttt cttttgatgg accagaaatt atgggttgta cagggtgcca | 900 |
| gatagattgg aaaaaaggaa agaatgtcac tttgaaaact attaagaaga agcagaaaca | 960 |
| caagggacgt gggacagttc gtactgtgac taaaacagtt tccaatgact ctttctttaa | 1020 |
| cttttttgcc cctcctgaag ttcctgagag tggagatctg gatgatgatg ctgaagctat | 1080 |
| ccttgctgca gacttcgaaa ttggtcactt tttacgtgag cgtataatcc caagatcagt | 1140 |
| gttatatttt actggagaag ctattgaaga tgatgatgat gattatgatg aagaaggtga | 1200 |
| agaagcggat gaggaagggg aagaagaagg agatgaggaa atgatccag actatgaccc | 1260 |
| aaagaaggat caaaacccag cagagtgcaa gcagcagtga agcaggatgt atgtggcctt | 1320 |
| gaggataacc tgcactgtaa tagcctaaac acaactctta tttacttaca gccttatgtt | 1380 |
| tttgtatttt cttggtagac taggtaattt tttttttaaag gacaggaaac tgatattta | 1440 |
| aagaccaatt tgttctacct agcatttaa ctagttttc tgccagctat gttgaatgca | 1500 |
| caaattctgt cacgcatgtt cattcattgc tacataattt ggttcttctg gaatattttt | 1560 |
| atgtagctct tggagtacag ctatgaaaat taacaactgt taaaggaaat accttttttt | 1620 |

```
tttttttgta atttttcct tgaagaacca aagtattttt tcagctggtt gttgaatagg    1680
gttaagtccg cttggattag ctgtgccttt cattactttg ttacagaaat gcagtgactt    1740
atactaagac aatttattgt ttaaaaaaaa aattggcaag acaactatat ggttaagaat    1800
ttccagtatg accacaccca ataactgtta ttagagtgtt aatggattat tgtgttttag    1860
gtgacatagt taactgtaaa gtaacctgac tcagtatagt tactggtacc acagtgaggt    1920
gaataaaacg ggattttcag aagttagcct gaatttaact gtattttaa atttaacctc    1980
cattaactaa gcatctttc tttgtggtag ggtctacctt ctgcttccct ggaaaggatg    2040
aatttacatc atttgacaag cctatttca agttatttgt tgtttgtttg cttgtttttg    2100
ttttgcagc taaataaaa atttcaaata caattttagt tcttacaaga taatgtctta    2160
attttgtacc aattcaggta gaagtagagg cctaccttga attaagggtt atactcagtt    2220
tttaacacat tgttgaagaa aaggtaccag ctttggaacg agatgctata ctaataagca    2280
agtgtaaaaa aaaaaaaaa agaggaagaa aatcttaagt gattgatgct gttttcttt     2340
aaaaaaaaaa aaaaaaattc attttctttg ggttagagct agagagaagg ccccaagctt    2400
ctatggtttc ttctaattct tattgcttaa agtatgagta tgtcacttac ccgtgcttct    2460
gtttactgtg taattaaaat gggtagtact gtttacctaa ctacctcatg gatgtgttaa    2520
ggcatattga gttaaatctc atataatgtt tctcaatctt gttaaaagct caaaattttg    2580
ggcctatttg taatgccagt gtgacactaa gcattttgtt cacaccacgc tttgataact    2640
aaactggaaa acaaaggtgt taagtacctc tgttctggat ctgggcagtc agcactcttt    2700
ttagatcttt gtgtggctcc tattttata gaagtggagg gatgcactat ttcacaaggt    2760
ccaagatttg ttttcagata ttttgatga ctgtattgta aatactacag ggatagcact    2820
atagtattgt agtcatgaga cttaaagtgg aaataagact attttgaca aaagatgcca    2880
ttaaatttca gactgtagag ccacatttac aatacctcag gctaattact gttaattttg    2940
gggttgaact ttttttgaca gtgagggtgg attattggat tgtcattaga ggaaggtcta    3000
gatttcctgc tcttaataaa attacattga attgattttt agaggtaatg aaaacttcct    3060
ttctgagaag ttagtgttaa ggtcttggaa tgtgaacaca ttgtttgtag tgctatccat    3120
tcctctcctg agatttttaac ttactactgg aaatccttaa ccaattataa tagcttttt    3180
tcttttatttt caaaatgatt tcctttgctt tgattagaca ctatgtgctt ttttttttta    3240
accatagttc atcgaaatgc agcttttct gaacttcaaa gatagaatcc catttttaat    3300
gaactgaagt agcaaaatca tctttttcat tctttaggaa atagctattg ccaaagtgaa    3360
ggtgtagata taccctagtc ttgttacata agggggatgt ggtttgcaga agaattttct    3420
ttataaaatt gaagttttaa gggacgtcag tgtttatgcc atttttccag ttccaaaatg    3480
attccattcc attctagaaa tttgaagtat gtaacctgaa atccttaata aaatttggat    3540
ttaattttat aaaaaaaaaa aaaaaaaaa aaaaaaaaa aa                         3582
```

<210> SEQ ID NO 13
<211> LENGTH: 6232
<212> TYPE: DNA
<213> ORGANISM: Homo sapiens

<400> SEQUENCE: 13

```
ctgccagatc agtttgtcac cacccaggct cccttgcctt tggctgggtg caacttccat      60
tttaggtgtt ggatctgagg gggaaaaaaa agagagaggg agagagagag aaagaagagc     120
```

-continued

```
aggaaagatc ccgaaaggag gaagaggtgg cgaaaaatca actgccctgc tggatttgtc    180
tttctcagca ccttggcgaa gccttgggtt tctttcttaa aggactgatt tttagaactc    240
cacatttgag gtgtgtggct tttgaagaaa atgtatgtac tgacgggaaa aggaagataa    300
gcaagtcgaa tttttgtctt acgctctctc cttcctgctt cctccttgct gtggtggctg    360
ggatgctcct tccatgattt tttgaatcta gactgggctg ttctctgtgt taaaccaatc    420
agttgcgacc ttctcttaac agtgtgaagt gagggggtct ctctccctcc ttctccttcc    480
tctgtgattc accttccttt ttaccctgcc ctgcggcggc tccgccccctt accttcatgg    540
acgactcaga ggtggagtcg accgccagca tcttggcctc tgtgaaggaa caagaggccc    600
agtttgagaa gctgacccgg gcgctggagg aggaacggcg ccacgtctcg gcgcagctgg    660
aacgcgtccg ggtctcacca caagatgcca acccactcat ggccaacggc acactcaccc    720
gccggcatca gaacggccgg tttgtgggcg atgctgacct tgaaagacag aaattttcag    780
atttgaaact caacgacccc caggatcaca gtcaccttct atatagcacc atccccagga    840
tgcaggagcc ggggcagatt gtggagacct acacggagga ggatcctgag ggagccatgt    900
ctgtagtctc tgtggagacc tcagatgatg ggaccactcg gcgcacagag accacggtca    960
agaaagtagt gaagactgtg acaacacgga cagtacagcc agtcgctatg ggaccagacg   1020
ggttgcctgt ggatgcttca tcagtttcta caaactatat ccagactttg ggtcgtgatt   1080
tccgcaagaa tggcaatggg ggacctggtc cctatgtggg gcaagctggc actgctaccc   1140
ttcctaggaa cttccactac cctcctgatg gttatagtcg ccactatgaa gatggttatc   1200
caggtggcag tgataactat ggcagtctgt cccgggtgac ccgcattgag gagcggtata   1260
ggcccagcat ggaaggctac cgggcaccta gtagacagga tgtgtatggg ccccaaccccc  1320
aggttcgggt aggtgggagc agcgtggatc tgcatcgctt tcatccagag ccttatgggc   1380
tagaggatga ccagcgtagt atgggctatg atgacctgga ttatggtatg atgtctgatt   1440
atggcactgc ccgtcggact gggacaccct ctgaccctcg tcggcgcctc aggagctatg   1500
aagacatgat tggtgaggag gtgccatcgg atcaatacta ctgggctcct ttggcccagc   1560
atgagcgagg aagtttagca agcttggata gcctgcgcaa aggagggcct ccacctccta   1620
attggagaca gccagagctg ccagaggtga tcgccatgct tggattccgc ttggatgctg   1680
tcaagtccaa tgcagctgca tacctgcaac acttatgcta ccgcaatgac aaggtgaaga   1740
ctgacgtgcg gaagctcaag ggcatcccag tactggtggg attgttagac catcccaaaa   1800
aggaagtgca ccttggagcc tgtggagctc tcaagaatat ctcttttgga cgtgaccagg   1860
ataacaagat tgccataaaa aactgtgatg gtgtgcctgc ccttgtgcga ttgcttcgaa   1920
aggctcgtga tatggacctt actgaagtta ttaccggaaa ccctgtggaa tctttcatccc  1980
atgactcaat caaaatggag attgtggacc atgcactgca tgccttgaca gatgaagtga   2040
tcattcctca ttctggttgg gagcgggaac taatgaagaa ctgtaagcca cgccatattg   2100
agtgggaatc ggtgctcacc aacacagctg gctgccttag gaatgtaagc tcagagagga   2160
gtgaagctcg ccgcgaaactt cgggaatgtg atggtttagt tgatgccctc attttcattg   2220
ttcaggctga gattgggcag aaggattcag acagcaagct tgtagagaac tgtgttgcc    2280
ttcttcggaa cttatcatat caagttcacc gggagatccc acaggcagag cgttaccaag   2340
aggcagctcc caatgttgcc aacaatactg gccacatgc tgccagttgc tttggggcca    2400
agaagggcaa agggaaaaaa cctatagagg atccagcaaa cgatacagtg gatttcccta   2460
aaagaacgag tccagctcga ggctatgagc tcttatttca gccagaggtg gttcggatat   2520
```

```
acatctcact tcttaaggag agcaagactc ctgccatcct agaagcctca gctggagcta      2580
tccagaactt gtgtgctggg cgctggacgt atggtcgata catccgctct gctctgcgtc      2640
aagagaaggc tctttctgcc atagctgacc tcctgactaa tgaacatgaa cgggtggtga      2700
aagctgcatc tggagcactg agaaacctgg ctgtggatgc tcgcaacaaa gaattaattg      2760
gtaaacatgc tattcctaac ttggtaaaga atctgccagg aggacagcag aactcctctt      2820
ggaatttctc tgaggacact gtcatctcta ttttgaacac tatcaacgag gttatcgctg      2880
agaacttgga ggctgccaaa aagcttcgag agacacaggg tattgagaag ctggtgttga      2940
tcaacaaatc agggaaccgc tcagaaaaag aagttcgagc agcagcactt gtattacaga      3000
caatctgggg atataaggaa ctgcggaagc cactggaaaa agaaggatgg aagaaatcag      3060
actttcaggt gaatctaaac aatgcttccc gaagccagag cagtcattca tatgatgata      3120
gtactctccc tctcattgac cggaaccaaa atcagataa caactattcc acaccaaatg      3180
agagaggaga ccacaataga acactggatc gatcggggga tctaggcgac atggagccat      3240
tgaagggaac aacacccttg atgcaggacg aggggcagga atctctggag gaagagttgg      3300
atgtgttggt tttggatgat gagggggggcc aagtgtctta cccctccatg cagaagattt      3360
agcaccacta tctccgttcc atctgggctt atatgtactt ttattttttg gtggtgaaat      3420
tgactgatga ttttcctttt tcttcgctgg actattgtgc caactgccag gctgcctcct      3480
gcccttacag ccctaagtgg ctgccttctt ccatcaact cccaacttct tcctgtgaag      3540
tttaattgtc tcaacgcctc cccctcccccc attccctcca ttttctccc aagaaacctg      3600 actcaattat ttgcatattt tgagaaactg ctgcagatta gttctttttg ccagttttcc      3660
ctggaactcc tggcctttg tggagggag ggatggagaa ataggaatc ttcactagaa      3720 gccgtgggaa gaattggaag ttacatgctg tatatgcaat gtccagcagt ctgataaact      3780
gacgattctt aatcaagatt ttttcctga tggggaaggg acttttattt tcttttagag      3840
aggggaaagt gtgagctctt cccttattcc taatggctat ttttgaagca aagaaggcca      3900
gcaacattgg cacatgccac ctggcaaagg acccttgagt aagtgaaggt ctcctaaaac      3960
tgggattaag aaaccttgct ctcctcatct ccaaggcagg gaccatcaag aacctacaga      4020
ctccatctct tctgcaagcc tcatgccaac cctgggctat gctgctgcc ccttaaacac      4080 aggctgtcct taacccacct ctcctgccct gtgatatgtc tgctgagttg gcctggccat      4140
ttccaagagc ctgtagaaag gggagaatgt caaggaagac ttttggtaga gaaggagcag      4200
aaagatgtgt ttttgggaag aagaagacct ctaggaggag ctagtaggaa tgtacatgaa      4260
gcaattagtc tgaaactggc ttccccactc ccccgtttct ccttttccta tccttatagg      4320
cctgtccctt gcctctgccc tggattggtt ggcaaactat aggacttgat gtacataact      4380
cctgtccctt ttcccttaca aggtgggat tgccctgcc tttgcctctt ctttgtgcct      4440
ttggcctggg gtgcatctcc tcccgccctt ccatgtgcct ttctttgcct ctgcagtctc      4500
atttctcata attttgcaaa ttatattttg ttgctttctt acctactatt ggccctaaat      4560
agcagaaaga agagaagtga ccgagagaac ctcagattct tcattgagga ttggtatagc      4620
catgatttca gtcatagcaa gcttttgctc aacagcatat gggtgggatt tggcaaaaat      4680
cctattctga tgaatctcaa agtaaggctg gtaagagaag tgagtggtgt gactcttact      4740
ccttaggtgc ccagaattta ccatcatctc tgaaggagtt acaggaagt ggtctcccca      4800 attctcccct ccctccagta ttgcccctc tcactttagc atatattaat tagcaggttg      4860
```

-continued

```
ggctagagaa atcagctgct atgcgggttg attattatta ttatttctaa tccttttcct    4920
tatttgcctt ctactcccct taatctaatc taaaagctct gttccatgca actggagttc    4980
cttatccctc tcttcccctt cccttatata ttgaggctat ggggtaggag aaaagtgcac    5040
aacccaccac ccctctact cgtgcattaa aatttcttat ttacccttttt cccccttccc    5100
atttcttccc actttcatct accttttctg gcaaaaagga ccttttgct ctctgtgacc     5160
ctaagagcac actgcacagg gaaaattgcc ccatccagac ctggctccac tcttgatctc    5220
tcttgtcctc ttctgctctt ttcctggtgc tcttttttct cggtggggtg tgggtaatag    5280
aacagccgtg ggcttttggg gacctttaac tttttttttct ctcttttgtt tataaaaaac   5340
actaaacatt caattccaga gaacccaaaa tcccaccttc ccaccgaaca ctactaaggg    5400
gcttgtgttc tgctccatac ctttttctctt ttctttctgt cttgttaatg cttttaaaaa   5460
caaatgagtt ttttatataa ataaagtttt taaagtgtgt atgtgggggg tctgtgtcat    5520
ttcttcactt caagctgtta tttcttccct gctttgcatc tttgttactt ccttatgtat    5580
cagtgtcctt tccagagcaa ccagaaggag gttataccag gatttattttt gagctcagcc    5640
ccaactcttt atcaagcaac attcttgtta actatatgtg aaacattttt tcttctgaag    5700
attcttaaaa attgaatgtg gctgaagttg aacatgggag cttattgcta atttagagat    5760
aggaaactga agcataaaga attaatgact tactttaatt actggaattc ttctgcaaca    5820
tttgacaaaa ctaaccttga ataaggccca ctgtaatacg tagctctctt aaatataaca    5880
cttaggacta gaagattaga aactaccaat cccaactacg taataggaaa atgtaggatc    5940
aaaaggccca tgtatataag tactgaccac tgggccataa tgttgcttct caggctatat    6000
gcagtccttt agtcagaagt caataggcct atttattaat attttacaga ccatattacc    6060
tggattacca gggactatct ttgctgcaga gatcaagggt taagatctat gggaagatac    6120
ttatttttct gaggtcctta tgtcctgtca tataattaaa gactcaagag aatttatgtg    6180
aaatgctttc tgtatgcccc aatctttaga ttaaaattat atacctgctc ct             6232
```

<210> SEQ ID NO 14
<211> LENGTH: 1965
<212> TYPE: DNA
<213> ORGANISM: Homo sapiens

<400> SEQUENCE: 14

```
gtctggttct ctctctccag aaggttctgc cggttccccc agctctgggt acccggctct      60
gcatcgcgtc gccatgatgg gccatcgtcc agtgctcgtg ctcagccaga acacaaagcg     120
tgaatccgga agaaaagttc aatctggaaa catcaatgct gccaagacta ttgcagatat     180
catccgaaca tgtttgggac ccaagtccat gatgaagatg cttttggacc caatgggagg     240
cattgtgatg accaatgatg gcaatgccat tcttcgagag attcaagtcc agcatccagc     300
ggccaagtcc atgatcgaaa ttagccggac ccaggatgaa gaggttggag atgggaccac     360
atcagtaatt attcttgcag gggaaatgct gtctgtagct gagcacttcc tggagcagca     420
gatgcaccca acagtggtga tcagtgctta ccgcaaggca ttggatgata tgatcagcac     480
cctaaagaaa ataagtatcc cagtcgacat cagtgacagt gatatgatgc tgaacatcat    540
caacagctct attactacca aagccatcag tcggtggtca tctttggctt gcaacattgc    600
cctggatgct gtcaagatgg tacagtttga ggagaatggt cggaaagaga ttgacataaa    660
aaatatgca agagtggaaa agatacctgg aggcatcatt gaagactcct gtgtcttgcg    720
tggagtcatg attaacaagg atgtgaccca tccacgtatg cggcgctata tcaagaaccc    780
```

```
tcgcattgtg ctgctggatt cttctctgga atacaagaaa ggagaaagcc agactgacat      840
tgagattaca cgagaggagg acttcacccg aattctccag atggaggaag agtacatcca      900
gcagctctgt gaggacatta tccaactgaa gcccgatgtg gtcatcactg aaaagggcat      960
ctcagattta gctcagcact accttatgcg ggccaatatc acagccatcc gcagagtccg     1020
gaagacagac aataatcgca ttgctagagc ctgtgggggcc cggatagtca gccgaccaga   1080
ggaactgaga gaagatgatg ttggaacagg agcaggcctg ttggaaatca gaaaattgg      1140 agatgaatac tttactttca tcactgactg caaagacccc aaggcctgca ccattctcct     1200
ccggggggct agcaaagaga ttctctcgga agtagaacgc aacctccagg atgccatgca     1260
agtgtgtcgc aatgttctcc tggaccctca gctggtgcca gggggtgggg cctccgagat    1320
ggctgtggcc catgccttga cagaaaaatc aaggccatg actggtgtgg aacaatggcc      1380
atacagggct gttgcccagg ccctagaggt cattcctcgt accctgatcc agaactgtgg    1440
ggccagcacc atccgtctac ttacctccct tcgggccaag cacacccagg agaactgtga    1500 gacctgggt gtaaatggtg agacgggtac tttggtggac atgaaggaac tgggcatatg      1560
ggagccattg gctgtgaagc tgcagactta aagacagca gtggagacgg cagttctgct      1620
actgcgaatt gatgacatcg tttcaggcca caaaaagaaa ggcgatgacc agagccggca    1680
aggcggggct cctgatgctg ccaggagtg agtgctaggc aaggctactt caatgcacag     1740
aaccagcaga gtctcccctt ttcctgagcc agagtgccag gaacactgtg gacgtctttg    1800
ttcagaaggg atcaggttgg ggggcagccc ccagtcccctt tctgtcccag ctcagttttc   1860
caaaagacac tgacatgtaa ttcttctcta ttgtaaggtt tccatttagt ttgcttccga    1920
tgattaaatc taagtcattt gaaaaaaaaa aaaaaaaaa aaaaa                      1965

<210> SEQ ID NO 15
<211> LENGTH: 3454
<212> TYPE: DNA
<213> ORGANISM: Homo sapiens

<400> SEQUENCE: 15
cgccaaagga aagccccctt ggatgagagg caggcgcttc agagaagcta agaaaagcac       60
ctctccgcgc gccccacctc ctccgcctcg cgctcctcct gagcagcggg cccagactgc      120
gctccggccg cggccctcgc cccgcggagc cctcctaccc cggcccgacg ctcggcccgc      180
gacctgcccc gagccctctc catggaggca gcccgcccct ccggctcctg gaacggagcc      240
ctctgccggc tgctcctgct gaccctcgcg atcttaatat ttgccagtga tgcctgcaaa      300
aatgtgacat tacatgttcc ctccaaacta gatgccgaga aacttgttgg tagagttaac      360
ctgaaagagt gctttacagc tgcaaatcta attcattcaa gtgatcctga cttccaaatt      420
ttggaggatg gttcagtcta taacaaaat actattctat tgtcctcgga aagagaagt      480 tttaccatat tactttccaa cactgagaac caagaaaga gaaaatatt tgtcttttg       540 gagcatcaaa caaggtcct aaagaaaaga catactaaag aaaaagttct aaggcgcgcc       600
aagagaagat gggctccaat tccttgttcg atgctagaaa actccttggg tccttttcca     660
cttttccttc aacaggttca atctgacacg gcccaaaact ataccatata ctattccata      720
agaggtcctg gagttgacca agaacctcgg aatttatttt atgtggagag agacactgga    780
aacttgtatt gtactcgtcc tgtagatcgt gagcagtatg aatcttttga gataattgcc    840
tttgcaacaa ctccagatgg gtatactcca gaacttccac tgccctaat aatcaaaata    900
```

```
gaggatgaaa atgataacta cccaattttt acagaagaaa cttatacttt tacaatttt      960
gaaaattgca gagtgggcac tactgtggga caagtgtgtg ctactgacaa agatgagcct    1020
gacacgatgc acacgcct  gaagtactcc atcattgggc aggtgccacc atcacccacc    1080
ctattttcta tgcatccaac tacaggcgtg atcaccacaa catcatctca gctagacaga    1140
gagttaattg acaagtacca gttgaaaata aaagtacaag acatggatgg tcagtatttt    1200
ggtctacaga caacttcaac ttgtatcatt aacattgatg atgtaaatga ccacttgcca    1260
acatttactc gtacttctta tgtgacatca gtggaagaaa atacagttga tgtggaaatc    1320
ttacgagtta ctgttgagga taaggactta gtgaatactg ctaactggag agctaattat    1380
accatttaa  agggcaatga aaatggcaat tttaaaattg taacagatgc caaaaccaat    1440
gaaggagttc tttgtgtagt taagcctttg aattatgaag aaaagcaaca gatgatcttg    1500
caaattggtg tagttaatga agctccattt tccagagagg ctagtccaag atcagccatg    1560
agcacagcaa cagttactgt taatgtagaa gatcaggatg agggccctga gtgtaaccct    1620
ccaatacaga ctgttcgcat gaaagaaaat gcagaagtgg gaacaacaag caatggatat    1680
aaagcatatg acccagaaac aagaagtagc agtggcataa ggtataagaa attaactgat    1740
ccaacagggt gggtcaccat tgatgaaaat acaggatcaa tcaaagtttt cagaagcctg    1800
gatagagagg cagagaccat caaaaatggc atatataata ttacagtcct tgcatcagac    1860
caaggaggga gaacatgtac ggggacactg gcattatac  ttcaagacgt gaatgataac    1920
agcccattca tacctaaaaa gacagtgatc atctgcaaac ccaccatgtc atctgcggag    1980
attgttgcgg ttgatcctga tgagcctatc catggcccac cctttgactt tagtctggag    2040
agttctactt cagaagtaca gagaatgtgg agactgaaag caattaatga tacagcagca    2100
cgtcttttcct atcagaatga tcctccattt ggctcatatg tagtacctat aacagtgaga    2160
gatagacttg gcatgtctag tgtcacttca ttggatgtta cactgtgtga ctgcattacc    2220
gaaaatgact gcacacatcg tgtagatcca aggattggcg gtggaggagt acaacttgga    2280
aagtgggcca tccttgcaat attgttgggc atagcattgc tctttttgcat cctgtttacg    2340
ctggtctgtg gggcttctgg gacgtctaaa caaccaaaag taattcctga tgatttagcc    2400
cagcagaacc taattgtatc aaacacagaa gctcctggag atgacaaagt gtattctgcg    2460
aatggcttca caacccaaac tgtgggcgct tctgctcagg gagtttgtgg caccgtggga    2520
tcaggaatca aaacggagg  tcaggagacc atcgaaatgg tgaaaggagg acaccagacc    2580
tcggaatcct gccggggggc tggccaccat cacaccctgg actcctgcag gggaggacac    2640
acggaggtgg acaactgcag atacacttac tcggagtggc acagttttac tcagccccgt    2700
cttggtgaaa aagtgtatct gtgtaatcaa gatgaaaatc acaagcatgc caagactat     2760
gtcctgacat ataactatga aggaagagga tcggtggctg ggtctgtagg ttgttgcagt    2820
gaacgacaag aagaagatgg gcttgaattt ttggataatt tggagcccaa atttaggaca    2880
ctagcagaag catgcatgaa gagatgagtg tgttctaata agtctctgaa agccagtggc    2940
tttatgactt ttaaaaaaaa ttacaaacca agaattttt  aaagcagaag atgctatttg    3000
tgggggtttt tctctcatta tttggatgga atctctttgg tcaaatgcac atttacagag    3060
agacactata aacaagtaca caatttttc  aatttttaca tattttaaaa ttacttatct    3120
tctatccaag gaggtctaca gagaaattaa agtctgcctt atttgttaca tttgggtata    3180
atgcaacag  ccaatttata gtgcaataaa atgtaattaa ttcaagtcct tattatagac    3240
tatttgaagc acaacctaat ggaaaattgt agagaccttg ctttaacatt atctccagtt    3300
```

```
aattaagtgt tcatgtggtg cttggaaact gttgttttcc tgaacatcta aagtgtgtag    3360
actgcattct tgctattatt ttattcttgt aatgtgacct tttcactgtg caaagggaga    3420
tttctagcca ggcattgact attacaattt catt                                3454

<210> SEQ ID NO 16
<211> LENGTH: 619
<212> TYPE: DNA
<213> ORGANISM: Homo sapiens

<400> SEQUENCE: 16
agcagttcta agggaccata cagagtattc ctctcttcac accaggacca gccactgttg      60
cagcatgagt tcccagcagc agaagcagcc ctgcatccca cccctcagc ttcagcagca     120 gcaggtgaaa cagccttgcc agcctccacc tcaggaacca tgcatcccca aaaccaagga    180
gccctgccac cccaaggtgc ctgagccctg ccaccccaaa gtgcctgagc cctgccagcc    240
caagcttcca gagccatgcc accccaaggt gcctgagccc tgcccttcaa tagtcactcc    300
agcaccagcc cagcagaaga ccaagcagaa gtaatgtggt ccacagccat gcccttgagg    360
agccggccac cagatgctga atcccctatc ccattctgtg tatgagtccc atttgccttg    420
caattagcat tctgtctccc ccaaaaaaga atgtgctatg aagctttctt tcctacacac    480
tctgagtctc tgaatgaagc tgaaggtctt agtaccagag ctagttttca gctgctcaga    540
attcatctga agagagactt aagatgaaag caaatgattc agctccctta tacccccatt    600
aaattcactt tcaattcca                                                  619

<210> SEQ ID NO 17
<211> LENGTH: 3528
<212> TYPE: DNA
<213> ORGANISM: Homo sapiens

<400> SEQUENCE: 17
agccaaggac tctggagccg ccgccgccgc tgctgcggtt catatccgga gtagacggag      60
ccgcagtaga cggatccgcg gctgcaccaa accactgccc ctcggagcct ggtagtgggc     120
cacaagcccc cagtcccaga ggcgtggtgg gtcgggcaga gtcggaagaa ctggctttct     180
agctggaaga tgcggaaggg gagcgactag gccgcttgcg tctgggcctg cagaaggga     240 ccggattttc tggcatcctt aaatcttgtg tcaaggattg gttataatat aaccagaaac     300
catgacggcg gctgagaacg tatgctacac gttaattaac gtgccaatgg attcagaacc     360
accatctgaa attagcttaa aaaatgatct agaaaaagga gatgtaaagt caaagactga     420
agctttgaag aaagtaatca ttatgattct gaatggtgaa aaacttcctg gacttctgat     480
gaccatcatt cgttttgtgc tacctcttca ggatcacact atcaagaaat acttctggt     540 attttgggaa attgttccta aaacaactcc agatgggaga cttttacatg agatgatcct     600
tgtatgtgat gcatacagaa aggatcttca acatcctaat gaatttattc gaggatctac     660
tcttcgtttt ctttgcaaat tgaaagaagc agaattgcta gaacctttaa tgccagctat     720
tcgtgcatgt ttggagcatc gacacagcta tgttagaaga aatgctgttt tggccatcta     780
taccatctat agaaattttg aacatcttat acctgatgct cctgaactga tacatgattt     840
tctggtgaat gagaaggatg caagttgcaa aaggaatgca tttatgatgc taattcatgc     900
agatcaggat cgagctttgg attacttaag tacttgcatt gatcaagttc aaacatttgg     960
agacattctg cagctggtta ttgttgaact gatttataag gtctgtcatg ctaatccatc    1020
```

```
agaaagagct cgtttattc gctgcatcta taacttatta cagtcatcca gccctgctgt    1080
aaaatatgaa gctgctggga cattagtgac actctctagt gcaccaactg caatcaaggc    1140
tgctgctcag tgttacattg atttaattat taaggagagc gacaacaatg taaaactcat    1200
agttttggat cgcttgatag aattaaaaga gcatcctgct catgaacgag tactacagga    1260
tctggttatg gatatcctaa gagtattgag cacaccagac ttagaagtac gaaagaaaac    1320
tctgcagtta gcactggatc ttgtctcttc tagaaatgtt gaagagctgg ttattgtcct    1380
gaagaaggaa gtgataaaaa caaataatgt gtctgagcat gaagatactg acaaatacag    1440
acaactccta gtgcgaacat tgcattcctg ttctgtccga tttccagata tggctgcaaa    1500
tgttattcct gtgttaatgg aatttctcag tgacaacaac gaagcagcag ctgctgatgt    1560
cttggagttt gttcgtgaag ccattcagcg ctttgataac ctgagaatgc ttattgttga    1620
gaagatgctt gaagtctttc atgctattaa atctgtcaag atttaccgag gagcattatg    1680
gatcctggga gaatactgta gtaccaagga agacattcag agtgtgatga ctgagatccg    1740
caggtccctt ggagagatcc caattgtaga gtcagaaata agaaagaag ctggtgaatt    1800 aaaacctgaa gaagaaataa ctgtagggcc agttcagaaa ttggttactg aaatgggtac    1860
ctatgcaact cagagtgccc ttagcagttc tagacccacc aagaaagagg aagacagacc    1920
tcccttgaga ggattccttc tggatggaga tttctttgtt gctgcctccc ttgccacaac    1980
tctgaccaag attgcattgc gctatgtagc tttggttcag gagaagaaaa agcaaaattc    2040
ttttgttgct gaggctatgt tgctcatggc tactatcctg catttgggaa aatcctctct    2100
tcctaagaag ccaattactg atgatgatgt ggatcgaatt tccctgtgcc tcaaggtctt    2160
gtctgaatgt tcacctttaa tgaatgacat tttcaataag gaatgcagac agtccctttc    2220
tcacatgtta tctgctaaac tagaagaaga gaaattatcc caaaagaaag aatctgaaaa    2280
gaggaatgtg acagtacagc ctgatgaccc catttccttc atgcaactaa ctgctaagaa    2340
tgaaatgaac tgcaaggaag atcagtttca gctgagttta ctggcagcaa tgggtaacac    2400
acagaggaaa gaggcagcag atcccctagc atctaaactt aacaaggtca cccaattgac    2460
aggtttctca gatcctgtat atgcagaagc ttacgttcat gtcaaccaat atgatattgt    2520
cctggatgta cttgttgtga accaaaccag tgatactttg cagaattgca cattagaact    2580
agctacacta ggggatctga aacttgtgga aaagccgtct cctttgactc ttgctcctca    2640
tgacttcgca atatattaaag ctaacgtcaa agtagcatca acagaaaatg gaataatttt    2700
tggtaatata gtttatgatg tctctggagc agcaagtgac agaaattgtg tggttctcag    2760
tgatattcac atcgacatca tggactatat ccagcctgca acttgcactg atgcagaatt    2820
ccgtcagatg tgggccgaat ttgaatggga aaacaaagtg acagttaaca ccaacatggt    2880
tgatttaaat gactacttac agcacatatt aaagtcaacc aatatgaaat gcctgactcc    2940
agaaaaggcc ctttctggtt actgtggctt tatggcagcc aacctttatg ctcgttccat    3000
atttggtgaa gatgcacttg caaatgtcag cattgagaag ccaattcacc agggaccaga    3060
tgctgctgtt accggccata taagaattcg tgcaaagagc cagggaatgg ccttaagtct    3120
tggagataaa atcaacttgt cacagaagaa aactagtata taaaaataaa caaaagtcc    3180 ttgaagcttt acagttaatt taggtatggg cttactggac tccaacatct tttgtactct    3240
ttcatgctta tatagaatct gagttcatgc tgaatacttt tcagccaata atttatagcc    3300
tttcccttaa atcaagattg agtttaaaat tatagtttgt cttttgtctt aacagttctg    3360
aatgctgtcc tcaaagtata taatgtttca tgtaccaaga ccccttttcac agtacaataa    3420
```

```
acagatctat tcataaattt ttgttatttt ataaataaat gattacataa ttttagttat    3480
aaaaaaaaaa aaaaaaaaaa agaaaaaaaa aaaaaaaaaa aaaaaaaa                 3528
```

<210> SEQ ID NO 18
<211> LENGTH: 1447
<212> TYPE: DNA
<213> ORGANISM: Homo sapiens

<400> SEQUENCE: 18

```
tgtcactgag ggttgactga ctggagagct caagtgcagc aaagagaagt gtcagagcat      60
gagcgccaag tccagaacca tagggattat tggagctcct ttctcaaagg gacagccacg     120
aggaggggtg gaagaaggcc ctacagtatt gagaaaggct ggtctgcttg agaaacttaa     180
agaacaagag tgtgatgtga aggattatgg ggacctgccc tttgctgaca tccctaatga     240
cagtcccttt caaattgtga gaatccaagg tctgtggga aaagcaagcg agcagctggc      300
tggcaaggtg gcagaagtca agaagaacgg aagaatcagc ctggtgctgg gcggagacca     360
cagtttggca attggaagca tctctggcca tgccagggtc caccctgatc ttggagtcat     420
ctgggtggat gctcacactg atatcaacac tccactgaca accacaagtg gaaacttgca     480
tggacaacct gtatctttcc tcctgaagga actaaaagga aagattcccg atgtgccagg     540
attctcctgg gtgactccct gtatatctgc caaggatatt gtgtatattg gcttgagaga     600
cgtggaccct ggggaacact acattttgaa aactctaggc attaaatact tttcaatgac     660
tgaagtggac agactaggaa ttggcaaggt gatggaagaa acactcagct atctactagg     720
aagaaagaaa aggccaattc atctaagttt tgatgttgac ggactggacc catctttcac     780
accagctact ggcacaccag tcgtgggagg tctgacatac agagaaggtc tctacatcac     840
agaagaaatc tacaaaacag ggctactctc aggattagat ataatggaag tgaacccatc     900
cctggggaag acaccagaag aagtaactcg aacagtgaac acagcagttg caataacctt     960
ggcttgtttc ggacttgctc gggagggtaa tcacaagcct attgactacc ttaacccacc    1020
taagtaaatg tggaaacatc cgatataaat ctcatagtta atggcataat tagaaagcta    1080
atcattttct taagcataga gttatccttc taaagacttg ttctttcaga aaaatgtttt    1140
tccaattagt ataaactcta caaattccct cttggtgtaa aattcaagat gtggaaattc    1200 taacttttttt gaaatttaaa agcttatatt ttctaacttg gcaaaagact tatccttaga    1260
aagagaagtg tacattgatt tccaattaaa aatttgctgg cattaaaaat aagcacactt    1320
acataagccc ccatacatag agtgggactc ttggaatcag gagacaaagc taccacatgt    1380
ggaaaggtac tatgtgtcca tgtcattcaa aaaatgtgat ttttttataat aaactcttta    1440 taacaag                                                              1447
```

<210> SEQ ID NO 19
<211> LENGTH: 3916
<212> TYPE: DNA
<213> ORGANISM: Homo sapiens

<400> SEQUENCE: 19

```
gcttggggcc gccatcttgg caagaggcga agcggcagcg gttcctgtca agggggcagc      60
aggtccagag ctgctggtgc tcccgttccc cagaccctac ccctatcccc agtggagccg     120
gagtgcgggc gcgccccacc accgcccctca ccatggtgct gttggcagca gcggtctgca     180
caaaagcagg aaaggctatt gtttctcgac agtttgtgga aatgaccgaa actcggattg     240
```

```
agggcttatt agcagctttt ccaaagctca tgaacactgg aaaacaacat acgtttgttg    300
aaacagagag tgtaagatat gtctaccagc ctatggagaa actgtatatg gtactgatca    360
ctaccaaaaa cagcaacatt ttagaagatt tggagaccct aaggctcttc tcaagagtga    420
tccctgaata ttgccgagcc ttagaagaga atgaaatatc tgagcactgt tttgatttga    480
tttttgcttt tgatgaaatt gtcgcactgg ataccggga gaatgttaac ttggcacaga    540
tcagaacctt cacagaaatg gattctcatg aggagaaggt gttcagagcc gtcagagaga    600
ctcaagaacg tgaagctaag gctgagatgc gtcgtaaagc aaaggaatta caacaggccc    660
gaagagatgc agagagacag ggcaaaaaag caccaggatt tggcggattt ggcagctctg    720
cagtatctgg aggcagcaca gctgccatga tcacagagac catcattgaa actgataaac    780
caaaagtggc acctgcacca gccaggcctt caggccccag caaggcttta aaacttggag    840
ccaaaggaaa ggaagtagat aactttgtgg acaaattaaa atctgaaggt gaaaccatca    900
tgtcctctag tatgggcaag cgtacttctg aagcaaccaa aatgcatgct ccacccatta    960
atatggaaag tgtacatatg aagattgaag aaaagataac attaacctgt ggacgagacg   1020
gaggattaca gaatatggag ttgcatggca tgatcatgct taggatctca gatgacaagt   1080
atggccgaat tcgtcttcat gtggaaaatg aagataagaa aggggtgcag ctacagaccc   1140
atccaaatgt ggataaaaaa cttttcactg cagagtctct aattggcctg aagaatccag   1200
agaagtcatt tccagtcaac agtgacgtag gggtgctaaa gtggagacta caaccacag    1260 aggaatcttt tattccactg acaattaatt gctggccctc ggagagtgga atggctgtg    1320 atgtcaacat agaatatgag ctacaagaag ataatttaga actgaatgat gtggttatca   1380
ccatcccact cccgtctggt gtcggcgcgc ctgttatcgg tgagatcgat ggggagtatc   1440
gacatgacag tcgacgaaat accctggagt ggtgcctgcc tgtgattgat gccaaaaata   1500
agagtggcag cctggagttt agcattgctg ggcagcccaa tgacttcttc cctgttcaag   1560
tttcctttgt ctccaagaaa aattactgta acatacaggt taccaaagtg acccaggtag   1620
atggaaacag ccccgtcagg ttttccacag agaccacttt cctagtggat aagtatgaaa   1680
ttctgtaata ccaagaagag ggagctgaaa aggaaaattt tcagattaat aaagaagacg   1740
ccaatgatgg ctgaagagtt tttcccagat ttacaagcca ctggagaccc cttttttctg   1800
atacaatgca cgattctctg cgcgcaagga ccctcgactc accccatgt ttcagtgtca    1860 cagagacatt ctttgataag gaatggcac aaacataaag ggaaaggctg ctaattttct    1920
ttggcagatt gtattggcca gcaggaaagc aagctctcca gagaatgccc ccagttaaat   1980
acctcctcta cctttaccta agttgctcct ttattttat tttattatta ttattattat    2040
tattattttt tgagatggag tctcactttg taacccaggc tggaatgcaa tggcatgatc   2100
tcagctcact gcaacctccg cctcctgggt tcaagcaagt ctcctgcctc agcctccgag   2160
tagctgggac tacaggtgca cgccaccacg cctggctaat ttttgtatt ttagtagaga    2220 cggggtttca ccgtgttgcc caggctggtc gcgaactcct gagctcaggc aatccgccca   2280
cctcagcctc ccaaagtgtt gggattacag gcatgagcca ccatgcccag ctgctccttt   2340
attttaatcc ctaaatataa tccctaaata tagttatatt tcatacttag tttgttttta   2400 aaaagtttc tctgtagaaa attttaatca ttcatacct ttacctttag gtttttcttt     2460
ctatacattc agtcaggcac tgggatcatc tgtttacagg cattatattt atttggcact   2520
cctggaacaa gtatatctaa cccattcttg atttttggac tattcaggtg aactatttga   2580
ggggtatggg gtctagaagt taaaagatac gcatgtcttc tgttctttc ccgtatcaat     2640
```

```
tcattccttc atctctttgc caagttgttt tcctttcagg gcctgtcctt ccagtttaga      2700
acagtaccat gaatcccact tgtgtcaata ttaaagatag ctgagaagca cctttcaaat      2760
ggcacagtcc ctcttcaaga tgtctaaaag aatggttatg tctgtccagt tagggatttc      2820
acatccacat gtaatcatgt ctgctgctgt tgctacccaa attttcattt ctccacattt      2880
tgggtactta agctaaaacg taatggccac agtctgtaat ccattcacat tcctcagttt      2940
caccacctcc ctcttccaga ctgcactctc tgtcatcagt cccctccttt ctaacagaaa      3000
tggggttatg attttgaagg ctgtgggttc agggagtctt tgccaatcct gttggcccta      3060
aactatcaag gaggctccat ttcaccattt gattttttgc atttcaggag caactgatt      3120 gtttcgatat gtacatatta ctcacgtata ccccatttcc ttccagtcag cccaacattt      3180
tccaccagtc tgtccccatc tctgaaatcc ttccttctct ttccccctaa gtcttttgag      3240
tgtcatcatg tactggtggt ttctcggttc catctcatcc atttccttt caatggagac       3300 tacagcgtca gccagctcag ccttggcttt taactcaata ttccagtcca tagggtggt       3360 taaaagttgc tgcaaggctg caggcactgg cagtgggaag aggcagacga ctagatgact     3420
tctgcacttt tagctggttg aaaagtacca ctcccactct gaacatctgg ccgtccctgc     3480
aaagagtgta ctgtgcttga agcagagcac tcacacataa atggctgtgt gtggaattgc     3540
ttgccaaaga agtttctagc ctttcccttt cccctaactg catcagggaa gaattcttat     3600
ctctagcttg gtttccacat gaggtttttc tgagaagggc ttgggacaag aagtctgtca     3660
tgttagttaa gcaggcaaga atcctactaa atccagtttt gtttgaaagt tgtttgtccg     3720 tatgatttt taaagtcaa gtttaatttc aaaaaacctt tttttctga gattactttt         3780 ggggtaatat ttaaaatgag agacattttg taaccctgta aaatacatag ggaatataac     3840
attccagtgt atacaaagaa ggcaaattct ttaatcaaat aaagcgtatt ataaaatgag     3900
aaaaaaaaaa aaaaaa                                                      3916

<210> SEQ ID NO 20
<211> LENGTH: 2280
<212> TYPE: DNA
<213> ORGANISM: Homo sapiens

<400> SEQUENCE: 20
tccagccaga aggatggggt ggctcccact cctgctgctt ctgactcaat gcttaggggt       60
ccctgggcag cgctcgccat tgaatgactt ccaagtgctc cggggcacag agctacagca     120
cctgctacat gcggtggtgc ccgggccttg gcaggaggat gtggcagatg ctgaagagtg     180
tgctggtcgc tgtgggccct taatggactg ccgggccttc cactacaacg tgagcagcca     240
tggttgccaa ctgctgccat ggactcaaca ctcgccccac acgaggctgc ggcgttctgg     300
gcgctgtgac ctcttccaga agaaagacta cgtacggacc tgcatcatga caatggggt      360 tgggtaccgg ggcaccatgg ccacgaccgt gggtggcctg ccctgccagg cttggagcca     420
caagttcccg aatgatcaca gtacacgcc cactctccgg aatggcctgg aagagaactt     480
ctgccgtaac cctgatggcg accccggagg tccttggtgc tacacaacag accctgctgt     540
gcgcttccag agctgcggca tcaaatcctg ccgggaggcc gcgtgtgtct ggtgcaatgg     600
cgaggaatac cgcggcgcgg tagaccgcac ggagtcaggg cgcgagtgcc agcgctggga     660
tcttcagcac ccgcaccagc acccttcga gccgggcaag ttcctcgacc aaggtctgga     720
cgacaactat tgccggaatc ctgacggctc cgagcggcca tggtgctaca ctacggatcc     780
```

```
gcagatcgag cgagagttct gtgacctccc ccgctgcggg tccgaggcac agccccgcca    840
agaggccaca actgtcagct gcttccgcgg gaagggtgag ggctaccggg gcacagccaa    900
taccaccact gcgggcgtac cttgccagcg ttgggacgcg caaatccctc atcagcaccg    960
atttacgcca gaaaaatacg cgtgcaaaga ccttcgggag aacttctgcc ggaaccccga   1020
cggctcagag gcgccctggt gcttcacact gcggcccggc atgcgcgcgg ccttttgcta   1080
ccagatccgg cgttgtacag acgacgtgcg gccccaggac tgctaccacg cgcagggga    1140 gcagtaccgc ggcacggtca gcaagacccg caagggtgtc cagtgccagc gctggtccgc   1200
tgagacgccg cacaagccgc agttcacgtt tacctccgaa ccgcatgcac aactggagga   1260
gaacttctgc cggaacccag atggggatag ccatgggccc tggtgctaca cgatggaccc   1320
aaggacccca ttcgactact gtgccctgcg acgctgcgct gatgaccagc cgccatcaat   1380
cctggacccc ccagaccagg tgcagtttga agtgtggc aagagggtgg atcggctgga    1440
tcagcggcgt tccaagctgc gcgtggttgg gggccatccg gcaactcac cctggacagt    1500 cagcttgcgg aatcggcagg ccagcattt ctgcggggg tctctagtga aggagcagtg    1560
gatactgact gcccggcagt gcttctcctc ctgccatatg cctctcacgg gctatgaggt   1620
atggttgggc accctgttcc agaacccaca gcatggagag ccaagcctac agcgggtccc   1680
agtagccaag atggtgtgtg ggccctcagg ctcccagctt gtcctgctca agctggagag   1740
atctgtgacc ctgaaccagc gtgtggccct gatctgcctg ccccctgaat ggtatgtggt   1800
gcctccaggg accaagtgtg agattgcagg ctggggtgag accaaaggta cgggtaatga   1860
cacagtccta aatgtggcct tgctgaatgt catctctaac caggagtgta acatcaagca   1920
ccgaggacgt gtgcgggaga gtgagatgtg cactgaggga ctgttggccc ctgtgggggc   1980
ctgtgagggt gactacgggg gcccacttgc ctgctttacc cacaactgct gggtcctgga   2040
aggaattata atccccaacc gagtatgcgc aaggtcccgc tggccagctg tcttcacgcg   2100
tgtctctgtg tttgtggact ggattcacaa ggtcatgaga ctgggttagg cccagccttg   2160
atgccatatg ccttggggag acaaaaactt cttgtcagac ataaagccat gtttcctctt   2220
taaaaaaaaa aaaaaaaaa aaaaaaaaa aaataaaaaa aaaaaaaaaa aaaaaaaaa    2280
```

<210> SEQ ID NO 21
<211> LENGTH: 2876
<212> TYPE: DNA
<213> ORGANISM: Homo sapiens

<400> SEQUENCE: 21

```
gaattcctgc agctcagcag ccgccgccag agcaggacga accgccaatc gcaaggcacc     60
tctgagaact tcaggatgca gatgtctcca gccctcacct gctagtcct gggcctggcc    120 cttgtctttg gtgaagggtc tgctgtgcac catccccat cctacgtggc ccacctggcc    180
tcagacttcg gggtgaggggt gtttcagcag gtggcgcagg cctccaagga ccgcaacgtg    240
gttttctcac cctatggggt ggcctcggtg ttggccatgc tccagctgac aacaggagga    300
gaaacccagc agcagattca agcagctatg ggattcaaga ttgatgacaa gggcatggcc    360
cccgccctcc ggcatctgta caaggagctc atggggccat ggaacaagga tgagatcagc    420
accacagacg cgatcttcgt ccagcgggat ctgaagctgg tccagggctt catgccccac    480
ttcttcaggc tgttccggag cacggtcaag caagtggact tttcagaggt ggagagagcc    540
agattcatca tcaatgactg ggtgaagaca cacacaaaag gtatgatcag caacttgctt    600
gggaaaggag ccgtggacca gctgacacgg ctggtgctgg tgaatgccct ctacttcaac    660
```

-continued

```
ggccagtgga agactccctt ccccgactcc agcacccacc gccgcctctt ccacaaatca    720
gacggcagca ctgtctctgt gcccatgatg gctcagacca acaagttcaa ctatactgag    780
ttcaccacgc ccgatggcca ttactacgac atcctggaac tgccctacca cggggacacc    840
ctcagcatgt tcattgctgc cccttatgaa aagaggtgc ctctctctgc cctcaccaac    900
attctgagtg cccagctcat cagccactgg aaaggcaaca tgaccaggct gccccgcctc    960
ctggttctgc ccaagttctc cctggagact gaagtcgacc tcaggaagcc cctagagaac   1020
ctgggaatga ccgacatgtt cagacagttt caggctgact tcacgagtct ttcagaccaa   1080
gagcctctcc acgtcgcgca ggcgctgcag aaagtgaaga tcgaggtgaa cgagagtggc   1140
acggtggcct cctcatccac agctgtcata gtctcagccc gcatggcccc cgaggagatc   1200
atcatggaca gacccttcct ctttgtggtc cggcacaacc ccacaggaac agtcctttc    1260 atgggccaag tgatggaacc ctgacccctgg ggaaagacgc cttcatctgg gacaaaactg   1320
gagatgcatc gggaaagaag aaactccgaa gaaaagaatt ttagtgttaa tgactctttc   1380
tgaaggaaga gaagacattt gccttttgtt aaaagatggt aaaccagatc tgtctccaag   1440
accttggcct ctccttggag gacctttagg tcaaactccc tagtctccac ctgagaccct   1500
gggagagaag tttgaagcac aactcccctta aggtctccaa accagacggt gacgcctgcg   1560
ggaccatctg ggcacctgc ttccacccgt ctctctgccc actcgggtct gcagacctgg   1620
ttcccactga ggcccctttgc aggatggaac tacggggctt acaggagctt ttgtgtgcct   1680
ggtagaaact atttctgttc cagtcacatt gccatcactc ttgtactgcc tgccaccgcg   1740
gaggaggctg gtgacaggcc aaaggccagt ggaagaaaca cctttcatc tcagagtcca   1800 ctgtggcact ggccaccct ccccagtaca ggggtgctgc aggtggcaga gtgaatgtcc   1860
cccatcatgt ggcccaactc tcctggcctg gccatctccc tccccagaaa cagtgtgcat   1920
gggttatttt ggagtgtagg tgacttgttt actcattgaa gcagatttct gcttccttt    1980 attttatag gaatagagga agaaatgtca gatgcgtgcc cagctcttca ccccccaatc   2040
tcttggtggg gagggtgta cctaaatatt tatcatatcc ttgcccttga gtgcttgtta   2100
gagagaaaga gaactactaa ggaaaataat attatttaaa ctcgctccta gtgtttcttt   2160
gtggtctgtg tcaccgtatc tcaggaagtc cagccacttg actggcacac acccctccgg   2220
acatccagcg tgacggagcc cacactgcca ccttgtggcc gcctgagacc ctcgcgcccc   2280
ccgcgccccc cgcgcccctc ttttccccct tgatggaaat tgaccataca atttcatcct   2340
ccttcagggg atcaaaagga cggagtgggg ggacagagac tcagatgagg acagagtggt   2400
ttccaatgtg ttcaatagat ttaggagcag aaatgcaagg ggctgcatga cctaccagga   2460
cagaactttc cccaattaca gggtgactca cagccgcatt ggtgactcac ttcaatgtgt   2520
catttccggc tgctgtgtgt gagcagtgga cacgtgaggg ggggtgggt gagagagaca   2580 ggcagctcgg attcaactac cttagataat atttctgaaa acctaccagc cagagggtag   2640
ggcacaaaga tggatgtaat gcactttggg aggccaaggc gggaggattg cttgagccca   2700
ggagttcaag accagcctgg gcaacatacc aagaccccg tctctttaaa aatatatata   2760
ttttaaatat acttaaatat atatttctaa tatctttaaa tatatatata tattttaaag   2820
accaatttat gggagaattg cacacagatg tgaaatgaat gtaatctaat agaagc      2876
```

<210> SEQ ID NO 22
<211> LENGTH: 1310
<212> TYPE: DNA

<213> ORGANISM: Homo sapiens

<400> SEQUENCE: 22

```
gctcggagcc cggagcgtgc ctcggcggcc tgtcggtttt caccatggag cagctgagct      60
cagcaaacac ccgcttcgcc ttggacctgt tcctggcgtt gagtgagaac aatccggctg     120
gaaacatctt catctctccc ttcagcattt catctgctat ggccatggtt tttctgggga     180
ccagaggtaa cacggcagca cagctgtcca agactttcca tttcaacacg gttgaagagg     240
ttcattcaag attccagagt ctgaatgctg atatcaacaa acgtggagcg tcttatattc     300
tgaaacttgc taatagatta tatggagaga aacttacaa tttccttcct gagttcttgg     360
tttcgactca gaaaacatat ggtgctgacc tggccagtgt ggattttcag catgcctctg     420
aagatgcaag aagaccata aaccagtggg tcaaaggaca gacagaagga aaaattccgg     480
aactgttggc ttcgggcatg gttgataaca tgaccaaact tgtgctagta atgccatctc    540
atttcaaggg aaactggaag gataaattca tgaaagaagc cacgacgaat gcaccattca     600
gattgaataa gaaagacaga aaaactgtga aaatgatgta tcagaagaaa aaatttgcat     660
atggctacat cgaggacctt aagtgccgtg tgctggaact gccttaccaa ggcgaggagc     720
tcagcatggt catcctgctg ccggatgaca ttgaggacga gtccacgggc ctgaagaaga     780
ttgaggaaca gttgacttg aaaagttgc atgagtggac taaacctgag aatctcgatt      840
tcattgaagt taatgtcagc ttgcccaggt tcaaactgga agagagttac actctcaact     900
ccgacctcgc ccgcctaggt gtgcaggatc tctttaacag tagcaaggct gatctgtctg     960
gcatgtcagg agccagagat attttttatat caaaaattgt ccacaagtca tttgtggaag    1020
tgaatgaaga gggaacagag gcggcagctg ccacagcagg catcgcaact ttctgcatgt    1080
tgatgcccga agaaaatttc actgccgacc atccattcct tttctttatt cggcataatt    1140
cctcaggtag catcctattc ttggggagat tttcttcccc ttagaagaaa gagactgtag    1200
caatacaaaa atcaagctta gtgctttatt acctgagttt ttaatagagc caatatgtct    1260
tatatcttta ccaataaaac cactgtccag aaaaaaaaaa aaaaaaaaa              1310
```

<210> SEQ ID NO 23
<211> LENGTH: 495
<212> TYPE: DNA
<213> ORGANISM: Homo sapiens
<220> FEATURE:
<221> NAME/KEY: misc_feature
<222> LOCATION: (488)..(488)
<223> OTHER INFORMATION: n is a, c, g, or t

<400> SEQUENCE: 23

```
tttgaatatt tatgtcaaat tacaaaccag tttaaagctg cctatttggc aaaatgatct      60
gctgcagaat tttcattttc tgtctctaga atgcagaaaa atgtcttaaa gttccttaat     120
ttgcttaatt taatgtggtt tccagaagat gtgaaaacct cctttatttt taaaatacct     180
gattccacat tggtcaatag tttcctcttt aatttacctc tctcctctca ctttatctat     240
aataagcagg gagaaatgaa gacacaccat caacacgttt gcttagatat gtcctcaact     300
aaatttctag tgtcacttac taattctaat ttcatccaat ataacataat taagataaat     360
tctataacaa gctacacata cttttccagtt ctaataccat gtttgtgatg gaaacaaagc    420
aggagtgccc tctgcaaggt gatcatctga gggtccaaga tgaaggggca cacaggtatt     480
ttatctgncc cacac                                                       495
```

<210> SEQ ID NO 24
<211> LENGTH: 488
<212> TYPE: DNA
<213> ORGANISM: Homo sapiens

<400> SEQUENCE: 24

```
ctgatatttt gtatattaat gaattatcca agattcgatg ggatttatca gtgtgtagat      60
agctctataa tgcttgaatt gtacacttct aagtgtgcag tgcaagagct tgtttatatt     120
tcatactttt tatactttga ggaaaaaaag tcaagaaaaa attgtatttg agggaaaaaa     180
ccatgaccaa gtaaaggata aattcaaaaa atagcctcat gagacttggc atacacactc     240
atgggattcc agttattatg gagtgcttcc atccctctcc accccttccc cccaaaaggt     300
tttctttgca agtgcttttg gaactaagag ctagtatctt ggattaactg atgcctgcta     360
gtgctttctg attactcgca ttctgtttct tgctttaaaa gaagagtaaa gacaagagtg     420
ttggaccagt attgcagttc tgtagtgtca tttcttataa aaacaaaac aacaacaata      480
atttatca                                                              488
```

<210> SEQ ID NO 25
<211> LENGTH: 1396
<212> TYPE: DNA
<213> ORGANISM: Homo sapiens

<400> SEQUENCE: 25

```
tgactatcca gctctgagag acgggagttt ggagttgccc gctttacttt ggttgggttg       60
gggggggcgg cgggctgttt tgttcctttt ctttttttaag agttgggttt tcttttttaa     120
ttatccaaac agtgggcagc ttcctccccc acacccaagt atttgcacaa tatttgtgcg     180
gggtatgggg gtgggttttt aaatctcgtt tctcttggac aagcacaggg atctcgttct     240
cctcatttt tgggggtgtg tgggggactt tcaggtcgtg tccccagcct tctctgcagt      300
cccttctgcc ctgccgggcc cgtcgggagg cgccatggct cggatgaacc gcccggcccc     360
ggtggaggtg agctacaaac acatgcgctt cctcatcacc cacaaccca caacgccac       420
gctcagcacc ttcattgagg acctgaagaa gtacgggggc accactgtgg tgcgtgtgtg     480
tgaagtgacc tatgacaaaa cgccgctgga aaggatggc atcaccgttg tggactggcc      540
gtttgacgat ggggcgcccc cgccggcaa ggtagtggaa gactggctga gcctggtgaa      600
ggccaagttc tgtgaggccc ccggcagctg cgtggctgtg cactgcgtgg cgggcctggg     660
ccgggctcca gtccttgtgg cgctggcgct tattgagagc gggatgaagt acaggacgc      720
catccagttc atccgccaga gcgccgcgg agccatcaac agcaagcagc tcacctacct     780
ggagaaatac cggcccaaac agaggctgcg gttcaaagac ccacacacgc acaagacccg     840
gtgctgcgtt atgtagctca ggaccttggc tgggcctggt cgtcatgtag gtcaggacct     900
tggctggacc tggaggccct gcccagccct gctctgccca gccagcagg ggctccaggc      960
cttggctggc cccacatcgc cttttcctcc ccgacacctc cgtgcacttg tgtccgagga    1020
gcgaggagcc cctcgggccc tgggtggcct ctgggccctt tctcctgtct ccgccactcc    1080
ctctggcggc gctggccgtg gctctgtctc tctgaggtgg gtcgggcgcc ctctgcccgc    1140
cccctcccac accagccagg ctggtctcct ctagcctgtt tgttgtgggg tgggggtata    1200
ttttgtaacc actgggcccc cagcccctct tttgcgaccc cttgtcctga cctgttctcg    1260
gcaccttaaa ttattagacc ccggggcagt caggtgctcc ggacaccga aggcaataaa    1320
acaggagccg tgaaaaaaaa aaaaaaaaaa aaaaaaaaaa aaaaaaaaaa aaaaaaaa      1380
```

-continued

| | |
|---|---:|
| aaaaaaaaaa aaaaaa | 1396 |

<210> SEQ ID NO 26
<211> LENGTH: 2294
<212> TYPE: DNA
<213> ORGANISM: Homo sapiens

<400> SEQUENCE: 26

| | |
|---|---:|
| aagcagttgt tttgctggaa ggagggagtg cgcgggctgc cccgggctcc tccctgccgc | 60 |
| ctcctctcag tggatggttc caggcaccct gtctgggca gggagggcac aggcctgcac | 120 |
| atcgaaggtg gggtgggacc aggctgcccc tcgccccagc atccaagtcc tcccttgggc | 180 |
| gcccgtggcc ctgcagactc tcagggctaa ggtcctctgt tgcttttgg ttccacctta | 240 |
| gaagaggctc cgcttgacta agagtagctt aaggaggca ccatgcagga gctgcatctg | 300 |
| ctctggtggg cgcttctcct gggcctggct caggcctgcc ctgagccctg cgactgtggg | 360 |
| gaaaagtatg gcttccagat cgccgactgt gcctaccgcg acctagaatc cgtgccgcct | 420 |
| ggcttcccgg ccaatgtgac tacactgagc ctgtcagcca accggctgcc aggcttgccg | 480 |
| gagggtgcct tcagggaggt gcccctgctg cagtcgctgt ggctggcaca caatgagatc | 540 |
| cgcacggtgg ccgccggagc cctggcctct ctgagccatc tcaagagcct ggacctcagc | 600 |
| cacaatctca tctctgactt tgcctggagc gacctgcaca acctcagtgc cctccaattg | 660 |
| ctcaagatgg acagcaacga gctgaccttc atccccgcg acgccttccg cagcctccgt | 720 |
| gctctgcgct cgctgcaact caaccacaac cgcttgcaca cattggccga gggcaccttc | 780 |
| accccgctca ccgcgctgtc ccacctgcag atcaacgaga ccccttcga ctgcacctgc | 840 |
| ggcatcgtgt ggctcaagac atgggcctg accacgccg tgtccatccc ggagcaggac | 900 |
| aacatcgcct gcacctcacc ccatgtgctc aagggtacgc cgctgagccg cctgccgcca | 960 |
| ctgccatgct cggcgccctc agtgcagctc agctaccaac ccagccagga tggtgccgag | 1020 |
| ctgcggcctg gttttgtgct ggcactgcac tgtgatgtgg acgggcagcc ggcccctcag | 1080 |
| cttcactggc acatccagat acccagtggc attgtggaga tcaccagccc caacgtgggc | 1140 |
| actgatgggc gtgccctgcc tggcacccct gtggccagct cccagccgcg cttccaggcc | 1200 |
| tttgccaatg gcagcctgct tatccccgac tttggcaagc tggaggaagg cacctacagc | 1260 |
| tgcctggcca ccaatgagct gggcagtgct gagagctcag tggacgtggc actggccacg | 1320 |
| cccgtgagg gtggtgagga cactgggg cgcaggttcc atggcaaagc ggttgaggga | 1380 |
| aagggctgct atacggttga caacgaggtg cagccatcag ggccggagga caatgtggtc | 1440 |
| atcatctacc tcagccgtgc tgggaaccct gaggctgcag tcgcagaagg ggtccctggg | 1500 |
| cagctgcccc caggcctgct cctgctgggc caaagcctcc tcctcttctt cttcctcacc | 1560 |
| tccttctagc cccacccagg gcttccctaa ctcctcccct tgcccctacc aatgcccctt | 1620 |
| taagtgctgc aggggtctgg ggttggcaac tcctgaggcc tgcatgggtg acttcacatt | 1680 |
| ttcctacctc tccttctaat ctcttctaga gcacctgcta tccccaactt ctagacctgc | 1740 |
| tccaaactag tgactaggat agaatttgat cccctaactc actgtctgcg gtgctcattg | 1800 |
| ctgctaacag cattgcctgt gctctcctct caggggcagc atgctaacgg gcgacgtcc | 1860 |
| taatccaact gggagaagcc tcagtggtgg aattccaggc actgtgactg tcaagctggc | 1920 |
| aagggccagg attgggggaa tggagctggg gcttagctgg gaggtggtct gaagcagaca | 1980 |
| gggaatggga gaggaggatg ggaagtagac agtggctggt atggctctga ggctccctgg | 2040 |
| ggcctgctca agctcctcct gctccttgct gttttctgat gatttggggg cttgggagtc | 2100 |

| | |
|---|---|
| cctttgtcct catctgagac tgaaatgtgg ggatccagga tggcttcctt cctcttaccc | 2160 |
| ttcctccctc agcctgcaac ctctatcctg gaacctgtcc tcccttctc cccaactatg | 2220 |
| catctgttgt ctgctcctct gcaaaggcca gccagcttgg gagcagcaga gaaataaaca | 2280 |
| gcatttctga tgcc | 2294 |

<210> SEQ ID NO 27
<211> LENGTH: 1399
<212> TYPE: DNA
<213> ORGANISM: Homo sapiens

<400> SEQUENCE: 27

| | |
|---|---|
| agtgtgaaat cttcagagaa gaatttctct ttagttcttt gcaagaaggt agagataaag | 60 |
| acacttttc aaaaatggca atggtatcag aattcctcaa gcaggcctgg tttattgaaa | 120 |
| atgaagagca ggaatatgtt caaactgtga agtcatccaa aggtggtccc ggatcagcgg | 180 |
| tgagcccta tcctaccttc aatccatcct cggatgtcgc tgccttgcat aaggccataa | 240 |
| tggttaaagg tgtggatgaa gcaaccatca ttgacattct aactaagcga aacaatgcac | 300 |
| agcgtcaaca gatcaaagca gcatatctcc aggaaacagg aaagcccctg gatgaaacac | 360 |
| ttaagaaagc ccttacaggt caccttgagg aggttgtttt agctctgcta aaaactccag | 420 |
| cgcaatttga tgctgatgaa cttcgtgctg ccatgaaggg ccttggaact gatgaagata | 480 |
| ctctaattga gattttggca tcaagaacta caaagaaat cagagacatt aacagggtct | 540 |
| acagagagga actgaagaga gatctggcca agacataac ctcagacaca tctggagatt | 600 |
| ttcggaacgc tttgctttct cttgctaagg gtgaccgatc tgaggacttt ggtgtgaatg | 660 |
| aagacttggc tgattcagat gccagggcct tgtatgaagc aggagaaagg agaaggggga | 720 |
| cagacgtaaa cgtgttcaat accatcctta ccaccagaag ctatccacaa cttcgcagag | 780 |
| tgtttcagaa atacaccaag tacagtaagc atgcatgaa caaagttctg gacctggagt | 840 |
| tgaaaggtga cattgagaaa tgcctcacag ctatcgtgaa gtgcgccaca agcaaaccag | 900 |
| cttttctttgc agagaagctt catcaagcca tgaaggtgt tggaactcgc cataaggcat | 960 |
| tgatcaggat tatggtttcc cgttctgaaa ttgacatgaa tgatatcaaa gcattctatc | 1020 |
| agaagatgta tggtatctcc ctttgccaag ccatcctgga tgaaaccaaa ggagattatg | 1080 |
| agaaaatcct ggtggctctt tgtggaggaa actaaacatt cccttgatgg tctcaagcta | 1140 |
| tgatcagaag actttaatta tatttttca tcctataagc ttaaatagga agtttcttc | 1200 |
| aacaggatta cagtgtagct acctacatgc tgaaaaatat agcctttaaa tcatttttat | 1260 |
| attataactc tgtataatag agataagtcc attttttaaa aatgttttcc ccaaaccata | 1320 |
| aaaccctata caagttgttc tagtaacaat acatgagaaa gatgtctatg tagctgaaaa | 1380 |
| taaaatgacg tcacaagac | 1399 |

<210> SEQ ID NO 28
<211> LENGTH: 3088
<212> TYPE: DNA
<213> ORGANISM: Homo sapiens

<400> SEQUENCE: 28

| | |
|---|---|
| acaaaaaagc ttttacgagg tatcagcact tttctttcat taggggaag gcgtgaggaa | 60 |
| agtaccaaac agcagcggag ttttaaactt taaatagaca ggtctgagtg cctgaacttg | 120 |
| ccttttcatt ttacttcatc ctccaaggag ttcaatcact tggcgtgact tcactactt | 180 |

```
taagcaaaag agtggtgccc aggcaacatg ggtgactgga gcgccttagg caaactcctt      240
gacaaggttc aagcctactc aactgctgga gggaaggtgt ggctgtcagt acttttcatt      300
ttccgaatcc tgctgctggg gacagcggtt gagtcagcct ggggagatga gcagtctgcc      360
tttcgttgta acactcagca acctggttgt gaaaatgtct gctatgacaa gtctttccca      420
atctctcatg tgcgcttctg ggtcctgcag atcatatttg tgtctgtacc cacactcttg      480
tacctggctc atgtgttcta tgtgatgcga aggaagagaa aactgaacaa gaaagaggaa      540
gaactcaagg ttgcccaaac tgatggtgtc aatgtggaca tgcacttgaa gcagattgag      600
ataaagaagt tcaagtacgg tattgaagag catggtaagg tgaaaatgcg ggggggttg       660 ctgcgaacct acatcatcag tatcctcttc aagtctatct ttgaggtggc cttcttgctg      720
atccagtggt acatctatgg attcagcttg agtgctgttt acacttgcaa aagagatccc      780
tgcccacatc aggtggactg tttcctctct cgccccacgg agaaaaccat cttcatcatc      840
ttcatgctgg tggtgtcctt ggtgtccctg gccttgaata tcattgaact cttctatgtt      900
ttcttcaagg gcgttaagga tcgggttaag ggaaagagcg acccttacca tgcgaccagt      960
ggtgcgctga gccctgccaa agactgtggg tctcaaaaat atgcttattt caatggctgc     1020
tcctcaccaa ccgctcccct ctcgcctatg tctcctcctg ggtacaagct ggttactggc     1080
gacagaaaca attcttcttg ccgcaattac aacaagcaag caagtgagca aaactgggct     1140
aattacagtg cagaacaaaa tcgaatgggg caggcgggaa gcaccatctc taactcccat     1200
gcacagcctt ttgatttccc cgatgataac cagaattcta aaaaactagc tgctggacat     1260
gaattacagc cactagccat tgtggaccag cgaccttcaa gcagagccag cagtcgtgcc     1320
agcagcagac ctcggcctga tgacctggag atctagatac aggcttgaaa gcatcaagat     1380
tccactcaat tgtggagaag aaaaaaggtg ctgtagaaag tgcaccaggt gttaattttg     1440
atccggtgga ggtggtactc aacagcctta ttcatgaggc ttagaaaaca caagacatt      1500 agaataccta ggttcactgg gggtgtatgg ggtagatggg tggagaggga ggggataaga     1560
gaggtgcatg ttggtattta agtagtgga ttcaaagaac ttagattata aataagagtt      1620
ccattaggtg atacatagat aagggctttt tctccccgca acaccccta agaatggttc      1680 tgtgtatgtg aatgagcggg tggtaattgt ggctaaatat ttttgtttta ccaagaaact     1740
gaaataattc tggccaggaa taaatacttc ctgaacatct taggtctttt caacaagaaa     1800
aagacagagg attgtcctta agtccctgct aaaacattcc attgttaaaa tttgcacttt     1860
gaaggtaagc tttctaggcc tgaccctcca ggtgtcaatg gacttgtgct actatatttt     1920
tttattcttg gtatcagttt aaaattcaga caaggcccac agaataagat tttccatgca     1980
tttgcaaata cgtatattct ttttccatcc acttgcacaa tatcattacc atcacttttt     2040
catcattcct cagctactac tcacattcat ttaatggttt ctgtaaacat ttttaagaca     2100
gttgggatgt cacttaacat ttttttttttt tgagctaaag tcagggaatc aagccatgct     2160
taatatttaa caatcactta tatgtgtgtc gaagagtttg ttttgtttgt catgtattgg     2220
tacaagcaga tacagtataa actcacaaac acagatttga aaataatgca catatggtgt     2280
tcaaatttga accttctctca tggattttttg tggtgtgggc caatatggtg tttacattat     2340
ataattcctg ctgtgcaag taaagcacac tttttttttc tcctaaaatg tttttccctg      2400
tgtatcctat tatggatact ggttttgtta attatgattc tttattttct ctccttttt      2460 taggatatag cagtaatgct attactgaaa tgaatttcct ttttctgaaa tgtaatcatt     2520
gatgcttgaa tgatagaatt ttagtactgt aaacaggctt tagtcattaa tgtgagagac     2580
```

```
ttagaaaaaa tgcttagagt ggactattaa atgtgcctaa atgaattttg cagtaactgg    2640
tattcttggg ttttcctact aatacacag taattcagaa cttgtattct attatgagtt    2700
tagcagtctt ttggagtgac cagcaacttt gatgtttgca ctaagatttt atttggaatg    2760
caagagaggt tgaaagagga ttcagtagta cacatacaac taatttattt gaactatatg    2820
ttgaagacat ctaccagttt ctccaaatgc cttttttaaa actcatcaca gaagattggg    2880
gaaaatgctg agtatgacac ttttcttctt gcatgcatgt cagctacata aacagttttg    2940
tacaatgaaa attactaatt tgtttgacat tccatgttaa actacggtca tgttcagctt    3000
cattgcatgt aatgtagacc tagtccatca gatcatgtgt tctggagagt gttctttatt    3060
caataaagtt ttaatttagt ataaacat                                     3088
```

```
<210> SEQ ID NO 29
<211> LENGTH: 403
<212> TYPE: DNA
<213> ORGANISM: Homo sapiens

<400> SEQUENCE: 29
tttcattagt tatcattagt ttattataaa agagaaatat ggaaattatt tacatgacga     60
aagatttcag aacttcagtg gaatgggcag catcatgttg atgccatttc aatagtgact    120
tatttcagtc tacgtacttt ccaagaatgt caccatctct aaataggaaa taatccttgt    180
catctagaac tactttggtg cctccatatt ctgggagaag aactttatct ccaactttca    240
cgctaactgg ttgaatctct ccacccttc ctttagaacc cgatccaaca gcgactactg    300
ttgcttgcaa tacttttcct tgagattttt ctggaagcat aatgcctcct ttggttacag    360
tttcagcagc actcctttca accaatactc ggtcaaagag tgg                     403
```

```
<210> SEQ ID NO 30
<211> LENGTH: 1023
<212> TYPE: DNA
<213> ORGANISM: Homo sapiens

<400> SEQUENCE: 30
gttggctgcc ggtgagttgg gtgccggtgg agtcgtgttg gtcctcagaa tccccgcgta     60
gccgctgcct cctcctaccc tcgccatgtt tcttacccgg tctgagtacg acaggggcgt    120
gaatactttt tctcccgaag aagattatt tcaagtggaa tatgccattg aggctatcaa    180
gcttggttct acagccattg ggatccagac atcagagggt gtgtgcctag ctgtggagaa    240
gagaattact tcccactga tggagcccag cagcattgag aaaattgtag agattgatgc    300
tcacataggt tgtgccatga gtgggctaat tgctgatgct aagactttaa ttgataaagc    360
cagagtggag acacagaacc actggttcac ctacaatgag acaatgacag tggagagtgt    420
gacccaagct gtgtccaatc tggctttgca gtttggagaa gagatgcag atccaggtgc    480 catgtctcgt cccttttggag tagcattatt atttggagga gttgatgaga aaggacccca    540 gctgttcat atggacccat ctgggacctt tgtacagtgt gatgctcgag caattggctc    600
tgcttcagag ggtgcccaga gctccttgca agaagtttac cacaagtcta tgactttgaa    660
agaagccatc aagtcttcac tcatcatcct caaacaagta atggaggaga agctgaatgc    720
aacaaacatt gagctagcca cagtgcagcc tggccagaat ttccacatgt tcacaaagga    780
agaacttgaa gaggttatca aggacattta aggaatcctg atcctcagaa cttctctggg    840
acaatttcag ttctaataat gtccttaaat tttatttcca gctcctgttc cttggaaaat    900
```

```
ctccattgta tgtgcatttt ttaaatgatg tctgtacata aaggcagttc tgaaataaag    960 aaaatttttaa aataaaaaaa aaaaaaaaaa aaaaaaaaaa aaaaaaaaaa             1020
aaa                                                                  1023
```

<210> SEQ ID NO 31
<211> LENGTH: 313
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t

<400> SEQUENCE: 31

```
ntcttgggct caagcaancc tcctgccctg gcttcccaaa gtgttcagat tacaagtgtg      60
agccactgca cccagaccaa gaaattttaa ccctaactaa atacccaaaa aaagngtata     120
tatgttccac aaaggacatg ggtaagaatg tttatagcag cagtatttgt aatagccaga    180
aactggaaac aagccaaaca tctatctaca gcagaagaga ctattgttta tttatacaat    240
aaactacaat ataggcaata aaatgantga ggctacaaca acaggaaatc aatttcacaa    300
acatantact gag                                                       313
```

<210> SEQ ID NO 32
<211> LENGTH: 358
<212> TYPE: DNA
<213> ORGANISM: Homo sapiens
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t

<400> SEQUENCE: 32

```
tgttaagtac ttaagattta ttgaatgaga actgcattgt acaatatggt gccactagac      60
acgtctattt aatttaaatt aaaatataaa actctaaaac tagccatgat tcaaaggttc     120
aatagctata tgtgactagt ggctaccata taaaacattt ccatcacaaa gttccattta    180
tcagatctta tataggaacc ttgantaaaa tttaatagac aagtgatttt gtatttaaca    240
tttcaccttt attgaatgcc ctataggggcc atttgaatac gggtcatgtn caaggcacag    300
```

```
gggaaaaaaa aactgcagcn ggtaagggtt ttncaggggg gttttccagg tccccctcc      358
```

```
<210> SEQ ID NO 33
<211> LENGTH: 326
<212> TYPE: DNA
<213> ORGANISM: Homo sapiens
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t

<400> SEQUENCE: 33
ttnnatatta nttattttt  attatacttt aagttttagg gtacatgtgc acaatgtcag       60
ggtttgttac atatgtatgg gcaaggactt catgtctaaa acaccaaaag caatggcaac      120
aaaagccaaa attgacaaaa gtagtatcat tctattatag ctgcatggaa aaagttaatt      180
tattaataca atggatgcct aaggncagaa gtactcaaac ttttggtctc agtactcctt      240
tacattctta aaaatcatta nggncccccaa ngantgtttg tttacaaggg ttacttacat      300
tgataattac cacatttgaa atgaaa                                           326
```

```
<210> SEQ ID NO 34
<211> LENGTH: 2301
<212> TYPE: DNA
<213> ORGANISM: Homo sapiens

<400> SEQUENCE: 34
tcgacagctc tctcgcccag cccagttctg gaagggataa aaaggggca tcaccgttcc        60 tgggtaacag agccaccttc tgcgtcctgc tgagctctgt tctctccagc acctcccaac      120
ccactagtgc ctggttctct tgctccacca ggaacaagcc accatgtctc gccagtcaag      180
tgtgtccttc cggagcgggg gcagtcgtag cttcagcacc gcctctgcca tcacccgtc      240 tgtctcccgc accagcttca cctccgtgtc ccggtccggg ggtggcggtg gtggtggctt      300
cggcagggtc agccttgcgg gtgcttgtgg agtgggtggc tatggcagcc ggagcctcta      360
caacctgggg ggctccaaga ggatatccat cagcactaga ggaggcagct tcaggaaccg      420
gtttggtgct ggtgctggag gcggctatgg ctttggaggt ggtgccggta gtggatttgg      480
tttcggcggt ggagctggtg gtggcttggg gctcggtggc ggagctggct ttggaggtgg      540
cttcggtggc cctggctttc ctgtctgccc tcctggaggt atccaagagg tcactgtcaa      600
```

-continued

```
ccagagtctc ctgactcccc tcaacctgca aatcgacccc agcatccaga gggtgaggac      660
cgaggagcgc gagcagatca agaccctcaa caataagttt gcctccttca tcgacaaggt      720
gcggttcctg gagcagcaga acaaggttct ggacaccaag tggaccctgc tgcaggagca      780
gggcaccaag actgtgaggc agaacctgga gccgttgttc gagcagtaca tcaacaacct      840
caggaggcag ctggacagca tcgtggggga acggggccgc ctggactcag agctgagaaa      900
catgcaggac ctggtggaag acttcaagaa caagtatgag gatgaaatca acaagcgtac      960
cactgctgag aatgagtttg tgatgctgaa gaggatgta gatgctgcct acatgaacaa     1020
ggtggagctg gaggccaagg ttgatgcact gatggatgag attaacttca tgaagatgtt     1080
ctttgatgcg gagctgtccc agatgcagac gcatgtctct gacacctcag tggtcctctc     1140
catgacaaac aaccgcaacc tggacctgga tagcatcatc gctgaggtca aggcccagta     1200
tgaggagatt gccaaccgca gccggacaga agccgagtcc tggtatcaga ccaagtatga     1260
ggagctgcag cagacagctg gccggcatgg cgatgacctc cgcaacacca agcatgagat     1320
cacagagatg aaccggatga tccagaggct gagagccgag attgacaatg tcaagaaaca     1380
gtgcgccaat ctgcagaacg ccattgcgga tgccgagcag cgtggggagc tggccctcaa     1440
ggatgccagg aacaagctgg ccgagctgga ggaggccctg cagaaggcca gcaggacat     1500
ggcccggctg ctgcgtgagt accaggagct catgaacacc aagctggccc tggacgtgga     1560
gatcgccact taccgcaagc tgctggaggg cgaggaatgc agactcagtg agaaggagt     1620
tggaccagtc aacatctctg ttgtcacaag cagtgtttcc tctggatatg gcagtggcag     1680
tggctatggc ggtggcctcg gtggaggtct tggcggcggc ctcggtggag gtcttgccgg     1740
aggtagcagt ggaagctact actccagcag cagtgggggt gtcggcctag gtggtgggct     1800
cagtgtgggg ggctctggct tcagtgcaag cagtggccga gggctggggg tgggctttgg     1860
cagtggcggg ggtagcagct ccagcgtcaa atttgtctcc accacctcct cctcccggaa     1920
gagcttcaag agctaagaac ctgctgcaag tcactgcctt ccaagtgcag caacccagcc     1980
catggagatt gcctcttcta ggcagttgct caagccatgt tttatccttt tctggagagt     2040
agtctagacc aagccaattg cagaaccaca ttctttggtt cccaggagag ccccattccc     2100
agccctggt ctccgtgcc gcagttctat attctgcttc aaatcagcct tcaggtttcc     2160
cacagcatgg cccctgctga cacgagaacc caaagttttc ccaaatctaa atcatcaaaa     2220
cagaatcccc accccaatcc caaattttgt tttggttcta actacctcca gaatgtgttc     2280
aataaaatgc ttttataata t                                               2301
```

<210> SEQ ID NO 35
<211> LENGTH: 448
<212> TYPE: DNA
<213> ORGANISM: Homo sapiens
<220> FEATURE:
<221> NAME/KEY: misc_feature
<222> LOCATION: (437)..(437)
<223> OTHER INFORMATION: n is a, c, g, or t

<400> SEQUENCE: 35

```
gatcatatta ttaaataata tatgcacaga catggagaga attagttttt actaaaacat       60
ttatcagaaa ttttaatact ctgcataacc agtattagca ttagaaatta gccactttta      120
aaatgagaaa actgtgtcac tcttcaattt ttttataagc cattgaggaa aacattaact      180
cctggatttc agcttcactt ttaacctgca gactaaattt cttttctcaat tatgtcagac      240
acacccaagt caatcccaac cccttgttta ccttgggaag acccgtgctg aaaaaggaga      300
```

```
tcttccacct aaacacgtgt tctcttattt gaagcaaatc ttttgagaa tttgtttact    360 tgatttcttt ccacaataaa ctgacagaga acgctactaa tgattttttt ttttttttgg    420
agacggggtt tgttcntgg ttggccca                                        448
```

```
<210> SEQ ID NO 36
<211> LENGTH: 219
<212> TYPE: DNA
<213> ORGANISM: Homo sapiens
<220> FEATURE:
<221> NAME/KEY: misc_feature
<222> LOCATION: (39)..(39)
<223> OTHER INFORMATION: n is a, c, g, or t

<400> SEQUENCE: 36 tgttttttg aagtgactga ctaaaaagag aacagatana tacaagagtg tcgctggatc     60
ctattttata caaggattac gcctctcctg cttggcccctt actgtcaccc tgtacaggta   120
caaaggctac aaaaaaggaa gcaatataaa cagacacaaa taacttttttt gcttttttac   180 atgcgatttg taagcttagt ttgagctatt cacaagcta                           219
```

```
<210> SEQ ID NO 37
<211> LENGTH: 2808
<212> TYPE: DNA
<213> ORGANISM: Homo sapiens

<400> SEQUENCE: 37
cggcatgaga ggccagcctg ccagggaaat ccaggaatct gcaacaaaaa cgatgacagt     60
ctgaaatact ctctggtgcc aacctccaaa ttctcgtctg tcacttcaga cccccactag    120
ttgacagagc agcagaatat caactccagt agacttgaat gtgcctctgg gcaaagaagc    180
agagctaacg aggaagggga tttaaagagt ttttcttggg tgtttgtcaa acttttattc    240
cctgtctgtg tgcagagggg attcaacttc aattttctgc agtggctctg ggtccagccc    300
cttacttaaa gatctggaaa gcatgaagac tgggcctttt ttcctatgtc tcttgggaac    360
tgcagctgca atcccgacaa atgcaagatt attatctgat cattccaaac caactgctga    420
aacggtagca cctgacaaca ctgcaatccc cagtttatgg gctgaagctg aagaaaatga    480
aaaagaaaca gcagtatcca cagaagacga ttcccaccat aaggctgaaa atcatcagt    540 actaaagtca aaagaggaaa gccatgaaca gtcagcagaa cagggcaaga ttctagcca    600 agagctggga ttgaaggatc aagaggacag tgatggtcac ttaagtgtga atttggagta    660
tgcaccaact gaaggtacat tggacataaa agaagatatg attgagcctc aggagaaaaa    720
actctcagag aacactgatt ttttggctcc tggtgttagt tccttcacag attctaacca    780
acaagaaagt atcacaaaga gagggaaaa ccaagaacaa cctagaaatt attcacatca    840
tcagttgaac aggagcagta acatagcca aggcctaagg gatcaaggaa ccaagagca    900 ggatccaaat atttccaatg gagaagagga agaagaaaaa gagccaggtg aagttggtac    960
ccacaatgat aaccaagaaa gaaagacaga attgcccagg gagcatgcta acagcaagca   1020
ggaggaagac aatacccaat ctgatgatat tttggaagag tctgatcaac caactcaagt   1080
aagcaagatg caggaggatg aatttgatca gggtaaccaa gaacaagaag ataactccaa   1140
tgcagaaatg gaagaggaaa atgcatcgaa cgtcaataag cacattcaag aaactgaatg   1200
gcagagtcaa gagggtaaaa ctggcctaga agctatcagc aaccacaaag agacagaaga   1260
aaagactgtt tctgaggctc tgctcatgga acctactgat gatggtaata ccacgcccag   1320
```

```
aaatcatgga gttgatgatg atggcgatga tgatggcgat gatggcggca ctgatggccc    1380
caggcacagt gcaagtgatg actacttcat cccaagccag gcctttctgg aggccgagag    1440
agctcaatcc attgcctatc acctcaaaat tgaggagcaa agagaaaaag tacatgaaaa    1500
tgaaaatata ggtaccactg agcctggaga gcaccaagag gccaagaaag cagagaactc    1560
atcaaatgag gaggaaacgt caagtgaagg caacatgagg gtgcatgctg tggattcttg    1620
catgagcttc cagtgtaaaa gaggccacat ctgtaaggca gaccaacagg gaaaacctca    1680
ctgtgtctgc caggatccag tgacttgtcc tccaacaaaa cccttgatc aagtttgtgg    1740 cactgacaat cagacctatg ctagttcctg tcatctattc gctactaaat gcagactgga    1800
ggggaccaaa aaggggcatc aactccagct ggattatttt ggagcctgca aatctattcc    1860
tacttgtacg gactttgaag tgattcagtt tcctctacgg atgagagact ggctcaagaa    1920
tatcctcatg cagctttatg aagccaactc tgaacatgct ggttatctaa atgagaagca    1980
gagaaataaa gtcaagaaaa tttacctgga tgaaagagg cttttggctg gggaccatcc    2040
cattgatctt ctcttaaggg actttaagaa aaactaccac atgtatgtgt atcctgtgca    2100
ctggcagttt agtgaacttg accaacaccc tatggataga gtcttgacac attctgaact    2160
tgctcctctg cgagcatctc tggtgcccat ggaacactgc ataacccgtt tctttgagga    2220
gtgtgacccc aacaaggata agcacatcac cctgaaggag tggggccact gctttggaat    2280
taaagaagag gacatagatg aaaatctctt gttttgaacg aagattttaa agaactcaac    2340
tttccagcat cctcctctgt tctaaccact tcagaaatat atgcagctgt gatacttgta    2400
gatttatatt tagcaaaatg ttagcatgta tgacaagaca atgagagtaa ttgcttgaca    2460
acaacctatg caccaggtat ttaacattaa ctttggaaac aaaaatgtac aattaagtaa    2520
agtcaacata tgcaaaatac tgtacattgt gaacagaagt ttaattcata gtaatttcac    2580
tctctgcatt gacttatgag ataattaatg attaaactat taatgataaa aataatgcat    2640
ttgtattgtt cataatatca tgtgcacttc aagaaaatgg aatgctactc ttttgtggtt    2700
tacgtgtatt attttcaata tcttaatacc ctaataaaga gtccataaaa atccaaaaaa    2760
aaaaaaaaaa aaaaaaaaa aaaaaaaaaa aaaaaaaaaa aaaaaaaa                  2808
```

<210> SEQ ID NO 38
<211> LENGTH: 416
<212> TYPE: DNA
<213> ORGANISM: Homo sapiens
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (285)..(286)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t

```
<220> FEATURE:
<221> NAME/KEY: misc_feature
<222> LOCATION: (353)..(353)
<223> OTHER INFORMATION: n is a, c, g, or t

<400> SEQUENCE: 38
tttatttnnt tgaatctatt taattgctca gactgtgcta gagaatacgt accatgaaat      60
acatatattt cataaggttc agttacaaaa tggattgttt caaatggcaa tttcttacac     120
taacctgatt atgaaaaaaa gaagtctgta tcatctgctt ccaagtctgt tatgtccaaa     180
tatattttaa ttatgcattt attttgctac ttttataaat attagagatt tcaccntaaa     240
ttatttttgt aactagttct agaacatgtt tnccaattat tattnnccta atgggagaca     300
tataattgac cnatggttta tggcatatat ggtcctctac acagnggaac ctnttttttaa    360 aaggaatagg taaaggaaaa tgcgggacgg cctgggctct ccagggccaa gggcca        416

<210> SEQ ID NO 39
<211> LENGTH: 471
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t

<400> SEQUENCE: 39
tttttntttt tttaaagtga atatacaatt tatttaacat tcaaacttca ttaagacatg      60
tgcaatatgg caattttact ggggattaaa ccctacctag gattgcttgc tggggcttag     120
caacagggtc cagttcacac ttagcactaa ttaaatactt tattgaataa atacaatacc     180
angcaaaatg cattcaaatg ctttctaaaa aaatttttaaa ggcctttcta ctcaggctaa     240
tgacaaacac aataaaggca gatatgctag tttaacataa ttgggctgat tttatacagg     300
cacttatatc ttttagtcca caaggtatat tattaaatga tagggaaaca tctnatacaa     360
ccatttctac agnactaggg gaattaaatt tctatgggaa ggaagggttt ttacagaccc     420
catctttttt taccncccccc aacagttcta actctaaggg ggttatagcc a             471

<210> SEQ ID NO 40
<211> LENGTH: 525
<212> TYPE: DNA
<213> ORGANISM: Homo sapiens

<400> SEQUENCE: 40
tttttttttt tttttttttg aaattttaac attttatatg catataaagc tgaacacatg      60
actaacaatc tagtggatgt gtatagaacc caacaattgc agaatatata ttcttttcaa     120
gcacacattg aatattttata aaaactgatc atatactgtg ccgtaagttt catctcagca    180
```

```
aatttcaaag ttttgatgcc atgaatgaaa tgaaacctga catttcaaaa ttataaacag    240
aatatgccct ggagtaactt gtggtattgt ttggggatga ggagagccat ccgaatagtg    300
ttttaaggaa agtctctatt cattgatctg gggtaacaag gcaggaacca ttccaatgca    360
gaagctttgg ctaagcagtt gagcgttcag tagtgcatgt aaattcctgt gtgaaggctg    420
tggtgtcatg gctaaaggca tagcccctgg aacccagact gtttgggttc aaatctcagt    480
tctgctgctt aactcactgt gtgatggtgg gcaagttgcc taacc                   525

<210> SEQ ID NO 41
<211> LENGTH: 1402
<212> TYPE: DNA
<213> ORGANISM: Homo sapiens

<400> SEQUENCE: 41
ggggacgaag ggaagctcca gcgtgtggcc ccggcgagtg cggataaaag ccgccccgcc     60
gggctcgggc ttcattctga gccgagcccg gtgccaagcg cagctagctc agcaggcggc    120
agcggcggcc tgagcttcag ggcagccagc tccctcccgg tctcgccttc cctcgcggtc    180
agcatgaaag ccttcagtcc cgtgaggtcc gttaggaaaa acagcctgtc ggaccacagc    240
ctgggcatct cccggagcaa aacccctgtg gacgacccga tgagcctgct atacaacatg    300
aacgactgct actccaagct caaggagctg gtgcccagca tcccccagaa caagaaggtg    360
agcaagatgg aaatcctgca gcacgtcatc gactacatct tggacctgca gatcgccctg    420
gactcgcatc ccactattgt cagcctgcat caccagagac ccgggcagaa ccaggcgtcc    480
aggacgccgc tgaccaccct caacacggat atcagcatcc tgtccttgca ggcttctgaa    540
ttcccttctg agttaatgtc aaatgacagc aaagcactgt gtggctgaat aagcggtgtt    600
catgatttct tttattcttt gcacaacaac aacaacaaca aattcacgga atcttttaag    660
tgctgaactt attttttcaac catttcacaa ggaggacaag ttgaatggac ctttttaaaa    720
agaaaaaaaa aatggaagga aaactaagaa tgatcatctt cccagggtgt tctcttactt    780
ggactgtgat attcgttatt tatgaaaaag acttttaaat gcccttttctg cagttggaag   840 gttttcttta tatactattc ccaccatggg gagcgaaaac gttaaaatca caaggaattg    900
cccaatctaa gcagactttg ccttttttca aaggtggagc gtgaatacca gaaggatcca    960
gtattcagtc acttaaatga agtcttttgg tcagaaatta cctttttgac acaagcctac   1020
tgaatgctgt gtatatattt atatataaat atatctattt gagtgaaacc ttgtgaactc   1080
tttaattaga gttttcttgt atagtggcag agatgtctat ttctgcattc aaaagtgtaa   1140
tgatgtactt attcatgcta aactttttat aaaagtttag ttgtaaactt aaccctttta   1200
tacaaaataa atcaagtgtg tttattgaat ggtgattgcc tgctttattt cagaggacca   1260
gtgctttgat ttttattatg ctatgttata actgaaccca aataaataca agttcaaatt   1320
tatgtagact gtataagatt ataataaaac atgtctgaag tcaaaaaaaa aaaaaaaaa    1380 aaaaaaaaa aaaaaaaaa aa                                             1402

<210> SEQ ID NO 42
<211> LENGTH: 2544
<212> TYPE: DNA
<213> ORGANISM: Homo sapiens

<400> SEQUENCE: 42
ctcactcaga cccatgaggc cctgcctggt ctcgtctggg acctgggaca gcagctggga     60
gacctgagcc tggagtctgg gggcctggaa caggagagcg ggcgtagctc gggcttctat    120
```

```
gaagatccca gctctacagg aggtccagat tcaccaccct caaccttctg tggggacagt    180
ggcttctctg gatccagctc ctatggtcgc ctgggtccct ctgagccccg ggcatctat     240 gccagtgaga ggcccaagtc cctaggagac gccagtccca gcgctccgga ggtggtgggc    300
gcgcgggcag cggtgccgcg gtccttctca gcgccctacc cgacggcagg tgggtcgccg    360 gccccggaggc ctgctcctcg gcggagcggc gggcccgcgc cgggccccttt ctgacgccca   420 gccccctgca cgccgtggcg atgcgcagcc cgcggccctg cggccgccct cccaccgact    480
cgcccgacgc gggggggcgca gggcggcccc tggacggcta catctcggcg ctcctgcgca   540
ggcgccgccg ccggggggcg ggccagcccc ggaccagtcc tgggggcgcg gacggcggcc    600
cgcggcgcca aacagcgtg cgccagcggc cgcccgacgc gtctccgtcc ccggcagcg     660 cgcgacccgc gcgggagccc tcgttggagc gcgtcggggg ccaccccacc agccctgccg    720
ccttgagccg cgcctgggcg tcgtcgtggg agtcggaggc ggcacccgag cccgctgcgc    780
cgcccgccgc cccctcaccc cccgacagcc cggctgaggg ccgcttggtg aaggcgcagt    840
acatcccggg cgcgcaggcg gccacccgag gcctccctgg ccgcgccgcc cgccgcaaac    900
cgccgccact gacccgcggc cgcagcgtgg agcagtcacc accccgggag cgtccccggg    960
ccgccggccg ccgtggacgc atggccgagg cttcgggccg ccgcggctcg cccagggccc    1020
gcaaggcctc gcgctcccag tctgagacca ggctgctggg ccgcgcctcc gcggtccctt    1080
cggggccccc taagtacccc acggcggagc gggaagagcc tcggcctcca cggccacgcc    1140
gcggcccagc gcccacgctg gcggcccagg ccgcagggtc ctgccgtcgc tggcgctcca    1200
ctgcggagat cgacgctgcc gatgggcgcc gcgtgcggcc ccgagcccct gcggcgcgtg    1260
ttcccggccc cggcccgtcc ccgtcagctc cccagcgtcg tctgctttac ggctgcgcgg    1320
gcagcgactc cgagtgctcg gctgggcgcc tggggcccct gggacgccgg gggcctgcgg    1380
gaggcgtcgg cggggttac ggggagagcg aatcgagcgc cagcgaggga gaatcgcctg     1440
ccttcagctc tgcctccagc gactcagacg gcagcggtgg cctcgtgtgg ccgcagcagc    1500
tggtggcgga caccgcggcc tctggggggtg gagcaggtgc aggggcgccc gcaggccccg    1560
ccaaagtctt cgtgaaaatc aaagcttccc acgcgctcaa gaaaaagata ctgcgtttcc    1620
gttcgggttc tctcaaggtc atgactacag tgtgagtttg gggatttgct tgggctcccc    1680
cttcatggcc tctgcacctc cacactccca accactgacc cttccacatc taccttccaa    1740
agaccatcgt tttctctgct tccaaagacc ccctcactc tccccactcc taacagtctt     1800
ggttgaaaag ctcccccac caccaccgag aggaatgggg aggagccctg tttgacccag      1860
ttcagcttct agcttggaag cccttgggca agacagttcc ccttctctgg gcgtcacttt    1920
cctcatctgt acagtaagtg tccatgtatg caaaaggggt aattcggttt gaatttcccc    1980
gttttagttt agaagcctag tctgtttgtt cccccttcacc gctctccctc tcattcctga   2040
tgagccctct cattcctcct ttccttgccc agctatggcc ccctctcatt cacaaagtgc    2100
cccctccatg tccctggacc cttaagatat ccccttggca ccctggtcag agactctgtg    2160
tctgactcag gtggtccctg cagagtgccc tgggaaggga aggagcactg atttgggggt    2220
tttgagggtc aagtaggggt tggtaacacc tggaaagaag gactctttca cttcgatccc    2280
tggacaatta tggaggattc ggaggtagaa gaggggaagg aagatggttt ctatctcatg    2340 accccccactc cctgtgagag ggaatggggg aagcctgatg accctcagct gttccaatct   2400
agtatttttt ttcttttttta aaattactgt atttattatg acgatggtga ctccccagtg   2460
```

```
caaaggggggg ccagattctg tgtgtttctc taacctctttt gtaaataaat gcacagtgta    2520
acataaaaaa aaaaaaaaaa aaaa                                             2544

<210> SEQ ID NO 43
<211> LENGTH: 374
<212> TYPE: DNA
<213> ORGANISM: Homo sapiens
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t

<400> SEQUENCE: 43
aagcattaga gaagcatcag gccgccattc tagactcaac tgctcacctc ctctgatcca      60
ctgaggtgtc tctggaaatc ctccaccaca gccacagcct cctcaccact ctcagggtga    120
tgcagctgca cccaggtccg agctcccca gggaggatgc tcaggaactg ctcaagcacc     180
agcagctcca ggatctgctc cttggtgtgc acctctgggc atgagccacc agcggcagag    240
cttcccgaag ccggctcaat gctttcctgc ggcccagaca tctcgtgggt aacacaattg    300
cctgaagtgt aggccggaag attttcgcag acaggaggat agttnttttt gggagattgt    360
tggccttgnc ccca                                                       374

<210> SEQ ID NO 44
<211> LENGTH: 4299
<212> TYPE: DNA
<213> ORGANISM: Homo sapiens

<400> SEQUENCE: 44
tgacagcgga ggcggcggcg gctgcaggct ccgagccgta ggagccggat cgggggaggg      60
gccgggccca ggagcctcag ccccgccggc agccctaagg gcaaggtaac cgccacgggg    120
tccccgtcgc gacccctcc ctcccggagc tccgtcccc gggatcccaa gctccgcccc      180
gccgaccccc gtctcccctg gaccccggct ctagcctgac gagatcccca acctcctgag    240
gtgctctggc cccggattct cccgggctgc attctctgct cctcctcgcc tgcgaagcat    300
cacgtccgct tcccgacgct gagggcagcc ccgtccaggg cagtggctct gccaatgatc    360
ctgtgagtat tcaggaatca ctgttgcccc tggggatcct tgtcctggag tggcccacct    420
gcttgccccc agcatggcgt ccgacactcc cgagtcgctg atggccctct gtactgactt    480
ctgcttgcgc aacctggatg gcaccctggg ctacctgctg gacaaggaga ccctgcggct    540
acatccggac atcttcttgc ccagcgagat ctgtgaccgg ctcgtcaatg agtatgtgga    600
gctggtgaac gctgcctgta acttcgagcc acacgagagc ttcttcagcc tcttttcgga    660 ccccgcagc acccgcctca cgcggatcca cctccgtgag gacctggtgc aggaccagga    720
cctggaggcc atccgcaagc aggacctggt ggagctgtac ctgactaact gcgagaagct    780
gtccgccaag agcctgcaga cactgaggag cttcagccac accctggtgt ccttgagcct    840
cttcggctgt acaaacattt tctatgagga ggagaaccca gggggctgtg aagatgagta    900
cctcgtcaac cccaccctgcc aggtgctggt taaggatttc accttcgagg cttcagccg    960 cctccgcttc ctcaacttgg gccgcatgat tgattgggtc cctgtggagt ccctgctgcg    1020
gccgcttaac tccctggctg ccttggacct tcaggcatt cagacgagcg acgccgcctt    1080
cctcacccag tggaaagaca gcctggtgtc cctcgtcctc tacaacatgg acctgtccga    1140
```

```
cgaccacatc cgggtcatcg tgcagctgca caagctgcga cacctggaca tctcccgaga    1200
ccgcctctcc agctactaca agttcaagct gactcgggag gtgctgagcc tctttgtgca    1260
gaagctgggg aacctaatgt ccctggacat ctctggccac atgatcctag agaactgcag    1320
catctccaag atggaagagg aagcggggca gaccagcatt gagccttcca agagcagcat    1380
catacctttc cgggctctga gaggccgct gcagttcctc gggctctttg agaactctct    1440
gtgccgcctc acgcacattc cagcctacaa agtaagtggt gacaaaaacg aagagcaggt    1500
gctgaatgcc atcgaggcct acacggagca ccggcctgag atcacctcgc gggccatcaa    1560
cttgctttttt gacatcgccc gcatcgagcg ttgcaaccag ctgctgcggg ccctgaagct    1620
ggtcatcacg gccctcaagt gccacaaata tgacaggaac attcaagtga caggcagcgc    1680
cgctctcttc tacctaacaa attccgagta ccgctcagag cagagtgtga agctgcgccg    1740
gcaggttatc caggtggtgc tgaatggcat ggaatcctac caggaggtga cggtgcagcg    1800
gaactgctgc ctgacgctct gcaacttcag catccccgag gagctggaat ccagtaccg    1860
ccgggtcaac gagctcctgc tcagcatcct caaccccacg cggcaggacg agtctatcca    1920
gcggatcgcc gtgcacctgt gcaatgccct ggtctgccag gtagacaacg accacaagga    1980
ggccgtgggc aagatgggct tgtcgtgac catgctgaag ctgattcaga gaagctgct    2040
ggacaagaca tgtgaccagg tcatggagtt ctcctggagt gccctgtgga acatcacaga    2100
tgaaactcct gacaactgcg agatgttcct caatttcaac ggcatgaagc tcttcctgga    2160
ctgcctgaag gaattcccag agaagcagga actgcatagg aatatgctag acttttggg    2220
gaatgtggca gaagtgaagg agctgaggcc tcaactaatg acttcccagt tcatcagcgt    2280
cttcagcaac ctgttggaga gcaaggccga tgggatcgag gtttcctaca atgcctgcgg    2340
cgtcctctcc cacatcatgt ttgatggacc cgaggcctgg ggcgtctgtg agccccagcg    2400
tgaggaggtg gaggaacgca tgtgggctgc catccagagc tgggacataa actctcggag    2460
aaacatcaat tacaggtcat ttgaaccaat tctccgcctc cttccccagg gaatctctcc    2520
tgtcagccag cactgggcaa cctgggcct gtataacctc gtgtctgtct acccggacaa    2580
gtactgccct ctgctgatca agaaggggg gatgcccctt ctgagggaca taattaagat    2640
ggcgaccgca cggcaggaga ccaaggaaat ggcccgcaag gtgattgagc actgcagtaa    2700
ctttaaagag gagaacatgg acacgtctag atagaggcct ccgtcccat ggccgccacc    2760
gctctggacc acaggcgggg aggaagcatg ctcaagcagc ccagcgggcg ggccccttcc    2820
gagggagcct cccacggagt gaagagacat ggggacttt tgcacaaccg acgcttttcc    2880
ttaatgttag tgagatatat atatattata tatatatt ttttttttgg ttaggaagtg    2940
tgaagttttg tgtgtatgat ttctgtgcaa aaacaaaagc aacactcctg agtccttgca    3000
gcttccttgg ccattctcaa acccactcag ccttcatcgc tgacacacac actcctaccc    3060
caaccagact aaatgcctat aacgctgtga gtgtccagtc cttgtccagg aaactcagat    3120
cccggcctgg cttcctttca tgagaggagc aggccttgga cagcgtatcg agcatcctga    3180
cccactgccc ctgcctgaga acgccatctc ggctcccggg cacagctgat ggggtttggg    3240
gattagaact taccccactg ggtctcccaa aagccttggt gctcccggct gtgggccatc    3300
tggggcagga aagtgagcca ttcctaggct gaggtccagg cagccctgcc cctgaagacc    3360
ctctaggagc agggcaccca gtgggccctg ctgctgtccag ccaggcctgc ctgaggccac    3420
gctgctatgg aggctgcctc ctagtctccc accaggtccc aggctgtgga aagccccagc    3480
```

-continued

```
ccagggatgg tcagaactcg ggggcagatt ccactgcccc ttctgccaaa cacatccaga    3540
acctgccctc agccctggaa gctagcatct tctggggcca ggggcttgct tcctcgctcc    3600
atagccctca actgcccagg cgctcccacc agcagaactg agcctgcctc ctcctcccag    3660
cctgccccgc tgcccagagg accccacgcc tctcagaggc agaggtccca tgccagcctt    3720
tgacccacaa cggccacaca gccgcctcca gaccagcact cggactgccc tgcagtggcc    3780
gcttgggcct ccctggcggt cccgccctgc cctaggcttt accttggaag cctgagaggc    3840
gccggctctc ttgctcctcc atcgatggac actgcattgc ttctcatcgg acacttgtgg    3900
agcgcagggg cctggggagc agcgctaacc ctggaggcag cctttgggtg atggcttttt    3960
cttccctttt cctcccgcgg gcctgttttc aggtgttcct agcatttctg cctccaggca    4020
ggacggcagg ggtgagcagc tttgggagag acacctggcc tttttctcct ggagcctctc    4080
cctcccggcc ctgggaagtg ggcgcagccc tgtgttcccc cagcttggca gatgggctgc    4140
atgcggcgct cccttccttc ccacgctcag cggccccggc cagaccctgg cagacttcac    4200
acctcattgc tttaccccct ggggcctggg gaaatgtctg tactttggga agtcacagaa    4260
atacattttt gtgcaaaatg gaaaaaaaaa aaaaaaaaa                           4299
```

<210> SEQ ID NO 45
<211> LENGTH: 6990
<212> TYPE: DNA
<213> ORGANISM: Homo sapiens

<400> SEQUENCE: 45

```
atggctgaga gcgcctcccc gccctcctca tctgcagcag ccccagccgc tgagccagga      60
gtcaccacgg agcagcccgg accccggagc ccccatcct ccccgccagg cctggaggag      120
cctctggatg gagctgatcc tcatgtccca cacccagacc tggcgcctat tgccttcttc      180
tgcctgcgac agaccaccag cccccggaac tggtgcatca agatggtgtg caacccgtgg      240
tttgaatgtg tcagcatgct ggtgatcctg ctgaactgcg tgacacttgg catgtaccag      300
ccgtgcgacg acatggactg cctgtccgac cgctgcaaga tcctgcaggt ctttgatgac      360
ttcatcttta tcttctttgc catggagatg gtgctcaaga tggtggccct ggggattttt      420
ggcaagaagt gctacctcgg ggacacatgg aaccgcctgg atttcttcat cgtcatggca      480
gggatggtcg agtactccct ggaccttcag aacatcaacc tgtcagccat ccgcaccgtg      540
cgcgtcctga ggcccctcaa agccatcaac cgcgtgccca gtatgcggat cctggtgaac      600
ctgctcctgg acacactgcc catgctgggg aatgtcctgc tgctctgctt ctttgtcttc      660
ttcatctttg gcatcatagg tgtgcagctc tgggcgggcc tgctgcgtaa ccgctgcttc      720
ctggaggaga acttcaccat acaaggggat gtggccttgc ccccatacta ccagccggag      780
gaggatgatg agatgccctt catctgctcc ctgtcgggcg acaatgggat aatgggctgc      840
catgagatcc ccccgctcaa ggagcagggc cgtgagtgct gcctgtccaa ggacgacgtc      900
tacgactttg ggcgggggcg ccaggacctc aatgccagcg gcctctgtgt caactggaac      960
cgttactaca atgtgtgccg cacgggcagc gccaacccc acaagggtgc catcaacttt     1020
gacaacatcg gttatgcttg gattgtcatc ttccaggtga tcactctgga aggctgggtg     1080
gagatcatgt actacgtgat ggatgctcac tccttctaca acttcatcta cttcatcctg     1140
cttatcatag tgggctccct cttcatgatc aacctgtgcc tcgttgtcat agcgacccag     1200 ttctcgggaga ccaagcaacg ggagcaccgg ctgatgctgg agcagcggca gcgctacctg     1260
tcctccagca cggtggccag ctacgccgag cctggcgact gctacgagga gatcttccag     1320
```

```
tatgtctgcc acatcctgcg caaggccaag cgccgcgccc tgggcctcta ccaggccctg   1380
cagagccggc gccaggccct gggcccggag gccccggccc ccgccaaacc tgggccccac   1440
gccaaggagc cccggcacta ccatgggaag actaagggtc agggagatga agggagacat   1500
ctcggaagcc ggcattgcca gactttgcat gggcctgcct cccctggaaa tgatcactcg   1560
ggaagagagc tgtgcccgca acatagcccc ctggatgcga cgcccacac cctggtgcag    1620 cccatccccg ccacgctggc ttccgatccc gccagctgcc cttgctgcca gcatgaggac   1680
ggccggcggc cctcgggcct gggcagcacc gactcgggcc aggagggctc gggctccggg   1740
agctccgctg gtggcgagga cgaggcggat ggggacgggg cccggagcag cgaggacgga   1800
gcctcctcag aactggggaa ggaggaggag gaggaggagc aggcggatgg ggcggtctgg   1860
ctgtgcgggg atgtgtggcg ggagacgcga gccaagctgc gcggcatcgt ggacagcaag   1920
tacttcaacc ggggcatcat gatggccatc ctggtcaaca ccgtcagcat gggcatcgag   1980
caccacgagc agccggagga gctgaccaac atcctggaga tctgcaatgt ggtcttcacc   2040
agcatgtttg ccctggagat gatcctgaag ctggctgcat ttgggctctt cgactacctg   2100
cgtaacccct acaacatctt cgacagcatc attgtcatca tcagcatctg ggagatcgtg   2160
gggcaggcgg acggtgggct gtcggtgctg cggaccttcc ggctgctgcg cgtgctgaaa   2220
ctggtgcgct tcatgcctgc cctgcggcgc cagctcgtgg tgctcatgaa gaccatggac   2280
aacgtggcca ccttctgcat gctgctcatg ctcttcatct tcatcttcag catccttggg   2340
atgcatattt ttggctgcaa gttcagcctc cgcacggaca ctggagacac ggtgcccgac   2400
aggaagaact cgactcccct gctgtgggcc atcgtcactg tgttccagat cctcacccag   2460
gaggactgga acgtcgttct ctacaatggc atggcctcca cttctccctg gcctccctc    2520 tactttgtcg ccctcatgac cttcggcaac tatgtgctct tcaacctgct ggtggccatc   2580
ctggtggagg gcttccaggc ggagggtgac gccaatcgct cctactcgga cgaggaccag   2640
agctcatcca acatagaaga gtttgataag ctccaggaag gcctggacag cagcggagat   2700
cccaagctct gcccaatccc catgacccc aatgggcacc tggaccccag tctcccactg    2760
ggtgggcacc taggtcctgc tggggctgcg ggacctgccc ccgactctc actgcagccg     2820 gaccccatgc tggtggccct gggctcccga aagagcagtg tcatgtctct agggaggatg   2880
agctatgacc agcgctccct gtccagctcc cggagctcct actacgggcc atggggccgc   2940
agcgcggcct gggccagccg tcgctccagc tggaacagcc tcaagcacaa gccgcgtcg    3000 gcggagcatg agtccctgct ctctgcggag cgcggcggcg gcgcccgggt ctgcgaggtt   3060
gccgcggacg agggggccgcc gcgggccgca ccctgcaca ccccacacgc ccaccacatt    3120
catcacgggc cccatctggc gcaccgccac cgccaccacc gccggacgct gtccctcgac   3180
aacagggact cggtggacct ggccgagctg gtgcccgcgg tgggcgccca ccccggggcc   3240
gcctggaggg cggcaggccc ggccccgggg catgaggact gcaatggcag gatgcccagc   3300
atcgccaaag acgtcttcac caagatgggc gaccgcgggg atcgcgggga ggatgaggag   3360
gaaatcgact acacctgtg cttccgcgtc cgcaagatga tcgacgtcta taagcccgac    3420
tggtgcgagg tccgcgaaga ctggtctgtc tacctcttct ctcccgagaa caggttccgg   3480
gtcctgtgtc agaccattat tgcccacaaa ctcttcgact acgtcgtcct ggccttcatc   3540
tttctcaact gcatcaccat cgccctggag cggcctcaga tcgaggcgg cagcaccgaa   3600 cgcatctttc tcaccgtgtc caactacatc ttcacggcca tcttcgtggg cgagatgaca   3660
```

```
ttgaaggtag tctcgctggg cctgtacttc ggcgagcagg cgtacctacg cagcagctgg    3720
aacgtgctgg atggctttct tgtcttcgtg tccatcatcg acatcgtggt gtccctggcc    3780
tcagccgggg gagccaagat cttgggggtc ctccgagtct tgcggctcct gcgcacccta    3840
cgccccctgc gtgtcatcag ccgggcgccg ggcctgaagc tggtggtgga gacactcatc    3900
tcctccctca agcccatcgg caacatcgtg ctcatctgct gtgccttctt catcatcttt    3960
ggcatcctgg gagtgcagct cttcaagggc aagttctacc actgtctggg cgtggacacc    4020
cgcaacatca ccaaccgctc ggactgcatg gccgccaact accgctgggt ccatcacaaa    4080
tacaacttcg acaacctggg ccaggctctg atgtccctct tgtcctggc atccaaggat     4140 ggttgggtga acatcatgta caatggactg gatgctgttg ctgtggacca gcagcctgtg    4200
accaaccaca cccctggat gctgctgtac ttcatctcct tcctgctcat cgtcagcttc     4260
tttgtgctca acatgtttgt gggtgtcgtg gtggagaact ccacaagtg ccggcagcac     4320 caggaggctg aagaggcacg gcggcgtgag gagaagcggc tgcggcgcct ggagaagaag    4380
cgccggaagg cccagcggct gccctactat gccacctatt gtcacacccg gctgctcatc    4440
cactccatgt gcaccagcca ctacctggac atcttcatca ccttcatcat ctgcctcaac    4500
gtggtcacca tgtccctgga gcactacaat cagcccacgt ccctggagac agccctcaag    4560
tactgcaact atatgttcac cactgtcttt gtgctggagg ctgtgctgaa gctggtggca    4620
tttggtctga ggcgcttctt caaggaccga tggaaccagc tggacctggc cattgtgcta    4680
ctgtcagtca tgggcatcac cctggaggag atcgagatca atgcggccct gcccatcaat    4740
cccaccatca tccgcatcat gagggttctg cgcattgccc gagtgctgaa gctgttgaag    4800
atggccacag gaatgcgggc cctgctggac acggtggtgc aagctttgcc ccaggtgggc    4860
aacctgggcc tcctcttcat gctgctcttc ttcatctatg ctgctctcgg ggtggagctc    4920
tttgggaagc tggtctgcaa cgacgagaac ccgtgcgagg gcatgagccg gcatgccacc    4980
ttcgagaact tcggcatggc cttcctcaca ctcttccagg tctccacggg tgacaactgg    5040
aacgggatca tgaaggacac gctgcgggac tgcacccacg acgagcgcag ctgcctgagc    5100
agcctgcagt ttgtgtcgcc gctgtacttc gtgagcttcg tgctcaccgc gcagttcgtg    5160
ctcatcaacg tggtggtggc tgtgctcatg aagcacctgg acgacagcaa caaggaggcg    5220
caggaggacg ccgagatgga tgccgagctc gagctggaga tggcccatgg cctgggccct    5280
ggcccgaggc tgcctaccgg ctccccgggc gcccctggcc gagggccggg aggggcgggc    5340 ggcggggcg acaccgaggg cggcttgtgc cggcgctgct actcgcctgc ccaggagaac    5400
ctgtggctgg acagcgtctc tttaatcatc aaggactcct tggaggggga gctgaccatc    5460
atcgacaacc tgtcgggctc catcttccac cactactcct cgcctgccgg ctgcaagaag    5520
tgtcaccacg acaagcaaga ggtgcagctg gctgagacgg aggccttctc cctgaactca    5580
gacaggtcct cgtccatcct gctgggtgac gacctgagtc tcgaggaccc cacagcctgc    5640
ccacctggcc gcaaagacag caagggtgag ctggacccac ctgagcccat gcgtgtggga    5700
gacctgggcg aatgcttctt ccccttgtcc tctacggccg tctcgccgga tccagagaac    5760
ttcctgtgtg agatggagga gatcccattc aaccctgtcc ggtcctggct gaaacatgac    5820
agcagtcaag caccccaag tcccttctcc ccggatgcct ccagccctct cctgcccatg    5880
ccagccgagt tcttccaccc tgcagtgtct gccagccaga aaggcccaga aaagggcact    5940
ggcactggaa ccctccccaa gattgcgctg cagggctcct gggcatctct gcggtcacca    6000
agggtcaact gtaccctcct ccggcaggcc accgggagcg acacgtcgct ggacgccagc    6060
```

```
cccagcagct ccgcgggcag cctgcagacc acgctcgagg acagcctgac cctgagcgac      6120 agccccggc gtgccctggg gccgccgcg cctgctccag accccgggc cggcctgtcc         6180 cccgccgctc gccgccgcct gagcctgcgc ggccggggcc tcttcagcct gcggggggctg     6240 cgggcgcatc agcgcagcca cagcagcggg ggctccacca gcccgggctg cacccaccac     6300
gactccatgg accctcgga cgaggagggc gcggtggcg cgggcggcgg gggcgcgggc       6360
agcgagcact cggagaccct cagcagcctc tcgctcacct ccctcttctg cccgccgccc     6420
ccgccgccag ccccggcct cacgcccgcc aggaagttca gcagcaccag cagcctggcc     6480 gccccggcc gccccacgc cgccgccctg gcccacggcc tggcccggag ccctcgtgg       6540 gccgcggacc gcagcaagga ccccccggc cgggcaccgc tgcccatggg cctgggcccc     6600
ttggcgcccc cgccgcaacc gctccccgga gagctggagc cgggagacgc cgccagcaag    6660
aggaagagat gagggtcgca ggggccccg ccgcccacc gccgccccg tctcaccttc       6720 tttacctcag gagccaggag cagacagcaa tacttcgtcc acacctggga tcgcgcaggg    6780
cccgcagggc acaggcgccc gacagccggg ctgagcggag tctgggttag ccaggcctgc    6840
gtggcccatg gtggcccttc cagtgcatat acatacatat atatatatat atgcatatat    6900
atatatatat atatatatat gtgtatacac acacacatag acagacatat atatatatat   6960
ttattttttt tactgagagc ttatgacttc                                      6990

<210> SEQ ID NO 46
<211> LENGTH: 139
<212> TYPE: DNA
<213> ORGANISM: Homo sapiens
<220> FEATURE:
<221> NAME/KEY: misc_feature
<222> LOCATION: (138)..(138)
<223> OTHER INFORMATION: n is a, c, g, or t

<400> SEQUENCE: 46
ctaatatttg catgtacaca atgagttatc ttagggaggg gatccaagtg gaaacacaaa      60
atttattttt gtgtgtatac acacatacac acatcactta tatacatagc cttaaggtaa    120
ttttataccg tattttttng                                                 139

<210> SEQ ID NO 47
<211> LENGTH: 674
<212> TYPE: DNA
<213> ORGANISM: Homo sapiens

<400> SEQUENCE: 47 cccctttggtt ccgcccgcgc gtcacgtgac cccagcgcct acttgggctg aggagccgcc      60
gcgtcccctc gccgagtccc ctcgccagat tccctccgtc gccgccaaga tgatgtgcgg     120
ggcgccctcc gccacgcagc cggccaccgc cgagacccag cacatcgccg accaggtgag     180
gtcccagctt gaagagaaag aaaacaagaa gttccctgtg tttaaggccg tgtcattcaa     240
gagccaggtg gtcgcgggga caaactactt catcaaggtg cacgtcggcg acgaggactt     300
cgtacacctg cgagtgttcc aatctctccc tcatgaaaac aagcccttga ccttatctaa     360
ctaccagacc aacaaagcca agcatgatga gctgacctat ttctgatcct gactttggac     420
aaggcccttc agccagaaga ctgacaaagt catcctccgt ctaccagagc gtgcacttgt     480
gatcctaaaa taagcttcat ctccgggctg tgcccttgg ggtggaaggg gcaggattct     540
gcagctgctt ttgcatttct cttcctaaat ttcattgtgt tgatttcttt ccttcccaat    600
```

| aggtgatctt aattactttc agaatatttt caaaatagat atatttttaa aatccttaaa | 660 |
| aaaaaaaaaa aaaa | 674 |

<210> SEQ ID NO 48
<211> LENGTH: 6276
<212> TYPE: DNA
<213> ORGANISM: Homo sapiens

<400> SEQUENCE: 48

| agtcggcatc catcagcggg cggggtgtc gccgaacagg ctgctccgca gagcccgccg | 60 |
| cgaccccgcg ccgccccgcc ccgcggcctg cctgccagag gagccgaggg ggccgccccct | 120 |
| cgcccaacct gcccgacatg gggaacccccg ggcccaggcg tgctggtcac catgacaaca | 180 |
| gagacaggcc ccgactctga ggtgaagaaa gctcaggagg aggccccgca gcagcccgag | 240 |
| gctgctgccg ctgtgaccac ccctgtgacc cctgcaggcc acggccaccc agaggccaac | 300 |
| tccaatgaga agcatccatc ccagcaggac acgcggcctg ctgaacagag cctagacatg | 360 |
| gaggagaagg actacagtga ggccgatggc cttcggaga ggaccacgcc cagcaaggcc | 420 |
| cagaaatcgc cccagaagat tgccaagaaa tacaagagtg ccatctgccg ggtcactctg | 480 |
| cttgatgcct cggagtatga gtgtgaggtg gagaaacatg gccggggcca ggtgctgttt | 540 |
| gacctggtct gtgaacacct caacctccta gagaaggact acttcggcct gaccttctgt | 600 |
| gatgctgaca gccagaagaa ctggctggac ccctccaagg agatcaagaa gcagatccgg | 660 |
| agtagcccct ggaattttgc cttcacagtc aagttctacc cgcctgatcc tgcccagctg | 720 |
| acagaagaca tcacaagata ctacctgtgc ctgcagctgc gggcagacat catcacgggc | 780 |
| cggctgccat gctcctttgt cacgcatgcc ctactgggct cctacgctgt gcaggctgag | 840 |
| ctgggtgact atgatgctga ggagcatgtg ggcaactatg tcagcgagct ccgcttcgcc | 900 |
| cctaaccaga cccgggagct ggaggagagg atcatggagc tgcataagac atatagggg | 960 |
| atgaccccgg gagaagcaga aatccacttc ttagagaatg ccaagaagct ttccatgtac | 1020 |
| ggagtagacc tgcaccatgc caaggactct gagggcatcg acatcatgtt aggcgtttgt | 1080 |
| gccaatggcc tgctcatcta ccgggaccgg ctgagaatca accgctttgc ctggcccaag | 1140 |
| atcctcaaga tctcctacaa gaggagtaac ttctatatca agatccggcc tggggagtat | 1200 |
| gagcaatttg agagcacaat tggctttaag ctcccaaacc accggtcagc caagagactg | 1260 |
| tggaaggtct gcatcgagca tcatacattc ttccggctgg tgtcccctga gcccccaccc | 1320 |
| aagggcttcc tggtgatggg ctccaagttc cggtacagtg gaggaccca ggcacagact | 1380 |
| cgccaggcca gcgccctcat tgaccggcct gcacccttct tgagcgttc ttccagcaaa | 1440 |
| cggtacacca tgtcccgcag ccttgatgga gcagagttcc ccgcccagc ctcggtcagc | 1500 |
| gagaaccatg atgcagggcc tgacggtgac aagcgggatg aggatggcga gtctggggg | 1560 |
| caacggtcag aggctgagga gggagaggtc aggactccaa ccaagatcaa ggagctaaag | 1620 |
| ccggagcagg aaaccacgcc gagacacaag caggagttct tagacaagcc agaagatgtc | 1680 |
| ttgctgaagc accaggccag catcaatgag ctcaaaagga ccctgaagga gcccaacagc | 1740 |
| aaactcatcc accgggatcg agactgggaa cgggagcgca ggctgccctc ctcccccgcc | 1800 |
| tccccctccc caagggcac ccctgagaaa gccaatgaga gagcagggct gagggagggc | 1860 |
| tccgaggaga aagtcaaacc accacgtccc cgggcccag agagtgacac aggcgatgag | 1920 |
| gaccaggacc aggagaggga cacggtgttc ctgaaggaca accacctggc cattgagcgc | 1980 |
| aagtgctcca gcatcacggt cagctctacg tctagcctgg aggctgaggt ggacttcacg | 2040 |

```
gtcattggtg actaccatgg cagcgccttc gaagacttct cccgcagcct gcctgagctc    2100
gaccgggaca aaagcgactc ggacactgag ggcctgctgt tctcccggga tctcaacaag    2160
ggggccccca gccaggatga tgagtctggg ggcattgagg acagcccgga tcgaggggcc    2220
tgctccaccc cggatatgcc ccagtttgag cccgtgaaaa cagaaaccat gactgtcagc    2280
agtctggcca ttagaaagaa gattgagccg gaggccgtac tgcagaccag agtctccgct    2340
atggataaca cccagcaggt tgatgggagt gcctcagtgg ggagggagtt catagcaacc    2400
actccctcca tcaccacgga gaccatatcg accaccatgg agaacagtct caagtccggg    2460 aaggggggcag ctgccatgat cccaggccca cagacggtgg ccacggaaat ccgttctctt    2520
tctccgatca tcgggaaaga tgtcctcacc agcacctacg cgccactgc ggaaaccctc     2580 tcaacctcca ccaccaccca tgtcaccaaa actgtgaaag gagggttttc tgagacaagg    2640
atcgagaagc gaatcatcat tactggggat gaagatgtcg atcaagacca ggccctggct    2700
ttggccatca aggaggccaa actgcagcat cctgatatgc tggtaaccaa agctgtcgta    2760
tacagagaaa cagacccatc cccagaggag agggacaaga agccacagga atcctgacct    2820
ctgtgaagag atcctggcat ttctggtcca acccaagcca gagaaccatt aagaagggc     2880 cttcattctg gattctccga cgcaacactg acgtccagc tgcgacgtac tgtcactgat      2940
gagagactgg gaagggaaaa gcatatatat atagatatat agagatatag atatatatac    3000
aggaaacacc gcatccttgc actgctgctg gggctggcag agcagttggc tgacagcaac    3060
aaccgacatc tgaacaccta catttccttt gcagacaaat tgaagaactg gtgggatttt    3120
tttcaagaaa aaaaattata taataactat aatcccttgc tcaccccttt ccccgccaa     3180 ataagaaacg caagccagac cacgatgatt gtagaagtcc ctcccgccct ggttctgcac    3240
gttacagtta gcagacgagc aattccattt gttcttctcc agcatctcta aggcccactt    3300
gaatgcaaag gaaaacactt gcacagcaaa gcaagagaag tcacagcagc aagacacgca    3360
cagtcaacca ttttccgaga aaaaagaaa attccccact tggaaagaaa gaggaggaac    3420
actggattct tactttctgg atcttgacac tgggctgcaa aacctacctt cctctctccc    3480
gcctcccctc accctcaact ctcaatgtct tgctgtcatt ttctgtctcg gctccctcct    3540
cccccttccc ccttccccca ccccacaccc ttcaccctct gtgtcctggt ccttctgagg    3600
gccactgcag atgactctcc tttgaaatga gaaaagaaa agaaagcaag aacagaaaac    3660
gaagccacag gaagggaagt agacattgta tgcttatggt ttctcattat gaaggtgcag    3720
cttgtaggag gttttgtacgg atgtgctttg aagttatgta tattacatat aacaggaaaa    3780
aatattaaaa taaacagtgc tggtaagtat gaagctgaca ttctaaaatt ataattatct    3840
gactgtgatt gatgtatcct gaggttccta gatctcactg aactggccca gctaaggaga    3900
cctggactct gggtgtgggt tggctcacag taggggctga cgggttcagt gtagtaatac    3960
tgtgtgtggt gtttgtaatt ggttgattgg tggggagggg tggggggccc taatggagag    4020
gtgtgggttt ggcaagaaag aagcaacaca gatgtcgtcc ccaaaatgcc agttcaagac    4080
accttctccc tgcccccctg gtagtaacag tcagggcctg gtctgtgctc aggtactggg    4140
tcccagtctg ggactctgct gctgaagttg ccacagtaga ggtccctggc ttagtcctta    4200
tctccctacg gggcttgcct tggttttcag tcttctctct ctttctctct tttttttttt    4260
tttgccacat tctgcccttc cctgacccca ttgtaataac caactccata tccaagggga   4320
ggtggtgctc tcagccattg tagaagatgg tggctttaac ctgactgtct aaaaattccc    4380
```

```
agctaagcct tttcctctac tctcttcctt gttctgaatc atttcttctt ctcaggccaa      4440
agtagccatg gtaaggaggc ttcatggggc agaccctgaa agatcaaaac tgcatttgca      4500
aagccctccc ctgtcccagg acaaagctga gactgacggg tgatgttgct cataggctcc      4560
agctctgcat aagaccttgg cttggagacc tccctctcag tcaacagctg aactctgagc      4620
ttgtgcccag aaattacccc aagaccacag gaacccttca agaagctccc atcacaagct      4680
tggcattgct ctctgccaca cgtgggcttc ctcaggcttg tctgccacaa gctacttctc      4740
tgagctcaga aagtgcccct tgatgaggga aaatgtccca ctgcactgcg aatttctcag      4800
ttccatttta cctcccagtc ctccttctaa accagttaat aaattcattc cacaagtatt      4860
tactgattac ctgcttgtgc cagggactat tctcaggctg aagaaggtgg gaggggaggg      4920
cggaacctga ggagccacct gagccagctt tatatttcaa ccatggctgg cccatctgag      4980
agcatctccc cactctcgcc aacctatcgg ggcatagccc agggatgccc ccaggcggcc      5040
caggttagat gcgtcccttt ggcttgtcag tgatgacata caccttagct gcttagctgg      5100
tgctggcctg aggcagggca ggaaatcaga atagcatttg cttctctggg caaatgggaa      5160
gttcagcggg gcagcagaat cagtggcatt ccccctggtg caggccggtg ggtccactcc      5220 aactcccccct gagtgtagca gcacactttc catacaccag gttctttcta caatcctggt      5280
ggaaaagcca cagaaccttc ttcctgccct tcttgagagt tcccctctt tctgggtcaa      5340 gagctggagt ggtggctcca tcctctctgg gccacttcgg tctaggaact catctttgca      5400
ggaaccagga gtcctgagca cactgaacac acctcagagg gaggatcctt gttgtggatt      5460
ttgcacctgg ctttggggca ggggtgaagt gaccaggctt agcttgtgga gtttatgggc      5520
caccagggtt tggggaaatc accatcccgc ggatgctgtg acctcccttc tacggagatg      5580
caggcagtgc cacgagggag gaggggacct gcaaagctag aatctagggc actgtttcct      5640
ccccatcctt ctctttgtag agaatagaga cgtttgtctt gtctgtcttc aacctacttt      5700
tccttttctc ttttttgttt ctcatcctct ctgtgccacc tctccaccca ggaggccatg      5760
tagcatagtg gaaaaagtcc ctgagggcgg ttaggagttc tgggtgacca tcctggctca      5820
gctcctaact caccatgtga catcaggcta tccccattcc ccctcttggg cctcagtttc      5880
ccgacttgca aaataagcag aaagaaccag atgctctcca gggtcttttt ctactttgct      5940
atctcatggg tcttcatttt ctcttatttt gttttctctg gatcttttcc atctgagggt      6000
acaggaagta ccaggacctg tttcagtttt tgaatcctgc aagcacattc caagactggc      6060
ctgaaactgc atgagcaaca tcactcgaaa taatttttt tttcaaaagc accttaacaa      6120
ccaattgcga tgctgtcctg ttcctttta ctcacaccct tctctccttt ctcgtcccca      6180
tgctccccca cctcagtgct ccgtgctgta tgcgtgtgct ctctgttctt gtatactcaa      6240
tataagtgaa ataaatgtgt ttgatgctga accata                                6276
```

<210> SEQ ID NO 49
<211> LENGTH: 982
<212> TYPE: DNA
<213> ORGANISM: Homo sapiens

<400> SEQUENCE: 49

```
ggctcatcca cctgcagaca tggggcgcag aaagtcaaaa cgaaagccgc ctcccaagaa        60
gaagatgaca ggcaccctcg agacccagtt cacctgcccc ttctgcaacc acgagaaatc       120
ctgtgatgtg aaaatggacc gtgcccgcaa caccggagtc atctcttgta ccgtgtgcct       180
agaggaattc cagacgccca taacgtatct gtcagaaccc gtggatgtgt acagtgattg       240
```

```
gatagacgcc tgcgaggcgg ccaatcagta gcgacacaga ggacccgccc cctgagcagc      300
cccgcgtact gtggatccag ctgttcggtt ctggtccaga gacattccag gggtccaggg      360
tgtgggtcct gggctgtcac agccgtgtgt gtgtgtgtgt gtgtgtgtgt gtgtgtgtgt      420
gtgtgtgtag tgggtgtgcg tgtgggtgtg ggtgtgagtg agtgtgggtg tgtgtggctg      480
cacgtgtcac tggggtggcc gtgagtgtgt gctcacaggt acgcggtggt gtcgggttcc      540
tgggcctgag gggcctgaac tgatctcact tggctccgaa agcctttgct gtgttccctg      600
cagcccctgg cccccagcc ttggggctct ggctcccccc ggcggaattg ggggactgtt       660
tcctgacatc ctggacaagg gaagcccact agaggctgga acaggacctc tccagcctcc      720
tcaccagcac cgtgcccatc tcaactggac ttcccgccct ccttctccac cttctagtgc      780
ccgtggccgg ggattcaaag ccgccgttcc ccaggtccct gggctgggcc ctgacaggga      840
gccgcccccc tccccatggt aaccaggaag cccgtttcat gttcagttgc ttttgtagag      900
gaagcaaggg ctgggatggg gacagctgtc aatcacaagc ccttaaataa agcagccagc      960
gcacaaaaaa aaaaaaaaaa aa                                              982

<210> SEQ ID NO 50
<211> LENGTH: 1767
<212> TYPE: DNA
<213> ORGANISM: Homo sapiens

<400> SEQUENCE: 50
gaaaggagca agccaggaag ccagacaaca acagcatcaa acaaggctg tttctgtgtg       60 tgaggaactt tgcctgggag ataaaattag acctagagct ttctgacagg gagtctgaag      120
cgtgggacat ggaccgttca ctgggatggc aagggaattc tgtccctgag acaggactg      180 aagctgggat caagcgtttc ctggaggaca ccacggatga tggagaactg agcaagttcg      240
tgaaggattt ctcaggaaat gcgagctgcc acccaccaga ggctaagacc tgggcatcca      300
ggccccaagt cccggagcca aggccccagg ccccggacct ctatgatgat gacctggagt      360
tcagaccccc ctcgcggccc cagtcctctg acaaccagca gtacttctgt gccccagccc      420
ctctcagccc atctgccagg ccccgcagcc catgggcaa gcttgatccc tatgattcct       480
ctgaggatga caaggagtat gtgggctttg caaccctccc caaccaagtc caccgaaagt      540
ccgtgaagaa aggctttgac tttacccctca tggtggcagg agagtctggc ctgggcaaat      600
ccacacttgt caatagcctc ttcctcactg atctgtaccg ggaccggaaa cttcttggtg      660
ctgaagagag gatcatgcaa actgtggaga tcactaagca tgcagtggac atagaagaga      720
agggtgtgag gctgcggctc accattgtgg acacaccagg ttttggggat gcagtcaaca      780
acacagagtg ctggaagcct gtggcagaat acattgatca gcagtttgag cagtatttcc      840
gagacgagag tggcctgaac cgaaagaaca tccaagacaa cagggtgcac tgctgcctgt      900
acttcatctc acccttcggc catgggctcc ggccattgga tgttgaattc atgaaggccc      960
tgcatcagcg ggtcaacatc gtgcctatcc tggctaaggc agacacactg acacctcccg     1020
aagtggacca caagaaacgc aaaatccggg aggagattga gcattttgga atcaagatct     1080
atcaattccc cagactgtgac tctgatgagg atgaggactt caaattgcag gaccaagccc     1140
taaaggaaag catcccattt gcagtaattg gcagcaacac tgtagtagag gccagagggc     1200
ggcgagttcg gggtcgactc taccctggg gcatcgtgga agtggaaaac ccagggcact     1260
gcgactttgt gaagctgagg acaatgctgg tacgtaccca catgcaggac ctgaaggatg     1320
```

```
tgacacggga gacacattat gagaactacc gggcacagtg catccagagc atgacccgcc    1380
tggtggtgaa ggaacggaat cgcaacaaac tgactcggga aagtggtacc gacttcccca    1440
tccctgctgt cccaccaggg acagatccag aaactgagaa gcttatccga gagaaagatg    1500
aggagctgcg gcggatgcag gagatgctac acaaaataca aaaacagatg aaggagaact    1560
attaactggc tttcagccct ggatatttaa atctcctcct cttcttcctg tccatgccgg    1620
cccctcccag caccagctct gctcaggccc cttcagctac tgccacttcg ccttacatcc    1680
ctgctgactg cccagagact cagaggaaat aaagtttaat aaatctgtag gtggctaaaa    1740
aaaaaaaaaa aaaaaaaaaa aaaaaaa                                       1767
```

<210> SEQ ID NO 51
<211> LENGTH: 339
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (325)..(325)
<223> OTHER INFORMATION: n is a, c, g, or t

<400> SEQUENCE: 51

```
naaatgttaa tagtaacttt tatttgaaag ttagggagat gaaaatacat ttccaaattc      60
ttccaaagat atagctaaat gacaaaataa aaacttcact atgggccagg cgcggtgact     120
cacgcctgta atcctagcac tttgggaggc cgaggcaggt ggatcacctg agagcaggag     180
attgagacca gcctggccaa cttggtgaaa accctatctc tactaaaaaa tacaaaaact     240
agccgngcat gatggcgtat gttttgtaaat ccccagctac ttngggacat taagggcaga    300
agggatccgc tttgaacctc agggnggcca gaggtttac                            339
```

<210> SEQ ID NO 52
<211> LENGTH: 453
<212> TYPE: DNA
<213> ORGANISM: Homo sapiens
<220> FEATURE:
<221> NAME/KEY: misc_feature
<222> LOCATION: (453)..(453)
<223> OTHER INFORMATION: n is a, c, g, or t

<400> SEQUENCE: 52

```
ggtgggggg ggggggtgttt aaaaaatccc tcaaatataa caatgaagca tgcttttcta      60
acacaaagag taccaaaatg aatgtgctac tttctgttaa agttttattt ccagagcttg     120
cccaagcaag aatctacttg ccctgtaaaa ttctgcttat acagaattaa aactccttta     180
ttatcccaca aatacattat atatttccat agctttcttt agcccataca cttcttctta     240
agtgttcaac tttcaaatct ctgataaaat gaaactcatc atgaagacca gtcaaaatgc     300
taaaggaaac cttccttaat ctactttgca attactgttc ctttcagtta ctccctacct     360
gcgcctgcca tgaattttttg ttttttgtgtt ggtctattct ggactagtgg gctctacaat    420
gagggatgcg tatctggaat accgagagct ttn                                  453
```

<210> SEQ ID NO 53
<211> LENGTH: 1051
<212> TYPE: DNA
<213> ORGANISM: Homo sapiens

<400> SEQUENCE: 53

```
ggaccgccgc ctggttaaag gcgcttattt cccaggcagc cgctgcagtc gccacacctt      60
tgcccctgct gcgatgaccc tgtcgccact tctgctgttc ctgccaccgc tgctgctgct     120
gctggacgtc cccacggcgg cggtgcaggc gtcccctctg caagcgttag acttctttgg     180
gaatgggcca ccagttaact acaagacagg caatctatac ctgcggggc cctgaagaa      240
gtccaatgca ccgcttgtca atgtgaccct ctactatgaa gcactgtgcg gtggctgccg     300
agccttcctg atccgggagc tcttcccaac atggctgttg gtcatggaga tcctcaatgt     360
cacgctggtg ccctacggaa acgcacagga acaaaatgtc agtggcaggt gggagttcaa     420
gtgccagcat ggagaagagg agtgcaaatt caacaaggtg gaggcctgcg tgttggatga     480
acttgacatg gagctagcct tcctgaccat tgtctgcatg gaagagtttg aggacatgga     540
gagaagtctg ccactatgcc tgcagctcta cgccccaggg ctgtcgccag acactatcat     600
ggagtgtgca atgggggacc gcggcatgca gctcatgcac gccaacgccc agcggacaga     660
tgctctccag ccaccacacg agtatgtgcc ctgggtcacc gtcaatggga aacccttgga     720
agatcagacc cagctcctta cccttgtctg ccagttgtac cagggcaaga agccggatgt     780
ctgcccttcc tcaaccagct ccctcaggag tgtttgcttc aagtgatggc cggtgagctg     840
cggagagctc atggaaggcg agtgggaacc cggctgcctg ccttttttc tgatccagac     900
cctcggcacc tgctacttac caactggaaa attttatgca tcccatgaag cccagataca     960
caaaattcca ccccatgatc aagaatcctg ctccactaag aatggtgcta aagtaaaact    1020
agtttaataa gcaaaaaaaa aaaaaaaaa a                                    1051
```

<210> SEQ ID NO 54
<211> LENGTH: 340
<212> TYPE: DNA
<213> ORGANISM: Homo sapiens
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:

```
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (265)..(265)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t

<400> SEQUENCE: 54
ggcacgagca tacccatttt ttgagctttc tttgagggcc aactttttnc tctaaaacca      60
gccagggcat gcttttccct caccagctct ganttcttcc aggctaggca actggaaaag     120
cctggncatta gaaactgctt tnttggctta cggcccagct gagctgacca aaatagccaa    180
gagaaagact gttttgcacag tgtgaaattc tccagggga ataccatag ncaaaaagcc     240
aaganagcca gnacccacgn atggncaggg aacccacagg gcaaaaaaag gccgagttac    300
ccccaaggnc cggggtttgt gggagatggg aggcctaggt                         340

<210> SEQ ID NO 55
<211> LENGTH: 1760
<212> TYPE: DNA
<213> ORGANISM: Homo sapiens

<400> SEQUENCE: 55
atttctttat aaaccacaac tctgggcccg caatggcagt ccactgcctt gctgcagtca     60
cagaatggaa atctgcagag gcctccgcag tcacctaatc actcctcc tcttcctgtt    120
ccattcagag acgatctgcc gaccctctgg gagaaaatcc agcaagatgc aagccttcag    180
aatctgggat gttaaccaga agaccttcta tctgaggaac aaccaactag ttgctggata    240
cttgcaagga ccaaatgtca atttagaaga aagatagat gtggtaccca ttgagcctca    300
tgctctgttc ttgggaatcc atggagggaa gatgtgcctg tcctgtgtca agtctggtga    360
tgagaccaga ctccagctgg aggcagttaa catcactgac ctgagcgaga acagaaagca    420
ggacaagcgc ttcgccttca tccgctcaga cagcggcccc accaccagtt tgagtctgc     480
cgcctgcccc ggttggttcc tctgcacagc gatggaagct gaccagcccg tcagcctcac    540
caatatgcct gacgaaggcg tcatggtcac caaattctac ttccaggagg acgagtagta    600
ctgcccaggc ctgcctgttc ccattcttgc atggcaagga ctgcagggac tgccagtccc    660
cctgccccag ggctcccggc tatggggggca ctgaggacca gccattgagg ggtggaccct    720
cagaaggcgt cacaagaacc tggtcacagg actctgcctc ctcttcaact gaccagcctc    780
catgctgcct ccagaatggt ctttctaatg tgtgaatcag agcacagcag ccctgcaca     840
aagcccttcc atgtcgcctc tgcattcagg atcaaacccc gaccacctgc ccaacctgct    900
ctcctcttgc cactgcctct tcctccctca ttccaccttc ccatgccctg gatccatcag    960
gccacttgat gacccccaac caagtggctc ccacaccctg ttttacaaaa aagaaaagac   1020
cagtccatga gggaggtttt taagggtttg tggaaaatga aaattaggat ttcatgattt   1080
ttttttttca gtccccgtga aggagagccc ttcatttgga gattatgttc tttcggggag   1140
aggctgagga cttaaaatat tcctgcattt gtgaaatgat ggtgaaagta agtggtagct   1200
tttcccttct ttttcttctt ttttgtgat gtcccaactt gtaaaaatta aaagttatgg    1260
tactatgtta gccccataat tttttttttc cttttaaaac acttccataa tctgactcc    1320
tctgtccagg cactgctgcc cagcctccaa gctccatctc cactccagat ttttttacagc   1380
```

```
tgcctgcagt actttacctc ctatcagaag tttctcagct cccaaggctc tgagcaaatg   1440
tggctcctgg gggttctttc ttcctctgct gaaggaataa attgctcctt gacattgtag   1500
agcttctggc acttggagac ttgtatgaaa gatggctgtg cctctgcctg tctccccac    1560 cgggctggga gctctgcaga gcaggaaaca tgactcgtat atgtctcagg tccctgcagg   1620
gccaagcacc tagcctcgct cttggcaggt actcagcgaa tgaatgctgt atatgttggg   1680
tgcaaagttc cctacttcct gtgacttcag ctctgtttta caataaaatc ttgaaaatgc   1740
ctaaaaaaaa aaaaaaaaaa                                               1760

<210> SEQ ID NO 56
<211> LENGTH: 584
<212> TYPE: DNA
<213> ORGANISM: Homo sapiens

<400> SEQUENCE: 56
cacctgcacc ccgcccgggc atagcaccat gcctgcttgt cgcctaggcc cgctagccgc     60
cgccctcctc ctcagcctgc tgctgttcgg cttcacccta gtctcaggca caggagcaga    120
gaagactggc gtgtgccccg agctccaggc tgaccagaac tgcacgcaag agtgcgtctc    180
ggacagcgaa tgcgccgaca acctcaagtg ctgcagcgcg ggctgtgcca ccttctgcct    240
tctctgccca aatgataagg agggttcctg cccccaggtg aacattaact ttccccagct    300
cggcctctgt cgggaccagt gccaggtgga cagccagtgt cctggccaga tgaaatgctg    360
ccgcaatggc tgtgggaagg tgtcctgtgt cactcccaat ttctgaggtc cagccaccac    420
caggctgagc agtgaggaga gaaagtttct gcctggccct gcatctggtt ccagcccacc    480
tgccctcccc tttttcggga ctctgtattc cctcttgggc tgaccacagc ttctcccttt    540
cccaaccaat aaagtaacca ctttcagcaa aaaaaaaaaa aaaa                      584

<210> SEQ ID NO 57
<211> LENGTH: 1330
<212> TYPE: DNA
<213> ORGANISM: Homo sapiens

<400> SEQUENCE: 57
gcagcccagc caagcactgt caggaatcct gtgaagcagc tccagctatg tgtgaagaag     60
aggacagcac tgccttggtg tgtgacaatg gctctgggct ctgtaaggcc ggctttgctg    120
gggacgatgc tcccagggct gttttcccat ccattgtggg acgtcccaga catcaggggg    180
tgatggtggg aatgggacaa aaagacagct acgtgggtga cgaagcacag agcaaaagag    240
gaatcctgac cctgaagtac ccgatagaac atggcatcat caccaactgg gacgacatgg    300
aaaagatctg gcaccactct ttctacaatg agcttcgtgt tgcccctgaa gagcatccca    360
ccctgctcac ggaggcaccc ctgaacccca aggccaaccg ggagaaaatg actcaaatta    420
tgtttgagac tttcaatgtc ccagccatgt atgtggctat ccaggcggtg ctgtctctct    480
atgcctctgg acgcacaact ggcatcgtgc tggactctgg agatggtgtc acccacaatg    540
tccccatcta tgagggctat gccttgcccc atgccatcat gcgtctggat ctggctggcc    600
gagatctcac tgactacctc atgaagatct gactgagcg tggctattcc ttcgttacta     660
ctgctgagcg tgagattgtc cgggacatca aggagaaact gtgttatgta gctctggact    720
ttgaaaatga gatggccact gccgcatcct catcctccct tgagaagagt tacgagttgc    780
ctgatgggca agtgatcacc atcggaaatg aacgtttccg ctgcccagag accctgttcc    840
```

| | |
|---|---:|
| agccatcctt catcgggatg gagtctgctg gcatccatga aaccacctac aacagcatca | 900 |
| tgaagtgtga tattgacatc aggaaggacc tctatgctaa caatgtccta tcaggggca | 960 |
| ccactatgta ccctggcatt gccgaccgaa tgcagaagga gatcacggcc ctagcaccca | 1020 |
| gcaccatgaa gatcaagatc attgcccctc cggagcgcaa atactctgtc tggatcggtg | 1080 |
| gctccatcct ggcctctctg tccaccttcc agcagatgtg gatcagcaaa caggaatacg | 1140 |
| atgaagccgg gccttccatt gtccaccgca aatgcttcta aaacactttc ctgctcctct | 1200 |
| ctgtctctag cacacaactg tgaatgtcct gtggaattat gccttcagtt cttttccaaa | 1260 |
| tcattcctag ccaaagctct gactcgttac ctatgtgttt tttaataaat ctgaaatagg | 1320 |
| ctactggtaa | 1330 |

<210> SEQ ID NO 58
<211> LENGTH: 2743
<212> TYPE: DNA
<213> ORGANISM: Homo sapiens

<400> SEQUENCE: 58

| | |
|---|---:|
| gcgggccgtt atccatttgt gttgttcgcc agctaggcct ggcctcgtcc cgcttcgctc | 60 |
| ggtcggtctc gcgcgccccc atagccttgc tagagggtta gcgttagcct taagtgtgcg | 120 |
| aatccgagga gcagcgacag actcgagacc acgctccttc ctcgggaagg aggcggcacc | 180 |
| tcgcgtttga ggcccgcctg cgtttgaggc ccgcctgcgc ttgcggcccg cctgcgcttg | 240 |
| aggcctgtct gcgtttgaga tctcattggg cgtgattgag gaatttgggg aggttttttgg | 300 |
| gcggtattga ggacgagggg gtccgttagt cagcatagaa tcctggagcg ggaatccctc | 360 |
| accgtctaaa tggcgtcggg ggcgggacct ccgggatctg gcttccgcgg gccgccgccg | 420 |
| gccctgaaac gtgagggata gctgagatga ggcagctact gggatggccc ccatgcgcat | 480 |
| ttacatgcag tccgactgcc gagctttcga ggcagcagga tttaccgtcc acattcctca | 540 |
| ctactaacca agcttttaga acagatctca caagaaccta gaggtcggta ttttttcgat | 600 |
| ttaaatttgc ctgttactga cgttaacgtc tttcgcctag tgagcagtag ccaacatgtc | 660 |
| agggtgggag tcatattaca aaaccgaggg cgatgaagaa gcagaggaag aacaagaaga | 720 |
| gaaccttgaa gcaagtggag actataaata ttcaggaaga gatagtttga tttttttggt | 780 |
| tgatgcctcc aaggctatgt ttgaatctca gagtgaagat gagttgacac cttttgacat | 840 |
| gagcatccag tgtatccaaa gtgtgtacat cagtaagatc ataagcagtg atcgagatct | 900 |
| cttggctgtg gtgttctatg gtaccgagaa agacaaaaat tcagtgaatt ttaaaaatat | 960 |
| ttacgtctta caggagctgg ataatccagg tgcaaaacga attctagagc ttgaccagtt | 1020 |
| taaggggcag cagggacaaa aacgtttcca agacatgatg ggccacggat ctgactactc | 1080 |
| actcagtgaa gtgctgtggg tctgtgccaa cctctttagt gatgtccaat tcaagatgag | 1140 |
| tcataagagg atcatgctgt tcaccaatga agacaacccc catggcaatg acagtgccaa | 1200 |
| agccagccgg gccaggacca agccggtga tctccgagat acaggcatct tccttgactt | 1260 |
| gatgcacctg aagaaacctg ggggctttga catatccttg ttctacagag atatcatcag | 1320 |
| catagcagag gatgaggacc tcagggttca ctttgaggaa tccagcaagc tagaagacct | 1380 |
| gttgcggaag gttcgcgcca aggagaccag gaagcgagca ctcagcaggt taaagctgaa | 1440 |
| gctcaacaaa gatatagtga tctctgtggg catttataat ctggtccaga aggctctcaa | 1500 |
| gcctcctcca ataaagctct atcgggaaac aaatgaacca gtgaaaacca agacccggac | 1560 |
| cttaatacag agtacaggcg gtttgcttct gcctagcgat accaagaggt ctcagatcta | 1620 |

```
tgggagtcgt cagattatac tggagaaaga ggaaacagaa gagctaaaac ggtttgatga    1680
tccaggtttg atgctcatgg gtttcaagcc gttggtactg ctgaagaaac accattacct    1740
gaggccctcc ctgttcgtgt acccagagga gtcgctggtg attgggagct caaccctgtt    1800
cagtgctctg ctcatcaagt gtctggagaa ggaggttgca gcattgtgca gatacacacc    1860
ccgcaggaac atccctcctt attttgtggc tttggtgcca caggaagaag agttggatga    1920
ccagaaaatt caggtgactc ctccaggctt ccagctggtc ttttttaccct tgctgatga    1980 taaaaggaag atgccctttta ctgaaaaaat catggcaact ccagagcagg tgggcaagat    2040
gaaggctatc gttgagaagc ttcgcttcac atacagaagt gacagctttg agaacccgt    2100 gctgcagcag cacttcagga acctggaggc cttggccttg gatttgatgg agccggaaca    2160
agcagtggac ctgacattgc ccaaggttga agcaatgaat aaaagactgg gctccttggt    2220
ggatgagttt aaggagcttg tttacccacc agattacaat cctgaaggga agttaccaa    2280 gagaaaacac gataatgaag gttctggaag caaaaggccc aaggtggagt attcagaaga    2340
ggagctgaag acccacatca gcaagggtac gctgggcaag ttcactgtgc ccatgctgaa    2400
agaggcctgc cgggcttacg ggctgaagag tggtctgaag aagcaggagc tgctggaagc    2460
cctcaccaag cacttccagg actgaccaga ggccgcgcgt ccagctgccc ttccgcagtg    2520
tggccaggct gcctggcctt gtcctcagcc agttaaaatg tgtttctcct gagctaggaa    2580
gagtctaccc gacataagtc gagggacttt atgtttttga ggctttctgt tgccatggtg    2640
atggtgtagc cctcccactt tgctgttctt tactttactg cctgaataaa gagccctaag    2700
tttgtactaa aaaaaaaaaa aaaaaaaaaa aaaaaaaaaa aaa                      2743

<210> SEQ ID NO 59
<211> LENGTH: 1826
<212> TYPE: DNA
<213> ORGANISM: Homo sapiens

<400> SEQUENCE: 59
agtatgtgtg gttggggaat tcatgtggag gtcagagtgg aagcaggtgt gagagggtcc      60
agcagaagga acatggctgc caaagtgtt tgagtccatt ggcaagtttg cctggccctt     120
agctgttgca ggaggcgtgg tgaactctgc cttatataat gtggatgctg ggcacagagc     180
tgtcatcttt gaccgattcc gtggagtgca ggacattgtg gtaggggaag ggactcattt     240
tctcatcccg tgggtacaga aaccaattat ctttgactgc cgttctcgac cacgtaatgt     300
gccagtcatc actggtagca agatttaca gaatgtcaac atcacactgc gcatcctctt     360
ccggcctgtc gccagccagc ttcctcgcat cttcaccagc atcggagagg actatgatga     420
gcgtgtgctg ccgtccatca caactgagat cctcaagtca gtggtggctc gctttgatgc     480
tggagaacta atcacccaga gagctggt ctccaggcag gtgagcgacg accttacaga     540
gcgagccgcc acctttgggc tcatcctgga tgacgtgtcc ttgacacatc tgaccttcgg     600
gaaggagttc acagaagcgg tggaagccaa acaggtggct cagcaggaag cagagagggc     660
cagatttgtg gtggaaaagg ctgagcaaca gaaaaaggcg gccatcatct ctgctgaggg     720
cgactccaag gcagctgagc tgattgccaa ctcactggcc actgcagggg atggcctgat     780
cgagctgcgc aagctggaag ctgcagagga catcgcgtac cagctctcac gctctcggaa     840
catcacctac ctgccagcgg ggcagtccgt gctcctccag ctgccccagt gagggcccac     900
cctgcctgca cctccgcggg ctgactgggc cacagccccg atgattctta acacagcctt     960
```

```
ccttctgctc ccaccccaga aatcactgtg aaatttcatg attggcttaa agtgaaggaa       1020
ataaaggtaa aatcacttca gatctctaat tagtctatca aatgaaactc tttcattctt       1080
ctcacatcca tctactttt tatccacctc cctaccaaaa attgccaagt gcctatgcaa        1140
accagcttta ggtcccaatt cggggcctgc tggagttccg gcctgggcac cagcatttgg       1200
cagcacgcag gcggggcagt atgtgatgga ctggggagca caggtgtctg cctagatcca      1260
cgtgtggcct ccgtcctgtc actgatgaa ggtttgcgga tgaggggcatg tgcggctgaa      1320 ctgagaaggc aggcctccgt cttcccagcg gttcctgtgc agatgctgct gaagagaggt     1380
gccggggagg ggcagagagg aagtggtctg tctgttacca taagtctgat tctctttaac     1440
tgtgtgacca gcggaaacag gtgtgtgtga actgggcaca gattgaagaa tctgcccctg     1500
ttgaggtggg tgggcctgac tgttgcccc cagggtccta aaacttggat ggacttgtat      1560
agtgagagag gaggcctgga ccgagatgtg agtcctgttg aagacttcct ctctaccccc     1620
caccttggtc cctctcagat acccagtgga attccaactt gaaggattgc atcctgctgg    1680
ggctgaacat gcctgccaaa gacgtgtccg acctacgttc ctggcccct cgttcagaga     1740 ctgcccttct cacgggctct atgcctgcac tgggaaggaa acaaatgtgt ataaactgct    1800
gtcaataaat gacacccaga ccttcc                                          1826

<210> SEQ ID NO 60
<211> LENGTH: 4322
<212> TYPE: DNA
<213> ORGANISM: Homo sapiens

<400> SEQUENCE: 60
cccccagagg cgccggagcc cggaatcccg ctcggagcca gccagccgtc ccgagctacc         60
agcaggtttc attgaaaaca gatcctgcaa aagttccagg tgcccacact ggaaacttgg       120
agatcctgct tcccagacca cagctgtggg gaacttgggg tggagcagag aagtttctgt       180
attcagctgc ccaggcagag gagaatgggg tctccacagc ctgaagaatg aagacacgac       240
agaataaaga ctcgatgtca atgaggagtg acgggaagaa agaggcccct gggccccggg       300
aagaactgag atcgaggggc cgggcctccc ctggaggggt cagcacgtcc agcagtgatg       360
gcaaagctga gaagtccagg cagacagcca agaaggcccg agtagaggaa gcctccaccc       420
caaaggtcaa caagcagggt cggagtgagg agatctcaga gagtgaaagt gaggagacca       480
atgcaccaaa aaagaccaaa actgaggaac tccctcggcc acagtctccc tccgatctgg       540
atagcttgga cgggcggagc cttaatgatg atggcagcag cgaccctagg gatatcgacc       600
aggacaaccg aagcacgtcc cccagtatct acagccctgg aagtgtggag aatgactctg       660
actcatcttc tggcctgtcc cagggcccag cccgccccta ccaccacct ccactctttc        720 ctccttcccc tcaaccgcca gacagcaccc ctcgacagcc agaggctagc tttgaacccc        780
atccttctgt gacaccccact ggatatcatg ctcccatgga gcccccacac ctcgaatgt        840 tccaggctcc tcctggggcc cctcccccctc acccacagct ctatcccggg ggcactggtg      900
gagttttgtc tggacccccca atgggtccca aggggggagg ggctgcctca tcagtggggg      960
gccctaatgg gggtaagcag caccccccac ccactactcc catttcagta tcaagctctg     1020
gggctagtgg tgctcccccca acaaagccgc ctaccactcc agtgggtggt gggaacctac    1080
cttctgctcc accaccagcc aacttccccc atgtgacacc gaacctgcct ccccaccctg    1140
ccctgagacc cctcaacaat gcatcagcct ctccccctgg cctggggggcc caaccactac    1200 ctggtcatct gccctctccc cacgccatgg gacagggtat cggtggactt cctcctggcc    1260
```

```
cagagaaggg cccaactctg gctccttcac cccactctct gcctcctgct tcctcttctg   1320
ctccagcgcc ccccatgagg tttccttatt catcctctag tagtagctct gcagcagcct   1380
cctcttccag ttcttcctcc tcttcctctg cctcccccct tccccagcttcc caggcattgc  1440 ccagctaccc ccactctttc cctcccccaa caagcctctc tgtctccaat cagcccccca   1500
agtatactca gccttctctc ccatcccagg ctgtgtggag ccagggtccc ccaccacctc   1560
ctccctatgg ccgcctctta gccaacagca atgcccatcc aggccccttc cctccctcta   1620
ctggggccca gtccaccgcc cacccaccag tctcaacaca tcaccatcac caccagcaac   1680
agcaacagca gcagcagcag cagcagcagc agcagcatca cggaaactct gggccccctc   1740
ctcctggagc atttccccac ccactggagg gcggtagctc ccaccacgca cacccttacg   1800
ccatgtctcc ctccctgggg tctctgaggc cctacccacc agggccagca cacctgcccc   1860
cacctcacag ccaggtgtcc tacagccaag caggccccaa tggccctcca gtctcttcct   1920
cttccaactc ttcctcttcc acttctcaag gtcctaccc atgttcacac ccctccctt    1980 cccagggccc tcaaggggcg ccctacccett tcccaccggt gcctacggtc accacctctt   2040
cggctaccct ttccacggtc attgccaccg tggcttcctc gccagcaggc tacaaaacgg   2100
cctccccacc tgggccccca ccgtacgaaa agagagcccc gtccccgggg gcctacaaga   2160
cagccacccc acccggatac aaacccgggt cgcctccctc cttccgaacg gggacccac    2220 cgggctatcg aggaacctcg ccacctgcag gcccagggac cttcaagccg gctcgccca    2280 ccgtgggacc tgggccccctg ccacctgcgg ggccctcagg cctgccatcg ctgccaccac  2340
cacctgcggc ccctgcctca gggccgcccc tgagcgccac gcagatcaaa caggagccgg   2400
ctgaggagta tgagaccccc gagagccccgg tgccccagc ccgcagcccc tcgccccctc    2460
ccaaggtggt agatgtaccc agccatgcca gtcagtctgc caggttcaac aaacacctgg   2520
atcgcggctt caactcgtgc gcgcgcagcg acctgtactt cgtgccactg gagggctcca   2580
agctggccaa gaagcgggcc gacctggtgg agaaggtgcg gcgcgaggcc gagcagcgcg   2640
cgcgcgaaga aaaggagcgc gagcgcgagc gggaacgcga gaaagagcgc gagcgcgaga   2700
aggagcgcga gcttgaacgc agcgtgaagt tggctcagga gggccgtgct ccggtggaat   2760
gcccatctct gggcccagtg ccccatcgcc ctccatttga accgggcagt gcggtggcta   2820
cagtgccccc ctacctgggt cctgacactc cagccttgcg cactctcagt gaatatgccc   2880
ggcctcatgt catgtctcct ggcaatcgca accatccatt ctacgtgccc ctgggggcag   2940
tggacccggg gctcctgggt tacaatgtcc cggccctgta cagcagtgat ccagctgccc   3000
gggagaggga acgggaagcc cgtgaacgag acctccgtga ccgcctcaag cctggctttg   3060
aggtgaagcc tagtgagctg gaaccctac atggggtccc tgggccgggc ttggatccct   3120
ttccccgaca tgggggcctg gctctgcagc ctggcccacc tggcctgcac cctttcccct   3180
ttcatccgag cctggggccc ctggagcgag aacgtctagc gctggcagct gggccagccc   3240
tgcggcctga catgtcctat gctgagcggc tggcagctga gaggcagcac gcagaaaggg   3300
tggcggccct gggcaatgac ccactggccc ggctgcagat gctcaatgtg actccccatc   3360
accaccagca ctcccacatc cactcgcacc tgcacctgca ccagcaagat gctatccatg   3420
cagcctctgc ctcggtgcac cctctcattg accccctggc ctcagggtct caccttaccc   3480 ggatcccta cccagctgga actctcccta ccccctgct tcctcaccct ctgcacgaga    3540
acgaagttct tcgtcaccag ctctttgctg ccccttaccg ggacctgccg gcctccctt   3600
```

-continued

```
ctgccccgat gtcagcagct catcagctgc aggccatgca cgcacagtca gctgagctgc    3660
agcgcttggc gctggaacag cagcagtggc tgcatgccca tcacccgctg cacagtgtgc    3720
cgctgcctgc ccaggaggac tactacagtc acctgaagaa ggaaagcgac aagccactgt    3780
agaacctgcg atcaagagag caccatggct cctacattgg accttggagc accccacccc    3840 tcccccacc gtgccttgg cctgccaccc agagccaaga gggtgctgct cagttgcagg    3900
gcctccgcag ctggacagag agtgggggag ggagggacac acagaaggcc aaggcccgat    3960
gtggtgtgca gaggtgggga ggtggcgagg atggggacag aaagcgcaca gaatcttgga    4020
ccaggtctct cttccttgtc cccctgctt ttctcctccc ccatgcccaa ccctgtggc    4080 cgccgcccct cccctgcccc gttggtgtga ttatttcatc tgttagatgt ggctgttttg    4140
cgtagcatcg tgtgccaccc ctgccctcc ccgatccctg tgcgcgcc cctctgcaa    4200 tgtatgcccc ttgccccttc cccacactaa taatttatat ataaatat ctatatgacg    4260 ctcttaaaaa aacatcccaa ccaaaaccaa ccaaacaaaa acatcctcac aactccccag    4320
ga                                                                  4322
```

<210> SEQ ID NO 61
<211> LENGTH: 3088
<212> TYPE: DNA
<213> ORGANISM: Homo sapiens

<400> SEQUENCE: 61

```
acaaaaaagc ttttacgagg tatcagcact tttctttcat taggggaag gcgtgaggaa      60 agtaccaaac agcagcggag ttttaaactt taaatagaca ggtctgagtg cctgaacttg     120 cctttcatt ttacttcatc ctccaaggag ttcaatcact tggcgtgact tcactacttt     180
taagcaaaag agtggtgccc aggcaacatg ggtgactgga gcgccttagg caaactcctt     240
gacaaggttc aagcctactc aactgctgga gggaaggtgt ggctgtcagt acttttcatt     300
ttccgaatcc tgctgctggg gacagcggtt gagtcagcct ggggagatga gcagtctgcc     360
tttcgttgta acactcagca acctggttgt gaaaatgtct gctatgacaa gtctttccca     420
atctctcatg tgcgcttctg ggtcctgcag atcatatttg tgtctgtacc cacactcttg     480
tacctggctc atgtgttcta tgtgatgcga aggaagaga aactgaacaa gaaagaggaa     540
gaactcaagg ttgcccaaac tgatggtgtc aatgtggaca tgcacttgaa gcagattgag     600
ataaagaagt tcaagtacgg tattgaagag catggtaagg tgaaaatgcg agggggggttg     660 ctgcgaacct acatcatcag tatcctcttc aagtctatct ttgaggtggc cttcttgctg     720
atccagtggt acatctatgg attcagcttg agtgctgttt acacttgcaa aagagatccc     780
tgcccacatc aggtggactg ttttcctctct cgccccacgg agaaaaccat cttcatcatc     840
ttcatgctgg tggtgtcctt ggtgtccctg gccttgaata tcattgaact cttctatgtt     900
ttcttcaagg gcgttaagga tcgggttaag ggaaagagcg acccttacca tgcgaccagt     960
ggtgcgctga gccctgccaa agactgtggg tctcaaaaat atgcttattt caatggctgc    1020
tcctcaccaa ccgctcccct ctcgcctatg tctcctcctg ggtacaagct ggttactggc    1080
gacagaaaca attcttcttg ccgcaattac aacaagcaag caagtgagca aaactgggct    1140
aattacagtg cagaacaaaa tcgaatgggg caggcgggaa gcaccatctc taactcccat    1200
gcacagcctt tgatttccc cgatgataac cagaattcta aaaaactagc tgctggacat    1260
gaattacagc cactagccat tgtggaccag cgacttcaa gcagagccag cagtcgtgcc    1320
agcagcagac ctcggcctga tgacctggag atctagatac aggcttgaaa gcatcaagat    1380
```

| | |
|---|---|
| tccactcaat tgtggagaag aaaaaaggtg ctgtagaaag tgcaccaggt gttaattttg | 1440 |
| atccggtgga ggtggtactc aacagcctta ttcatgaggc ttagaaaaca caaagacatt | 1500 |
| agaataccta ggttcactgg gggtgtatgg ggtagatggg tggagaggga ggggataaga | 1560 |
| gaggtgcatg ttggtattta aagtagtgga ttcaaagaac ttagattata aataagagtt | 1620 |
| ccattaggtg atacatagat aagggctttt tctccccgca acaccccta agaatggttc | 1680 |
| tgtgtatgtg aatgagcggg tggtaattgt ggctaaatat ttttgtttta ccaagaaact | 1740 |
| gaaataattc tggccaggaa taaatacttc ctgaacatct taggtctttt caacaagaaa | 1800 |
| aagacagagg attgtcctta agtccctgct aaaacattcc attgttaaaa tttgcacttt | 1860 |
| gaaggtaagc tttctaggcc tgaccctcca ggtgtcaatg gacttgtgct actatatttt | 1920 |
| tttattcttg gtatcagttt aaaattcaga caaggcccac agaataagat tttccatgca | 1980 |
| tttgcaaata cgtatattct ttttccatcc acttgcacaa tatcattacc atcactttt | 2040 |
| catcattcct cagctactac tcacattcat ttaatggttt ctgtaaacat ttttaagaca | 2100 |
| gttgggatgt cacttaacat ttttttttt tgagctaaag tcagggaatc aagccatgct | 2160 |
| taatatttaa caatcactta tatgtgtgtc gaagagtttg ttttgtttgt catgtattgg | 2220 |
| tacaagcaga tacagtataa actcacaaac acagatttga aaataatgca catatggtgt | 2280 |
| tcaaatttga acctttctca tggattttg tggtgtgggc caatatggtg tttacattat | 2340 |
| ataattcctg ctgtggcaag taaagcacac ttttttttc tcctaaaatg ttttccctg | 2400 |
| tgtatcctat tatggatact ggttttgtta attatgattc tttattttct ctccttttt | 2460 |
| taggatatag cagtaatgct attactgaaa tgaatttcct ttttctgaaa tgtaatcatt | 2520 |
| gatgcttgaa tgatagaatt ttagtactgt aaacaggctt tagtcattaa tgtgagagac | 2580 |
| ttagaaaaaa tgcttagagt ggactattaa atgtgcctaa atgaatttg cagtaactgg | 2640 |
| tattcttggg ttttcctact taatacacag taattcagaa cttgtattct attatgagtt | 2700 |
| tagcagtctt ttggagtgac cagcaacttt gatgtttgca ctaagatttt atttggaatg | 2760 |
| caagagaggt tgaaagagga ttcagtagta cacatacaac taatttattt gaactatatg | 2820 |
| ttgaagacat ctaccagttt ctccaaatgc cttttttaaa actcatcaca gaagattggt | 2880 |
| gaaaatgctg agtatgacac ttttcttctt gcatgcatgt cagctacata aacagttttg | 2940 |
| tacaatgaaa attactaatt tgtttgacat tccatgttaa actacggtca tgttcagctt | 3000 |
| cattgcatgt aatgtagacc tagtccatca gatcatgtgt tctggagagt gttctttatt | 3060 |
| caataaagtt ttaatttagt ataaacat | 3088 |

<210> SEQ ID NO 62
<211> LENGTH: 2828
<212> TYPE: DNA
<213> ORGANISM: Homo sapiens

<400> SEQUENCE: 62

| | |
|---|---|
| gcgctacggc ggacccggct gggcagttcc ttccccagaa ggagagattc ctctgccatg | 60 |
| gagtcctacg atgtgatcgc caaccagcct gtcgtgatcg acaacggatc cggtgtgatt | 120 |
| aaagctggtt ttgctggtga tcagatcccc aaatactgct ttccaaacta tgtgggccga | 180 |
| cccaagcacg ttcgtgtcat ggcaggagcc cttgaaggcg acatcttcat ggccccaaa | 240 |
| gctgaggagc accagggct gctttcaatc cgctatccca tggagcatgg catcgtcaag | 300 |
| gattggaacg acatggaacg catttggcaa tatgtctatt ctaaggacca gctgcagact | 360 |

-continued

```
ttctcagagg agcatcctgt gctcctgact gaggcgcctt taaacccacg aaaaaaccgg      420
gaacgagctg ccgaagtttt cttcgagacc ttcaatgtgc ccgctctttt catctccatg      480
caagctgtac tcagccttta cgctacaggc aggaccacag gggtggtgct ggattctggg      540
gatggagtca cccatgctgt gcccatctat gagggctttg ccatgcccca ctccatcatg      600
cgcatcgaca tcgcgggccg ggacgtctct cgcttcctgc gcctctacct gcgtaaggag      660
ggctacgact tccactcatc ctctgagttt gagattgtca aggccataaa agaaagagcc      720
tgttacctat ccataaaccc ccaaaaggat gagacgctag agacagagaa agctcagtac      780
tacctgcctg atggcagcac cattgagatt ggtccttccc gattccgggc ccctgagttg      840
ctcttcaggc cagatttgat tggagaggag agtgaaggca tccacgaggt cctggtgttc      900
gccattcaga agtcagacat ggacctgcgg cgcacgcttt tctctaacat tgtcctctca      960
ggaggctcta ccctgttcaa aggttttggt gacaggctcc tgagtgaagt gaagaaacta     1020
gctccaaaag atgtgaagat caggatatct gcacctcagg agagactgta ttccacgtgg     1080
attgggggct ccatccttgc ctccctggac acctttaaga gatgtgggt ctccaaaaag      1140 gaatatgagg aagacggtgc ccgatccatc cacagaaaaa ccttctaatg tcgggacatc     1200
atcttcacct ctctctgaag ttaactccac tttaaaactc gctttcttga gtcggagtgt     1260
ttgcgaggaa ctgcctgtgt gtgagtgcgt gtgtggatat gagtgtgtgc gcacatgcga     1320
gtgccgtgtg gccctgggac cctgggccca gaaaggacga tgaactaccc gcagtggtga     1380
tgcctgaggc ctggggttga ccactaactg gctcctgaca gggaagagcg ctggcagagg     1440
ctgtgctccc tcctcaggtg gcctctggct ggctgtgggg gactccgttt actaccacag     1500
ggagacagag ggaggtaagc catccccgg gagaccttgc tgctgaccat cctaggctgg      1560
gctggcccac cctcacccc acccccaggg tgccctgagg ccccaggcag ctgctgcctc      1620
cactatcgat gcctcctgac tgcacactga ggactgggac tggggttgag ttctgtctgg     1680
ttttgttgcc attttggttt gggaggctgg aaaagcaccc caagaagcta ttacagagac     1740
tggagtcagg agagagcagg aggccctcat gttcaccagg gaacaggacc acaccggcca     1800
ctgaaggagg gcaggagcag tcctccctct gaatggctgc agagttaatg ttcccagccc     1860
agtccccttt cggggggcctt gggagagttt aaggcacctg ctggttccag gacctcgctt     1920
tccatctgtt cttgttgcaa tgccatcttc aaaccgtttt atttattgaa gtgtttgttc     1980
agttaggggc tggagagagg gagcttgctg cctcctgcct tgctacacta atgtttacag     2040
cacctaagct tagcctccag ggccccacct ctcccagctg atggtgagct gacagtgtcc     2100
acaggttcca ggaccatttg agattggaag ctacactcaa agacactccc accaggctct     2160
ttctcccttt tcctcttctc actgccctgg aatcaacagg ctggttgctg gttagatttt     2220
ctgaaacagg aggtaaaatt tttctttggc agaggcccct aagcaaggga gggtgttgg      2280 agagccagtg cccttaagac tggagaaagc tgcaatttac caagttgcct tttgccactg     2340
tagctgacca ggggactagg ttgtagaggt gggaaggccc ctctgggctg atcttgtgcc     2400
attcttgacc ttggacctgc ttggttaagg agggagtggg ccagaccaga gtgccaggag     2460
ctaatggagc caggcctgac acctaggagt ggtccaaagc cttcagccta gatggtgcaa     2520
agctggggcc agcctgtctt caccggcacc ctcacctgtg acaccaagac ccaccccaat     2580
ccagacttca cacagtattc tccccacgc cgtctatgac caaaggcccc tgccaggtgt      2640
gggtccacag cagcaggtat gtgtgaaagc aacgtagcgc cccgcggact gcagtgcgct     2700
taaccaactc acctcccttc tcttagccca agcctgtccc tcgcacagcc tcgcacaaac     2760
```

```
cacattgcct ggtggggccc agtgtactga aataaagtcg ttccgataga cacgtcaaaa    2820
aaaaaaaa                                                             2828

<210> SEQ ID NO 63
<211> LENGTH: 415
<212> TYPE: DNA
<213> ORGANISM: Homo sapiens

<400> SEQUENCE: 63
ttttttttat tgctattaag attttctttt taatatgcca tgagatatct tgattgtata      60
ttttccaaag tactttccag ccacatctcc caacccatcc aaaagacttt gccagtcttt     120
ccaatgcaat aaaagatgct ggattatagt tttgtctacc atttcttttt gaaagcaata     180
ttatactaat gactttaatg gtaatacact cttatctaat aaagaaacac atttacaaat     240
atcagaaacc cagttttgga acaatttgca taaattttga actgaatcag cattttgtgg     300
gttttttaaa aggcagcagt ttgactcacg acttgctgat aaacacgttt ctgctgaggg     360
aaggggaaaa gacagggaga gtgaatgctg catttctcca ttggccccaa aagtg         415

<210> SEQ ID NO 64
<211> LENGTH: 2455
<212> TYPE: DNA
<213> ORGANISM: Homo sapiens

<400> SEQUENCE: 64
gaattcgggc gggcttcttc gctgccgacg tacgacgagt ggccgggctc ttgcgtctgg      60
taacgcgctg tctctaacgc cagcgccgtc tcgcgcgcac tgcgcacaga ccacccgcag     120
acgcccggca gtccgcaggc ccaaacgcgc acgcgacccc gctctccgca ccgtacccgg     180
ccgcctcggc atggcgcccc gcagcgcccg gcgaccctg ctgctgctac tgcctgttgc      240
tgctgctcgg cctcatgcat tgtcgtcagc agccatgttt atggtgaaaa atggcaacgg     300
gaccgcgtgc ataatggcca acttctctgc tgccttctca gtgaactacg acaccaagag     360
tggccccaag aacatgacct ttgacctgcc atcagatgcc acagtggtgc tcaaccgcag     420
ctcctgtgga aaagagaaca cttctgaccc cagtctcgtg attgcttttg aagaggaca      480 tacactcact ctcaatttca cgagaaatgc aacacgttac agcgttcagc tcatgagttt     540
tgtttataac ttgtcagaca cacaccttttt ccccaatgcg agctccaaag aaatcaagac     600
tgtggaatct ataactgaca tcagggcaga tatagataaa aaatacagat gtgttagtgg     660
cacccaggtc cacatgaaca acgtgaccgt aacgctccat gatgccacca tccaggcgta     720
cctttccaac agcagcttca gcaggggaga gacacgctgt gaacaagaca ggccttcccc     780
aaccacagcg cccctgcgc cacccagccc ctcgccctca ccgtgccca agagcccctc      840 tgtggacaag tacaacgtga gcggcaccaa cgggacctgc tgctggcca gcatgggct      900 gcagctgaac ctcacctatg agaggaagga caacacgacg gtgacaaggc ttctcaacat     960
caaccccaac aagacctcgg ccagcgggag ctgcggcgcc cacctggtga ctctggagct    1020
gcacagcgag ggcaccaccg tcctgctctt ccagttcggg atgaatgcaa gttctagccg    1080 gttttttccta caaggaatcc agttgaatac aattcttcct gacgccagag accctgcctt    1140
taaagctgcc aacggctccc tgcgagcgct gcaggccaca gtcggcaatt cctacaagtg    1200
caacgcggag gagcacgtcc gtgtcacgaa ggcgttttca gtcaatatat tcaaagtgtg    1260
ggtccaggct ttcaaggtgg aaggtggcca gtttggctct gtggaggagt gtctgctgga    1320
```

-continued

| | | |
|---|---|---|
| cgagaacagc acgctgatcc ccatcgctgt gggtggtgcc ctggcggggc tggtcctcat | 1380 |
| cgtcctcatc gcctacctcg tcggcaggaa gaggagtcac gcaggctacc agactatcta | 1440 |
| gcctggtgca cgcaggcaca gcagctgcag gggcctctgt tcctttctct gggcttaggg | 1500 |
| tcctgtcgaa ggggaggcac actttctgca aacgtttctc aaatctgctt catccaatgt | 1560 |
| gaagttcatc ttgcagcatt tactatgcac aacagagtaa ctatcgaaat gacggtgtta | 1620 |
| attttgctaa ctgggttaaa tattttgcta actggttaaa cattaatatt taccaaagta | 1680 |
| ggattttgag ggtgggggtg ctctctctga ggggtgggg gtgccgctgt ctctgagggg | 1740 |
| tgggggtgcc gctgtctgag gggtgggggt gccgctctct ctgaggggt ggggtgccg | 1800 |
| ctttctctga ggggtgggg gtgccgctct ctctgagggg gtggggtgc tgctctctcc | 1860 |
| gaggggtgga atgccgctgt ctctgagggg tgggggtgcc gctctaaatt ggctccatat | 1920 |
| cattgagttt agggttctgg tgtttggttt cttcattctt tactgcactc agatttaagc | 1980 |
| cttacaaagg gaaacctctg gccgtcacac gtaggacgca tgaaggtcac tcgtgtgagg | 2040 |
| ctgacatgct cacacattac aacagtagag agggaaaatc taagacaga ggaactccag | 2100 |
| agatgagtgt ctggagcggc ttcagttcag ctttaaaggc caggacgcgc gacacgtggc | 2160 |
| tggcggcctc gttccagtgg cggcacgtcc ttggcgtctc taatgtctgc agctcaaggg | 2220 |
| ctggcacttt tttaaatata aaaatggtgt tatttttatt ttttttttgta aagtgatttt | 2280 |
| tggtcttctg ttgacattcg ggtgatcctg ttctgcgctg tgtacaatgt gagatcggtg | 2340 |
| cgttctcctg atgttttgcc gtggcttggg gattgtacac gggaccagct cacgtaatgc | 2400 |
| attgcctgta acaatgtaat aaaaagcctc tttctttcaa aaaaccccg aattc | 2455 |

<210> SEQ ID NO 65
<211> LENGTH: 3583
<212> TYPE: DNA
<213> ORGANISM: Homo sapiens

<400> SEQUENCE: 65

| | | |
|---|---|---|
| cgcggacccg gccggcccag gcccgcgccc gccgcggccc tgagaggccc cggcaggtcc | 60 |
| cggcccggcg gcggcagcca tggccggggg gccgggcccg ggggagcccg cagccccgg | 120 |
| cgcccagcac ttcttgtacg aggtgccgcc ctgggtcatg tgccgcttct acaaagtgat | 180 |
| ggacgccctg gagcccgccg actggtgcca gttcgccgcc ctgatcgtgc gcgaccagac | 240 |
| cgagctgcgg ctgtgcgagc gctccgggca gcgcacggcc agcgtcctgt ggccctggat | 300 |
| caaccgcaac gcccgtgtgg ccgacctcgt gcacatcctc acgcacctgc agctgctccg | 360 |
| tgcgcgggac atcatcacag cctggcaccc tcccgccccg cttccgtccc caggcaccac | 420 |
| tgccccgagg cccagcagca tccctgcacc cgccgaggcc gaggcctgga gccccggaa | 480 |
| gttgccatcc tcagcctcca ccttcctctc cccagctttt ccaggctccc agacccattc | 540 |
| agggcctgag ctcggcctgg ttccaagccc tgcttccctg tggcctccac cgccatctcc | 600 |
| agcccttct tctaccaagc caggcccaga gagctcagtg tccctcctgc agggagcccg | 660 |
| cccctctccg ttttgctggc ccctctgtga gatttcccgg ggcacccaca acttctcgga | 720 |
| ggagctcaag atcggggagg gtggctttgg gtgcgtgtac cggcggtga tgaggaacac | 780 |
| ggtgtatgct gtgaagagc tgaaggaaa cgctgacctg gagtgactg cagtgaagca | 840 |
| gagcttcctg accgaggtgg agcagctgtc caggtttcgt cacccaaaca ttgtggactt | 900 |
| tgctggctac tgtgctcaga acggcttcta ctgcctggtg tacggcttcc tgcccaacgg | 960 |
| ctccctggag gaccgtctcc actgccagac ccaggcctgc ccacctctct cctggcctca | 1020 |

```
gcgactggac atccttctgg gtacagcccg ggcaattcag tttctacatc aggacagccc    1080
cagcctcatc catggagaca tcaagagttc aacgtcctt  ctggatgaga ggctgacacc    1140
caagctggga ctttggcc   tggcccggtt cagccgcttt gccggtcca  gccccagcca    1200
gagcagcatg gtggcccgga cacagacagt gcggggcacc ctggcctacc tgcccgagga    1260
gtacatcaag acgggaaggc tggctgtgga cacggacacc ttcagctttg ggtggtagt    1320
gctagagacc ttggctggtc agagggctgt gaagacgcac ggtgccagga ccaagtatct    1380
gaaagacctg gtggaagagg aggctgagga ggctggagtg gctttgagaa gcacccagag    1440
cacactgcaa gcaggtctgg ctgcagatgc ctgggctgct cccatcgcca tgcagatcta    1500
caagaagcac ctggaccca  ggcccgggcc ctgcccacct gagctgggcc tgggcctggg    1560
ccagctggcc tgctgctgcc tgcaccgccg ggccaaaagg aggcctccta tgacccaggt    1620
gtacgagagg ctagagaagc tgcaggcagt ggtggcgggg gtgcccgggc atttggaggc    1680
cgccagctgc atccccccctt ccccgcagga gaactcctac gtgtccagca ctggcagagc    1740
ccacagtggg gctgctccat ggcagcccct ggcagcgcca tcaggagcca gtgcccaggc    1800
agcagagcag ctgcagagag gccccaacca gcccgtggag agtgacgaga gcctaggcgg    1860
cctctctgct gccctgcgct cctggcactt gactccaagc tgccctctgg acccagcacc    1920
cctcagggag gccggctgtc ctcaggggga cacggcagga gaatcgagct gggggagtgg    1980
cccaggatcc cggcccacag ccgtggaagg actggcctt  ggcagctctg catcatcgtc    2040
gtcagagcca ccgcagatta tcatcaaccc tgcccgacga agatggtcc  agaagctggc    2100
cctgtacgag gatggggccc tggacagcct gcagctgctg tcgtccagct ccctcccagg    2160
cttgggcctg aacaggaca  ggcaggggcc cgaagaaagt gatgaatttc agagctgatg    2220
tgttcacctg ggcagatccc ccaaatccgg aagtcaaagt tctcatggtc agaagttctc    2280
atggtgcacg agtcctcagc actctgccgg cagtgggggt gggggcccat gcccgcgggg    2340
gagagaagga ggtggcccctg ctgttctagg ctctgtgggc ataggcaggc agagtggaac    2400
cctgcctcca tgccagcatc tgggggcaag gaaggctggc atcatccagt gaggaggctg    2460
gcgcatgttg ggaggctgct ggctgcacag acccgtgagg ggaggagagg ggctgctgtg    2520
cagggggtgtg gagtagggag ctggctcccc tgagagccat gcagggcgtc tgcagcccag    2580
gcctctggca gcagctcttt gcccatctct ttggacagtg gccaccctgc acaatggggc    2640
cgacgaggcc tagggccctc ctacctgctt acaatttgga aaagtgtggc cgggtgcggt    2700
ggctcacgcc tgtaatccca gcactttggg aggccaaggc aggaggatcg ctggagccca    2760
gtaggtcaag accagccagg gcaacatgat gagaccctgt ctctgccaaa aaattttta    2820
aactattagc ctggcgtggt agcgcacgcc tgtggtccca gctgctgggg aggctgaagt    2880
aggaggatca tttatgcttg ggaggtcgag gctgcagtga gtcatgattg tatgactgca    2940
ctccagcctg ggtgacagag caagaccctg tttcaaaaag aaaaaccctg ggaaaagtga    3000
agtatggctg taagtctcat ggttcagtcc tagcaagaag cgagaattct gagatcctcc    3060
agaaagtcga gcagcaccca cctccaacct cgggccagtg tcttcaggct ttactgggga    3120
cctgcgagct ggcctaatgt ggtggcctgc aagccaggcc atccctgggc ccacagacg     3180
agctccgagc caggtcaggc ttcggaggcc acaagctcag cctcaggccc aggcactgat    3240
tgtggcagag gggccactac ccaaggtcta gctaggccca agcctagtt  acccagacag    3300
tgagaagccc ctgaaggca  gaaaagttgg gagcatggca gacagggaag ggaaacattt    3360
```

| tcagggaaaa gacatgtatc acatgtcttc agaagcaagt caggtttcat gtaaccgagt | 3420 |
| gtcctcttgc gtgtccaaaa gtagcccagg gctgtagcac aggcttcaca gtgattttgt | 3480 |
| gttcagccgt gagtcacact acatgccccc gtgaagctgg gcattggtga cgtccaggtt | 3540 |
| gtccttgagt aataaaaacg tatgttccct aaaaaaaaaa aaa | 3583 |

<210> SEQ ID NO 66
<211> LENGTH: 3496
<212> TYPE: DNA
<213> ORGANISM: Homo sapiens

<400> SEQUENCE: 66

| gaattctatg gagtgtaatt ttgtgtatga attatatttt taaaacattg aagagttttc | 60 |
| agaaagaagg ctagtagagt tgattactga tactttatgc taagcagtac ttttttggta | 120 |
| gtacaatatt ttgttaggcg tttctgataa cactagaaag gacaagtttt atcttgtgat | 180 |
| aaattgatta atgtttacaa catgactgat aattatagct gaatagtcct taaatgatga | 240 |
| acaggttatt tagttttttaa atgcagtgta aaaagtgtgc tgtggaaatt ttatggctaa | 300 |
| ctaagtttat ggagaaaata ccttcagttg atcaagaata atagtggtat acaaagttag | 360 |
| gaagaaagtc aacatgatgc tgcaggaaat ggaaacaaat acaaatgata tttaacaaag | 420 |
| atagagttta cagtttttga actttaagcc aaattcattt gacatcaagc actatagcag | 480 |
| gcacaggttc aacaaagctt gtgggtattg acttccccca aaagttgtca gctgaagtaa | 540 |
| tttagcccac ttaagtaaat actatgatga taagctgtgt gaacttagct tttaaatagt | 600 |
| gtgaccatat gaaggtttta attacttttg tttattggaa taaaatgaga tttttgggt | 660 |
| tgtcatgtta aagtgcttat agggaaagaa gcctgcatat aatttttac cttgtggcat | 720 |
| aatcagtaat tggtctgtta ttcaggcttc atagcttgta accaaatata aataaaaggc | 780 |
| ataatttagg tattctatag ttgcttagaa ttttgttaat ataaatctct gtgaaaaatc | 840 |
| aaggagtttt aatattttca gaagtgcatc cacctttcag ggctttaagt tagtattact | 900 |
| caagattatg aacaaatagc acttaggtta cctgaaagag ttactacaac cccaaagagt | 960 |
| tgtgttctaa gtagtatctt ggaaattcag agagatactc atcctacctg aatataaact | 1020 |
| gagataaatc cagtaaagaa agtgtagtaa attctacata agagtctatc attgatttct | 1080 |
| tttggtggta aaaatcttag ttcatgtgaa gaaatttcat gtgaatgttt tagctatcaa | 1140 |
| acagcactgt cacctactca tgcacaaaac tgcctcccaa agacttttcc caggtccctc | 1200 |
| gtatcaaaac attaagagta taatggaaga tagcacgatc ttgtcagatt ggacaaacag | 1260 |
| caacaaacaa aaaatgaagt atgacttttc ctgtgaactc tacagaatgt ctacatattc | 1320 |
| aactttcccc gccggggtgc ctgtctcaga aaggagtctt gctcgtgctg gttttttatta | 1380 |
| tactggtgtg aatgacaagg tcaaatgctt ctgttgtggc ctgatgctgg ataactggaa | 1440 |
| actaggagac agtcctattc aaaagcataa acagctatat cctagctgta gctttattca | 1500 |
| gaatctggtt tcagctagtc tgggatccac ctctaagaat acgtctccaa tgagaaacag | 1560 |
| ttttgcacat tcattatctc ccaccttgga acatagtagc ttgttcagtg gttcttactc | 1620 |
| cagcctttct ccaaaccctc ttaattctag agcagttgaa gacatctctt catcgaggac | 1680 |
| taacccctac agttatgcaa tgagtactga agaagccaga tttcttacct accatatgtg | 1740 |
| gccattaact ttttttgtcac catcagaatt ggcaagagct ggttttttatt atataggacc | 1800 |
| tggagatagg gtagcctgct ttgcctgtgg tgggaagctc agtaactggg aaccaaagga | 1860 |
| tgatgctatg tcagaacacc ggaggcattt tcccaactgt ccattttttgg aaaattctct | 1920 |

-continued

```
agaaactctg aggtttagca tttcaaatct gagcatgcag acacatgcag ctcgaatgag    1980
aacatttatg tactggccat ctagtgttcc agttcagcct gagcagcttg caagtgctgg    2040
tttttattat gtgggtcgca atgatgatgt caaatgcttt tgttgtgatg gtggcttgag    2100
gtgttgggaa tctggagatg atccatgggt agaacatgcc aagtggtttc caaggtgtga    2160
gttcttgata cgaatgaaag gccaagagtt tgttgatgag attcaaggta gatatcctca    2220
tcttcttgaa cagctgttgt caacttcaga taccactgga gaagaaaatg ctgacccacc    2280
aattattcat tttggacctg gagaaagttc ttcagaagat gctgtcatga tgaatacacc    2340
tgtggttaaa tctgccttgg aaatgggctt aatagagac ctggtgaaac aaacagttca     2400
aagtaaaatc ctgacaactg gagagaacta taaaacagtt aatgatattg tgtcagcact    2460
tctaaatgct gaagatgaaa aagagagga ggagaaggaa aaacaagctg aagaaatggc     2520
atcagatgat ttgtcattaa ttcggaagaa cagaatggct ctctttcaac aattgacatg    2580
tgtgcttcct atcctggata atcttttaaa ggccaatgta attaataaac aggaacatga    2640
tattattaaa caaaaaacac agatacccttt acaagcgaga gaactgattg ataccatttt   2700
ggttaaagga aatgctgcgg ccaacatctt caaaaactgt ctaaagaaa ttgactctac     2760 attgtataag aacttatttg tggataagaa tatgaagtat attccaacag aagatgtttc    2820
aggtctgtca ctggaagaac aattgaggag gttgcaagaa gaacgaactt gtaaagtgtg    2880
tatggacaaa gaagtttctg ttgtatttat tccttgtggt catctggtag tatgccagga    2940
atgtgcccct tctctaagaa aatgcccat ttgcaggggg ataatcaagg gtactgttcg      3000
tacatttctc tcttaaagaa aaatagtcta tattttaacc tgcataaaaa ggtctttaaa    3060
atattgttga acacttgaag ccatctaaag taaaaaggga attatgagtt tttcaattag    3120
taacattcat gttctagtct gctttggtac taataatctt gtttctgaaa agatggtatc    3180
atatatttaa tcttaatctg tttatttaca agggaagatt tatgtttggt gaactatatt    3240
agtatgtatg tgtacctaag ggagtagtgt cactgcttgt tatgcatcat ttcaggagtt    3300
actggatttg ttgttctttc agaaagcttt gaatactaaa ttatagtgta gaaaagaact    3360
ggaaaccagg aactctggag ttcatcagag ttatggtgcc gaattgtctt tggtgctttt    3420
cacttgtgtt ttaaaataag gattttctc ttatttctcc ccctagtttg tgagaaacat     3480
ctcaataaag tgcttt                                                     3496
```

<210> SEQ ID NO 67
<211> LENGTH: 2764
<212> TYPE: DNA
<213> ORGANISM: Homo sapiens

<400> SEQUENCE: 67

```
ctctaaagct tagagccaag atggcgggat ccaggcaaag gggtctccgg gccagagttc      60
ggccgctgtt ctgcgccttg ctgctgtcac tcggtcgctt cgtccggggc gacggcgtgg     120
gaggagaccc cgcggtcgcg ttgccacatc gccgtttcga gtacaaatac agcttcaagg     180
ggccgcacct ggtgcagagc gacgggaccg tgcccttctg ggcccacgcg gggaatgcta     240
ttccaagttc agatcaaatt cgagtagcac catctttaaa aagccaaaga ggctcagtgt     300
ggacaaagac aaaagcggcc tttgagaact gggaagttga ggtgacattt cgagtgactg     360
gaagaggtcg aattggagct gatgccctag caatttggta tgcagaaaat caaggcttgg    420
agggccctgt gtttggatca gctgatctgt ggaatggtgt tggaatattt tttgattctt     480
```

```
ttgacaatga tggaaagaaa aataatcctg ctatagtaat tataggcaac aatggacaaa    540
tccattatga ccatcaaaat gacggggcta gtcaagcttt ggcaagttgc cagagggact    600
tccgcaacaa accctatcct gtccgagcaa agattaccta ttaccagaac acactgacag    660
taatgatcaa taatggcttt acaccagata aaaatgatta tgaattttgt gccaaagtgg    720
aaaatatgat tatccctgca caagggcatt ttggaatatc tgctgcaact ggaggtcttg    780
cagatgacca tgatgtcctt tcttttctga ctttccagtt gactgaacct ggaaaagagc    840
cgcccacacc agataaagaa atttcggaaa aggaaaaaga aagtatcag gaggaatttg     900
agcactttca acaagaattg gataaaaaaa agaggaatt ccagaagggc cacccccgacc    960
tccaagggca gcctgcggag gaaatatttg agagtgtagg agatcgagag ctaagacaag   1020
tctttgaagg acagaatcgt attcatcttg aaatcaagca gctgaaccgg cagttagata   1080
tgattcttga tgaacagaga agatatgtct cttccttaac agaggaaatc tctaaaagag   1140
gagcaggaat gcctgggcag catgggcaga ttactcaaca agaactggat actgttgtga   1200
aaactcagca tgagattctg agacaagtaa atgaaatgaa aaattccatg agtgaaaccg   1260
tcagactggt cagtggaatg cagcaccctg gctctgctgg aggcgtctat gagacaacac   1320
agcacttcat tgacatcaaa gagcacctgc acatagtaaa gagggacata gataacttag   1380
tgcagcgaaa tatgccatca aatgaaaagc cgaaatgccc agaactacca ccatttccat   1440
catgtttgtc tacggtccac ttcattatat ttgttgtggt gcaaactgta ttattcattg   1500
gttatatcat gtataggtct cagcaagaag cagctgccaa aaaattctttt tgactaccat   1560
tttcctgtgt acttcatcta tttgtgtaca aaatgatgtc gttttgaggg aatttaagta   1620
tttaaattgc ttcatagtct aaattattaa ttttcttaat aaaataactg tttaaacatt   1680
gatttgcagt taagaataaa ccttaaagca aagacaacca cattttaatt tgttcacagt   1740
atgtaaatct gtctaaattt cagtgaattt ctggtcagta tgatgcagcc tctgagcaga   1800
tattgaccag taagagggta aataaagtgg gggcaacccc tggatatgaa tgttacccc    1860
taagtctcca atattgcagg tttccctgta taacgtaaac acacttgccc tcatgcctcc   1920
cagaatatga ggtctaatta agaagtccca tcaggtttat tttgtaacca aagtctttt    1980
tagaggtcag acttcctaat caaaggcctg ggcctgcagt cctttcatct taatgcaact   2040
tcctttgaaa tcaagaata ttttgtctga gagctttaag gatctggtaa tagacttcaa    2100
aatgttaagt gaaatttttt ttcctctatt tatcaatgat atatttcact tttaaaggaa   2160
attttggagg aaaatatagc tgcttttgc ctaaaaaacc ttgtgggtgg aaatattcct    2220
ctgagaatgg cttttatagg tattttgcct ggtaatgtat tcattcatga ttgcccatat   2280
tcttgaatgt ttcttcattc caatgggtc aggtcaatat tatgaaaata atttttatat    2340
ttatatttgt aactaagaat ttatttctcc ctttactaca cgatgtaaat tcacgtcaaa   2400
ttcgatgatc tgaggattta aattcacaaa acctgccact acattctggt ttacattagt   2460
tacttcatgc tggctggggt tagtgaccat ttgcatactc ttttaaatca aggaggctgt   2520
agtagaggca gttttaagat tcttgaaggc aaaatttgaa aaacagtgaa tacttctaat   2580
tgtttccttt tagtgccaga actaagacat tgtgaagcac ttgttagtaa acttaacctt   2640
gaaatgtcag actggaagga gttttatgt ctttgtgcat acttctgggt attacagaaa    2700
cagtctgtaa ataacatttt aagatgcaaa tttaattctg ttcacagctg atttatactg   2760
attt                                                                2764
```

<210> SEQ ID NO 68
<211> LENGTH: 403
<212> TYPE: DNA
<213> ORGANISM: Homo sapiens

<400> SEQUENCE: 68

```
tttcattagt tatcattagt ttattataaa agagaaatat ggaaattatt tacatgacga      60
aagatttcag aacttcagtg gaatgggcag catcatgttg atgccatttc aatagtgact     120
tatttcagtc tacgtacttt ccaagaatgt caccatctct aaataggaaa taatccttgt     180
catctagaac tactttggtg cctccatatt ctgggagaag aactttatct ccaactttca     240
cgctaactgg ttgaatctct ccacccttc ctttagaacc cgatccaaca gcgactactg     300
ttgcttgcaa tacttttcct tgagattttt ctggaagcat aatgcctcct ttggttacag     360
tttcagcagc actcctttca accaatactc ggtcaaagag tgg                      403
```

<210> SEQ ID NO 69
<211> LENGTH: 656
<212> TYPE: DNA
<213> ORGANISM: Homo sapiens

<400> SEQUENCE: 69

```
acaactcggt ggtggccact gcgcagacca gacttcgctc gtactcgtgc gcctcgcttc      60
gcttttcctc cgcaaccatg tctgacaaac ccgatatggc tgagatcgag aaattcgata     120
agtcgaaact gaagaagaca gagacgcaag agaaaaatcc actgccttcc aaagaaacga     180
ttgaacagga gaagcaagca ggcgaatcgt aatgaggcgt cgccgccaa tatgcactgt      240
acattccaca agcattgcct tcttatttta cttcttttag ctgtttaact ttgtaagatg     300
caaagaggtt ggatcaagtt taaatgactg tgctgcccct ttcacatcaa agaactactg     360
acaacgaagg ccgcgcctgc ctttcccatc tgtctatcta tctggctggc agggaaggaa     420
agaacttgca tgttggtgaa ggaagaagtg gggtggaaga agtggggtgg acgacagtg      480
aaatctagag taaaaccaag ctggcccaag gtgtcctgca ggctgtaatg cagtttaatc     540
agagtgccat tttttttttt gttcaaatga ttttaattat tggaatgcac aatttttta     600
atatgcaaat aaaagtttta aaacttaaa aaaaaaaaa aaaaaaaaa aaaaa             656
```

<210> SEQ ID NO 70
<211> LENGTH: 361
<212> TYPE: DNA
<213> ORGANISM: Homo sapiens

<400> SEQUENCE: 70

```
ttttttttc aatgttcagt ttcctttaat gacccccatc tccctgaagg gcaggtgcag      60
gcagctaggt gatggcaaga gatgttcact tgaagatctt gccctgattg aaggctttgc     120
cacatgctgg aaggccccct cccaggaaaa gtactctcga accagcgtct gggtctcctc     180
gctgccagga tccagtttcc gccatgtgta tgactcgtag tccacctgcc aatctggact     240
cagcggaaag gcaagctcct ggcctcggaa gacccagact ccagaaatgg agtctgctat     300
tgttggttcc aaaaaggatg acactgggcg aaggcatttc ttcctcagct tgtccagttc     360
g                                                                     361
```

<210> SEQ ID NO 71
<211> LENGTH: 455
<212> TYPE: DNA
<213> ORGANISM: Homo sapiens
<220> FEATURE:

<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t

<400> SEQUENCE: 71

```
tttttttga taatttatga ttttattgtc tttcctttgt ccggccttta acatgtttct    60
gtaatttaaa taaaaatcta tttactttct ccattttagc aaatggtttc tttacccaaa   120
taggttgcac tatagtcccc atatggtttt ctactgttcc acaaccacta tttcacaaag   180
attgacaaaa ctttaataaa agttaaattt acaggacatc ttaaggataa cttggggaaa   240
tatgtaggta aaaaaggaat cgagtccaca aattaaggaa tattttgcta atatggccca   300
acaccaattt caggcaaatc caatctactt aactcatata tttaatgtgg ggtaattttt   360
cttaaccaaa atttangggg gggtatggan tggatattat ttatggccct tggacaaggg   420
tggacngtgt ggntttgttg tggactaggg nggggg                             455
```

<210> SEQ ID NO 72
<211> LENGTH: 645
<212> TYPE: DNA
<213> ORGANISM: Homo sapiens

<400> SEQUENCE: 72

```
ctcctgcagc gtctggggtt tccgttgcag tcctcggaac caggacctcg gcgtggccta    60
gcgagttatg gcgacgaagg ccgtgtgcgt gctgaagggc gacggcccag tgcagggcat   120
catcaatttc gagcagaagg aaagtaatgg accagtgaag gtgtggggaa gcattaaagg   180
actgactgaa ggcctgcatg gattccatgt tcatgagttt ggagataata cagcaggctg   240
taccagtgca ggtcctcact ttaatcctct atccagaaaa cacggtgggc caaaggatga   300
agagaggcat gttggagact tgggcaatgt gactgctgac aaagatggtg tggccgatgt   360
gtctattgaa gattctgtga tctcactctc aggagaccat tgcatcattg gccgcacact   420
ggtggtccat gaaaaagcag atgacttggg caaaggtgga aatgaagaaa gtacaaagac   480
aggaaacgct ggaagtcgtt tggcttgtgg tgtaattggg atcgcccaat aaacattccc   540
ttggatgtag tctgaggccc cttaactcat ctgttatcct gctagctgta gaaatgtatc   600
ctgataaaca ttaaacactg taatcttaaa aaaaaaaaaa aaaaa                   645
```

<210> SEQ ID NO 73
<211> LENGTH: 1684
<212> TYPE: DNA
<213> ORGANISM: Homo sapiens

<400> SEQUENCE: 73

```
gctttcacaa atacagctct gcaacgcgtt tgccctgata ccatgtctct tcgactttcc    60
agtgcatcca ggaggtcctg tcctcgtccc accactggat cactcagact ctatggtggg   120
```

-continued

```
ggaaccagct ttggtactgg aaattcttgt ggcatttcag ggattggaag tggcttctct       180
agtgccttcg gaggcagctc atcgggagga aacacagggg gaggtaatcc ctgtgctggc       240
ttcactgtga atgagcgggg gctcctttct ggcaatgaga aggtgaccat gcagaacctc       300
aatgaccgcc tggcatccta cctggacagt gtgcatgctc tggaggaggc caacgctgac       360
ctggagcaga agatcaaggg ctggtatgag aaatttgggc ctggctcttg ccgtggtctt       420
gatcatgact atagcagata tttcccaata attgatgacc ttaaaaatca gatcatcgca       480
tccaccacca gcaatgctaa tgctgttctg cagatcgata atgccaggct tacagctgat       540
gatttcagac tcaagtatga aaatgagctg gctcttcacc agagtgtaga ggctgatgtc       600
aatgggttac gaagagtttt ggatgaaata accctgtgca gaacagatct ggagattcag       660
tatgaaaccc tgagtgagga gatgacttac ctcaaaaaga accataaaga ggaaatgcaa       720
gttctgcagt gcgcagctgg aggcaacgtg aacgtggaga tgaacgcagc ccccggggtg       780
gacctcacag ttctgctgaa caacatgcga gctgagtacg aagcccttgc agagcagaac       840
cgcagggacg cggaggcctg gttcaacgag aagagcgcct ccctgcagca gcagatctct       900
gaggatgtcg gagccacaac ctcagcccgg aatgagctga ctgaaatgaa gcgcactctt       960
caaaccctgg aaattgaact tcagtctctc ctagccacga aacactccct ggagtgctcc      1020
ttgacagaga ccgagagcaa ctactgtgcg cagctggcgc agatccaggc tcagatcggg      1080
gccctggagg agcagctgca ccaggtcaga accgagaccg agggccagaa gctggagtat      1140
gagcagctcc tggacatcaa gctccacctg gaaaaagaaa ttgagaccta ctgtctcctt      1200
ataggaggag atgatggagc ctgtaagtct ggggggttaca agtctaaaga ttatggatct      1260
ggaaatgtgg gaagtcaagt caaagaccca gccaaagcca tagtggttaa gaaagttctt      1320
gaggaggtag accaacgcag caaaatactt accaccaggc tccactccct ggaagagaaa      1380
tctcaaagca attaatttga gatgcaacag agaacgtatg ccacatagcc cctgcgaaga      1440
aaaggcatta tgtatctgtc cagaaaaatg tgcatgtcta agaaaaatgt ctaacctgtt      1500
gtctttctgt tactttcttt ctgggcaatc aatgacagca tctccccatt catctagaag      1560
aatgccacac acaaatatga ctcatttgat tatcctacag aaatctgttg tcaattcttt      1620
gtattcaata aacctcttct ttagcaagtt aaaaaaaaaa aaaaaaaaaa aaaaaaaaa       1680 aaaa                                                                  1684
```